(12) United States Patent
Schroeder et al.

(10) Patent No.: US 10,450,318 B2
(45) Date of Patent: Oct. 22, 2019

(54) CXCR4 RECEPTOR ANTAGONISTS

(71) Applicant: BRISTOL-MYERS SQUIBB COMPANY, Princeton, NJ (US)

(72) Inventors: Gretchen M. Schroeder, Ewing, NJ (US); Tram N. Huynh, Pennington, NJ (US); Heidi L. Perez, Ewing, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 15/776,936

(22) PCT Filed: Dec. 14, 2016

(86) PCT No.: PCT/US2016/066575
§ 371 (c)(1),
(2) Date: May 17, 2018

(87) PCT Pub. No.: WO2017/106291
PCT Pub. Date: Jun. 22, 2017

(65) Prior Publication Data
US 2018/0327409 A1  Nov. 15, 2018

Related U.S. Application Data

(60) Provisional application No. 62/267,649, filed on Dec. 15, 2015.

(51) Int. Cl.
*C07D 487/04* (2006.01)
*A61P 35/00* (2006.01)
*C07D 519/00* (2006.01)

(52) U.S. Cl.
CPC ............ *C07D 487/04* (2013.01); *A61P 35/00* (2018.01); *C07D 519/00* (2013.01)

(58) Field of Classification Search
CPC .............................. C07D 487/04; A61P 35/00
See application file for complete search history.

(56) References Cited

FOREIGN PATENT DOCUMENTS

WO   WO 2007/087549 A2   8/2007

*Primary Examiner* — Golam M Shameem
(74) *Attorney, Agent, or Firm* — Elliot Korsen; James Epperson

(57) ABSTRACT

The invention generally relates to compounds of formula I which are antagonists of CXCR4. The invention includes pharmaceutically acceptable salts, compositions, methods of making the compounds of formula I, and methods of using the compounds of formula I for therapeutic indications.

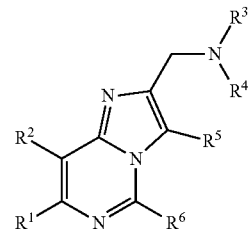

11 Claims, No Drawings

CXCR4 RECEPTOR ANTAGONISTS

CROSS-REFERENCE TO RELATED APPLICATIONS

This application claims priority to U.S. Provisional Patent Application Ser. No. 62/267,649 filed Dec. 15, 2015, which is incorporated by reference in its entirety.

FIELD OF THE INVENTION

The invention relates generally to compounds that modulate the activity of CXCR4, pharmaceutical compositions containing said compounds and methods of treating proliferative disorders and disorders of dysregulated apoptosis, such as cancer, utilizing the compounds of the invention.

BACKGROUND OF THE INVENTION

Chemokines are a family of about 50 small proteins that modulate cell trafficking and angiogenesis and also play a significant role in the tumor microenvironment (Vicari et al., 2002, Cytokine Growth Factor Rev, 13:143-154). Depending on their structure, chemokines are classified as C—C chemokines (containing a cysteine-cysteine motif) or C—X—C chemokines (containing a cysteine-X-cysteine motif). Receptors that bind such chemokines thus are classified as members of the CCR family or CXCR family, respectively. One member of the CXCR family is CXCR4, a seven transmembrane G-protein coupled receptor that is predominantly expressed on lymphocytes and that activates chemotaxis. CXCR4 binds the chemokine CXCL12 (SDF-1).

CXCR4 plays a role in embryogenesis, homeostasis and inflammation. Studies with mice engineered to be deficient in CXCR4 or SDF-1 implicate the CXCR4/SDF-1 pathway in organ vascularization, as well as in the immune and hematopoietic systems (Tachibana et al., 1998, Nature, 393:591-594). Moreover, CXCR4 has been shown to function as a coreceptor for T lymphotrophic HIV-1 isolates (Feng et al., 1996, Science, 272:872-877). CXCR4 also has been shown to be expressed on a wide variety of cancer cell types. Additionally, the CXCR4/SDF-1 pathway has been shown to be involved in stimulating the metastatic process in many different neoplasms (Murphy, 2001, N Eng. J Med, 345:833-835). For example, CXCR4 and SDF-1 have been shown to mediate organ-specific metastasis by creating a chemotactic gradient between the primary tumor site and the metastatic site (Muller et al., 2001, Nature, 410:50-56; Murakami et al., 2002, Cancer Res, 62:7328-7334; Hanahan et al., 2003, Cancer Res, 63:3005-3008).

Evidence has been presented suggesting that CXCL12 may be immunosuppressive and may support the stroma surrounding the tumor, shielding it from immune mechanisms that would otherwise result in tumor cell killing (Feig et al., 2013, Proc Natl Acad Sci, 110:20212-20217; Domanska et al., 2013, Eur J Cancer, 49:219-30; Duda et al., 2011, Clin Cancer Res, 17:2074-80; Burger et al., 2006, Blood, 107:1761-7). The refractory nature of many metastatic tumors may result from an immunosuppressive environment surrounding the tumor that prevents activated lymphocytes from accessing the tumor site. It is, therefore, of interest to determine whether disruption of the stromal microenvironment via CXCR4 blockade could increase the tumor's susceptibility to immune-targeted therapies and allow for the penetration of immune cells to the tumor site.

DESCRIPTION OF THE INVENTION

One aspect of the invention is a compound of formula I

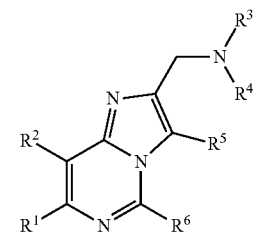

where:
$R^1$ is hydrogen, cyano, halo, alkyl, haloalkyl, hydroxyalkyl, alkoxyalkyl, alkoxy, and haloalkoxy;
$R^2$ is hydrogen, cyano, halo, alkyl, haloalkyl, hydroxyalkyl, alkoxyalkyl, alkoxy, and haloalkoxy;
$R^3$ is tetrahydroquinolinyl, dihydropyranopyridinyl, tetrahydrocinnolinyl, tetrahydroquinazolinyl, or tetrahydroquinoxalinyl, and is substituted with 0-3 substituents selected from halo, alkyl, haloalkyl, alkoxy, and haloalkoxy;
$R^4$ is hydrogen, alkyl, hydroxyalkyl, alkoxyalkyl, ($R^7$)alkyl, (($R^7$)cycloalkyl)alkyl, ((($R^7$)alkyl)cycloalkyl)alkyl, ($R^7$)cycloalkyl, or (($R^7$)alkyl)cycloalkyl;
$R^5$ is hydrogen, halo, alkyl, haloalkyl, hydroxyalkyl, alkoxyalkyl, alkoxy, haloalkoxy, ($R^7$)alkyl, (($R^7$)cycloalkyl)alkyl, ((($R^7$)alkyl)cycloalkyl)alkyl, ($R^7$)cycloalkyl, or (($R^7$)alkyl)cycloalkyl;
$R^6$ is hydrogen, alkyl, hydroxy, alkoxy, alkylthio, ($R^7$)alkyl, (($R^7$)cycloalkyl)alkyl, ((($R^7$)alkyl)cycloalkyl)alkyl, ($R^7$)cycloalkyl, or (($R^7$)alkyl)cycloalkyl; or $R^6$ is azetidinyl, pyrrolidinyl, piperidinyl, piperazinyl, morpholinyl, homopiperidinyl, homopiperazinyl, diazabicycloheptanyl, octahydropyrrolopyrrolyl, octahydropyrrolopyrazinyl, octahydropyrrolopyridinyl, octahydropyridopyrazinyl, octahydropyrazinooxazinyl, or tetrahydrotriazolopyrazinyl, and is substituted with 0-4 substituents selected from halo, alkyl, (cycloalkyl)alkyl, (tetrahydropyranyl)alkyl, haloalkyl, hydroxyalkyl, alkoxyalkyl, ($R^7$)alkyl, carboxyalkyl, (alkoxycarbonyl)alkyl, ($Ar^1$)alkyl, diphenylalkyl, cycloalkyl, $R^7$, alkylcarbonyl, alkoxycarbonyl, ($R^7$)NCO, ($Ar^2$)aminocarbonyl, alkylsulfonyl, ($Ar^2$)sulfonyl, and $Ar^2$, and is also substituted with 0-3 halo or alkyl substituents;
$R^7$ is $(R^8)(R^9)N$;
or $R^7$ is azetidinyl, pyrrolidinyl, piperidinyl, piperazinyl, morpholinyl, homopiperidinyl, homopiperazinyl, or octahydropyrrolopyrazinyl, and is substituted with 0-3 halo or alkyl substituents;
$R^8$ is hydrogen or alkyl;
$R^9$ is hydrogen or alkyl;
$Ar^1$ is pyrrolyl, furanyl, thienyl, pyrazolyl, isoxazolyl, isothiazolyl, imidazoyl, oxazolyl, thiazolyl, triazolyl, oxadiazolyl, thiadiazolyl, tetrazolyl, pyridinyl, pyridazinyl, pyrimidinyl, pyrazinyl, phenyl, or biphenyl and is substituted with 0-3 substituents selected from cyano, halo, alkyl, haloalkyl, hydroxy, alkoxy, haloalkoxy, phenoxy, and $R^7$; and
$Ar^2$ is phenyl, pyridinyl, or thienyl and is substituted with 0-3 substituents selected from halo, alkyl, haloalkyl, alkoxy, and haloalkoxy;
or a pharmaceutically acceptable salt thereof.
Another aspect of the invention is a compound of formula I where:

$R^1$ is hydrogen, cyano, halo, alkyl, haloalkyl, hydroxyalkyl, alkoxyalkyl, alkoxy, and haloalkoxy;

$R^2$ is hydrogen, cyano, halo, alkyl, haloalkyl, hydroxyalkyl, alkoxyalkyl, alkoxy, and haloalkoxy;

$R^3$ is tetrahydroquinolinyl, dihydropyranopyridinyl, tetrahydrocinnolinyl, tetrahydroquinazolinyl, or tetrahydroquinoxalinyl, and is substituted with 0-3 substituents selected from halo, alkyl, haloalkyl, alkoxy, and haloalkoxy;

$R^4$ is hydrogen, alkyl, hydroxyalkyl, alkoxyalkyl, $(R^7)$alkyl, $((R^7)$cycloalkyl)alkyl, $(((R^7)$alkyl)cycloalkyl)alkyl, $(R^7)$cycloalkyl, or $((R^7)$alkyl)cycloalkyl;

$R^5$ is hydrogen, halo, alkyl, haloalkyl, hydroxyalkyl, alkoxyalkyl, alkoxy, haloalkoxy, $(R^7)$alkyl, $((R^7)$cycloalkyl)alkyl, $(((R^7)$alkyl)cycloalkyl)alkyl, $(R^7)$cycloalkyl, or $((R^7)$alkyl)cycloalkyl;

$R^6$ is hydrogen, alkyl, hydroxy, alkoxy, alkylthio, $(R^7)$alkyl, $((R^7)$cycloalkyl)alkyl, $(((R^7)$alkyl)cycloalkyl)alkyl, $(R^7)$cycloalkyl, or $((R^7)$alkyl)cycloalkyl;

or $R^6$ is azetidinyl, pyrrolidinyl, piperidinyl, piperazinyl, morpholinyl, homopiperidinyl, homopiperazinyl, octahydropyrrolopyrazinyl, or octahydropyridopyrazinyl, and is substituted with 0-4 substituents selected from alkyl, (cycloalkyl)alkyl, (tetrahydropyranyl)alkyl, haloalkyl, hydroxyalkyl, alkoxyalkyl, $(R^7)$alkyl, carboxyalkyl, (alkoxycarbonyl)alkyl, $(Ar^1)$alkyl, diphenylalkyl, cycloalkyl, $R^7$, alkylcarbonyl, alkoxycarbonyl, $R^7$CO, $(Ar^2)$aminocarbonyl, alkylsulfonyl, and $(Ar^2)$sulfonyl, and is also substituted with 0-3 halo or alkyl substituents;

$R^7$ is $(R^8)(R^9)$N;

or $R^7$ is azetidinyl, pyrrolidinyl, piperidinyl, piperazinyl, morpholinyl, homopiperidinyl, homopiperazinyl, or octahydropyrrolopyrazinyl, and is substituted with 0-3 halo or alkyl substituents;

$R^8$ is hydrogen or alkyl;

$R^9$ is hydrogen or alkyl;

$Ar^1$ is pyrrolyl, furanyl, thienyl, pyrazolyl, isoxazolyl, isothiazolyl, imidazoyl, oxazolyl, thiazolyl, triazolyl, oxadiazolyl, thiadiazolyl, tetrazolyl, pyridinyl, pyridazinyl, pyrimidinyl, pyrazinyl, phenyl, or biphenyl and is substituted with 0-3 substituents selected from cyano, halo, alkyl, haloalkyl, hydroxy, alkoxy, haloalkoxy, phenoxy, and $R^7$;

$Ar^2$ is phenyl, pyridinyl, or thienyl and is substituted with 0-3 substituents selected from halo, alkyl, haloalkyl, alkoxy, and haloalkoxy;

or a pharmaceutically acceptable salt thereof.

Another aspect of the invention is a compound of formula I where:

$R^1$ is hydrogen, halo, alkyl, haloalkyl, alkoxy, or haloalkoxy;

$R^2$ is hydrogen, halo, alkyl, haloalkyl, alkoxy, or haloalkoxy;

$R^3$ is tetrahydroquinolinyl or dihydropyranopyridinyl, and is substituted with 0-3 substituents selected from halo, alkyl, haloalkyl, alkoxy, and haloalkoxy;

$R^4$ is hydrogen, alkyl, hydroxyalkyl, alkoxyalkyl, or $(R^7)$alkyl;

$R^5$ is hydrogen, halo, alkyl, haloalkyl, hydroxyalkyl, alkoxyalkyl, alkoxy, or haloalkoxy;

$R^6$ is hydrogen, alkyl, alkoxy, or alkylthio;

or $R^6$ is azetidinyl, pyrrolidinyl, piperidinyl, piperazinyl, morpholinyl, homopiperidinyl, or homopiperazinyl, and is substituted with 0-1 substituents selected from halo, alkyl, (cycloalkyl)alkyl, (tetrahydropyranyl)alkyl, haloalkyl, hydroxyalkyl, alkoxyalkyl, $(R^7)$alkyl, carboxyalkyl, (alkoxycarbonyl)alkyl, $(Ar^1)$alkyl, diphenylalkyl, cycloalkyl, $R^7$, alkylcarbonyl, alkoxycarbonyl, alkylaminocarbonyl, $(Ar^2)$aminocarbonyl, alkylsulfonyl, $(Ar^2)$sulfonyl, and $Ar^2$, and is also substituted with 0-3 halo or alkyl substituents;

$R^7$ is $(R^8)(R^9)$N;

or $R^7$ is azetidinyl, pyrrolidinyl, piperidinyl, piperazinyl, morpholinyl, homopiperidinyl, or homopiperazinyl and is substituted with 0-3 halo or alkyl substituents;

$R^8$ is hydrogen or alkyl;

$R^9$ is hydrogen or alkyl;

$Ar^1$ is pyrrolyl, furanyl, thienyl, pyrazolyl, isoxazolyl, isothiazolyl, imidazoyl, oxazolyl, thiazolyl, triazolyl, oxadiazolyl, thiadiazolyl, tetrazolyl, pyridinyl, pyridazinyl, pyrimidinyl, pyrazinyl, phenyl, or biphenyl and is substituted with 0-3 substituents selected from cyano, halo, alkyl, haloalkyl, hydroxy, alkoxy, haloalkoxy, phenoxy, and $(R^8)(R^9)$N; and $Ar^2$ is phenyl, pyridinyl, or thienyl and is substituted with 0-3 substituents selected from halo, alkyl, haloalkyl, alkoxy, and haloalkoxy;

or a pharmaceutically acceptable salt thereof.

Another aspect of the invention is a compound of formula I where $R^1$ is hydrogen; $R^2$ is hydrogen; $R^3$ is tetrahydroquinolinyl or dihydropyranopyridinyl; $R^4$ is alkyl; $R^5$ is hydrogen; or $R^6$ is azetidinyl, pyrrolidinyl, piperidinyl, piperazinyl, morpholinyl, homopiperidinyl, or homopiperazinyl, and is substituted with 0-1 substituents selected from halo, alkyl, (cycloalkyl)alkyl, (tetrahydropyranyl)alkyl, haloalkyl, hydroxyalkyl, alkoxyalkyl, $(R^7)$alkyl, carboxyalkyl, (alkoxycarbonyl)alkyl, $(Ar^1)$alkyl, diphenylalkyl, cycloalkyl, $R^7$, alkylcarbonyl, alkoxycarbonyl, alkylaminocarbonyl, $(Ar^2)$aminocarbonyl, alkylsulfonyl, $(Ar^2)$sulfonyl, and $Ar^2$, and is also substituted with 0-3 halo or alkyl substituents; $R^7$ is $(R^8)(R^9)$N or $R^7$ is azetidinyl, pyrrolidinyl, piperidinyl, piperazinyl, morpholinyl, homopiperidinyl, or homopiperazinyl and is substituted with 0-3 halo or alkyl substituents; $R^8$ is hydrogen or alkyl; $R^9$ is hydrogen or alkyl; $Ar^1$ is pyrrolyl, furanyl, thienyl, pyrazolyl, isoxazolyl, isothiazolyl, imidazoyl, oxazolyl, thiazolyl, triazolyl, oxadiazolyl, thiadiazolyl, tetrazolyl, pyridinyl, pyridazinyl, pyrimidinyl, pyrazinyl, phenyl, or biphenyl and is substituted with 0-3 substituents selected from cyano, halo, alkyl, haloalkyl, hydroxy, alkoxy, haloalkoxy, phenoxy, and $(R^8)(R^9)$N; and $Ar^2$ is phenyl, pyridinyl, or thienyl and is substituted with 0-3 substituents selected from halo, alkyl, haloalkyl, alkoxy, and haloalkoxy; or a pharmaceutically acceptable salt thereof.

Another aspect of the invention is a compound of formula I where $R^1$ is hydrogen; $R^2$ is hydrogen; $R^3$ is tetrahydroquinolinyl or dihydropyranopyridinyl; $R^4$ is alkyl; $R^5$ is hydrogen; $R^6$ is piperazinyl substituted with 0-1 substituents selected from halo, alkyl, (cycloalkyl)alkyl, (tetrahydropyranyl)alkyl, haloalkyl, hydroxyalkyl, alkoxyalkyl, $(R^7)$alkyl, carboxyalkyl, (alkoxycarbonyl)alkyl, $(Ar^1)$alkyl, diphenylalkyl, cycloalkyl, $R^7$, alkylcarbonyl, alkoxycarbonyl, alkylaminocarbonyl, $(Ar^2)$aminocarbonyl, alkylsulfonyl, $(Ar^2)$sulfonyl, and $Ar^2$, and is also substituted with 0-3 halo or alkyl substituents; $R^7$ is $(R^8)(R^9)$N or $R^7$ is azetidinyl, pyrrolidinyl, piperidinyl, piperazinyl, morpholinyl, homopiperidinyl, or homopiperazinyl and is substituted with 0-3 halo or alkyl substituents; $R^8$ is hydrogen or alkyl; $R^9$ is hydrogen or alkyl; $Ar^1$ is pyrrolyl, furanyl, thienyl, pyrazolyl, isoxazolyl, isothiazolyl, imidazoyl, oxazolyl, thiazolyl, triazolyl, oxadiazolyl, thiadiazolyl, tetrazolyl, pyridinyl, pyridazinyl, pyrimidinyl, pyrazinyl, phenyl, or biphenyl and is substituted with 0-3 substituents selected from cyano, halo, alkyl, haloalkyl, hydroxy, alkoxy, haloalkoxy, phenoxy, and $(R^8)(R^9)$N; and $Ar^2$ is phenyl, pyridinyl, or thienyl and is substituted with 0-3 substituents selected from halo, alkyl, haloalkyl, alkoxy, and haloalkoxy; or a pharmaceutically acceptable salt thereof.

Another aspect of the invention is a compound of formula I where $R^3$ is tetrahydroquinolinyl or dihydropyranopyridinyl.
p
Another aspect of the invention is a compound of formula I where $R^6$ is alkoxy, or alkylthio.

Another aspect of the invention is a compound of formula I where $R^6$ is piperazinyl substituted with 0-1 substituents selected from halo, alkyl, (cycloalkyl)alkyl, (tetrahydropyranyl)alkyl, haloalkyl, hydroxyalkyl, alkoxyalkyl, ($R^7$)alkyl, carboxyalkyl, (alkoxycarbonyl)alkyl, ($Ar^1$)alkyl, diphenylalkyl, cycloalkyl, $R^7$, alkylcarbonyl, alkoxycarbonyl, alkylaminocarbonyl, ($Ar^2$)aminocarbonyl, alkylsulfonyl, ($Ar^2$) sulfonyl, and $Ar^2$, and is also substituted with 0-3 halo or alkyl substituents.

For a compound of Formula I, the scope of any instance of a variable substituent, including $R^1$, $R^2$, $R^3$, $R^4$, $R^5$, $R^6$, $R^7$, $R^8$, $R^9$, $Ar^1$, and $Ar^2$ can be used independently with the scope of any other instance of a variable substituent. As such, the invention includes combinations of the different aspects.

Unless specified otherwise, these terms have the following meanings. "Alkyl" means a straight or branched alkyl group composed of 1 to 6 carbons. "Alkenyl" means a straight or branched alkyl group composed of 2 to 6 carbons with at least one double bond. "Alkynyl" means a straight or branched alkyl group composed of 2 to 6 carbons with at least one triple bond. "Cycloalkyl" means a monocyclic ring system composed of 3 to 7 carbons. Terms with a hydrocarbon moiety (e.g. alkoxy) include straight and branched isomers for the hydrocarbon portion which are composed of 1 to 6 carbons. "Halo" includes fluoro, chloro, bromo, and iodo. "Haloalkyl" and "haloalkoxy" include all halogenated isomers from monohalo to perhalo "Aryl" means a monocyclic or bicyclic aromatic ring system having 5 to 12 carbon atoms wherein one or both of the rings are aromatic. Representative examples of aryl groups include, but are not limited to, indanyl, indenyl, naphthyl, phenyl, and tetrahydronaphthyl. "Heteroaryl" means a 5 to 7 membered monocyclic or 8 to 11 membered bicyclic aromatic ring system with 1-5 heteroatoms independently selected from nitrogen, oxygen, and sulfur. Where a bonding attachment location is not specified, the bonding may be attached at any appropriate location as understood by practitioners in the art. Combinations of substituents and bonding patterns are only those that result in stable compounds as understood by practitioners in the art. Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate.

Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention exist in stereoisomeric forms. The invention includes all stereoisomeric forms of the compounds including enantiomers and diastereomers. Methods of making and separating stereoisomers are known in the art. The invention includes all tautomeric forms of the compounds. The invention includes atropisomers and rotational isomers.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Pharmaceutical Composition and Methods of Use

The compounds of this invention are antagonists of CXCR4. Accordingly, other aspects of the invention are pharmaceutical compositions and methods for treating therapeutic conditions associated with CXCR4.

"Pharmaceutically acceptable" refers to those compounds, materials, compositions, and/or dosage forms which are within the scope of sound medical judgment as understood by practitioners in the field.

"Therapeutically effective" means the amount of agent required to provide a meaningful patient benefit as understood by practitioners in the field.

"Patient" means an animal suitable for therapy as understood by practitioners in the field.

Another aspect of the invention provides pharmaceutically acceptable compositions which comprise a therapeutically effective amount of one or more of the compounds of Formula I, formulated together with one or more pharmaceutically acceptable carriers (additives) and/or diluents, and optionally, one or more additional therapeutic agents described above. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained release formulation; (3) topical application, for example, as a cream, ointment, or a controlled release patch or spray applied to the skin; (4) intravaginally or intrarectally, for example, as a pessary, cream or foam; (5) sublingually; (6) ocularly; (7) transdermally; or (8) nasally.

"Pharmaceutically acceptable carrier" refers to a pharmaceutically acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Other excipients include cyclodextrins, celluloses, liposomes, micelle forming agents, e.g., bile acids, and polymeric carriers, e.g., polyesters and polyanhydrides.

Compositions include those suitable for oral, nasal, topical (including buccal and sublingual), rectal, vaginal and/or parenteral administration. The compositions may conveniently be presented in unit dosage form and may be prepared by any methods well known in the art of pharmacy. The amount of active ingredient which can be combined with a carrier material to produce a single dosage form will vary depending upon the patient being treated and the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

Compositions for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms oral administration (capsules, tablets, pills, dragees, powders, granules, troches and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface active or dispersing agent. Molded tablets may be made by molding in a suitable machine a mixture of the powdered compound moistened with an inert liquid diluent.

The solid dosage forms may optionally be scored or prepared with coatings and shells, such as enteric coatings and other coatings well known in the pharmaceutical formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above described excipients.

Liquid dosage forms for oral administration include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Compositions for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Compositions which are suitable for vaginal administration also include pessaries, tampons, creams, gels, pastes, foams or spray formulations containing such carriers as are known in the art to be appropriate.

Dosage forms for topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions may include one or more pharmaceutically acceptable sterile isotonic aqueous or non-aqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents. Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsuled matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above.

Generally, oral, intravenous, intracerebroventricular and subcutaneous doses of the compounds of this invention for a patient will range from about 0.01 to about 50 mg per kilogram of body weight per day.

If desired, the effective daily dose of the active compound may be administered as two, three, four, five, six or more sub-doses administered separately at appropriate intervals throughout the day, optionally, in unit dosage forms. In certain aspects of the invention, dosing is one administration per day.

Pharmaceutical compositions may be presented in unit dose forms containing a predetermined amount of active ingredient pep unit dose. Preferred unit dosage compositions are those containing a daily dose or sub-dose, or an appropriate fraction thereof, of an active ingredient. Such unit doses may therefore be administered more than once a day. Preferred unit dosage compositions are those containing a daily dose or sub-dose (for administration more than once a day), as herein above recited, or an appropriate fraction thereof, of an active ingredient.

Compounds of the invention may be useful for the treatment of certain types of cancer by themselves or in combination or co-administration with other therapeutic agents or radiation therapy. Thus, in another aspect of the invention, compounds are co-administered with radiation therapy or a second therapeutic agent with cytostatic or antineoplastic activity. Suitable cytostatic chemotherapy compounds include, but are not limited to (i) antimetabolites; (ii) DNA-fragmenting agents, (iii) DNA-crosslinking agents, (iv) intercalating agents (v) protein synthesis inhibitors, (vi) topoisomerase I poisons, such as camptothecin or topotecan; (vii) topoisomerase II poisons, (viii) microtubule-directed agents, (ix) kinase inhibitors (x) miscellaneous investigational agents (xi) hormones and (xii) hormone antagonists. It is contemplated that compounds of the invention may be useful in combination with any known agents falling into the above 12 classes as well as any future agents that are currently in development. In particular, it is contemplated that compounds of the invention may be useful in combination with current Standards of Care as well as any that evolve over the foreseeable future. Specific dosages and dosing regimens would be based on physicians' evolving knowledge and the general skill in the art.

In another aspect of the invention, compounds of the invention may be co-formulated with an immuno-oncology agent. Immuno-oncology agents include, for example, a small molecule drug, antibody, or other biologic or small molecule. Examples of biologic immuno-oncology agents include, but are not limited to, cancer vaccines, antibodies, and cytokines. In one aspect, the antibody is a monoclonal antibody. In another aspect, the monoclonal antibody is humanized or human.

In another aspect of the invention, the immuno-oncology agent is (i) an agonist of a stimulatory (including a co-stimulatory) receptor or (ii) an antagonist of an inhibitory (including a co-inhibitory) signal on T cells, both of which result in amplifying antigen-specific T cell responses (often referred to as immune checkpoint regulators).

Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTβR, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα, LTβR, Lymphotoxin α 1β2, FAS, FASL, RELT, DR6, TROY, and NGFR.

In another aspect of the invention, the immuno-oncology agent is a cytokine that inhibits T cell activation (e.g., IL-6, IL-10, TGF-β, VEGF, and other immunosuppressive cytokines) or a cytokine that stimulates T cell activation, for stimulating an immune response.

In another aspect of the invention, T cell responses can be stimulated by a combination of a compound of the invention and one or more of (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4, and (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD28H.

Other agents that can be combined with compounds of the invention for the treatment of cancer include antagonists of inhibitory receptors on NK cells or agonists of activating receptors on NK cells. For example, compounds of the invention can be combined with antagonists of KIR, such as lirilumab.

Yet other agents for combination therapies include agents that inhibit or deplete macrophages or monocytes, including but not limited to CSF-1R antagonists such as CSF-1R antagonist antibodies including RG7155.

In another aspect of the invention, compounds of the invention can be used with one or more of agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell anergy or exhaustion) and agents that trigger innate immune activation and/or inflammation at tumor sites.

In another aspect of the invention, the immuno-oncology agent is a CTLA-4 antagonist, such as an antagonistic CTLA-4 antibody. Suitable CTLA-4 antibodies include, for example, YERVOY (ipilimumab) or tremelimumab.

In another aspect of the invention, the immuno-oncology agent is a PD-1 antagonist, such as an antagonistic PD-1 antibody. Suitable PD-1 antibodies include, for example, OPDIVO (nivolumab), KEYTRUDA (pembrolizumab), or MEDI-0680 (AMP-514; WO2012/145493). The immuno-oncology agent may also include pidilizumab (CT-011), though its specificity for PD-1 binding has been questioned. Another approach to target the PD-1 receptor is the recombinant protein composed of the extracellular domain of PD-L2 (B7-DC) fused to the Fc portion of IgG1, called AMP-224 In another aspect of the invention, the immuno-oncology agent is a PD-L1 antagonist, such as an antagonistic PD-L1 antibody. Suitable PD-L1 antibodies include, for example, MPDL3280A (RG7446; WO2010/077634), durvalumab (MEDI4736), BMS-936559 (WO2007/005874), and MSB0010718C (WO2013/79174).

In another aspect of the invention, the immuno-oncology agent is a LAG-3 antagonist, such as an antagonistic LAG-3 antibody. Suitable LAG3 antibodies include, for example, BMS-986016 (WO10/19570, WO14/08218), or IMP-731 or IMP-321 (WO008/132601, WO09/44273).

In another aspect of the invention, the immuno-oncology agent is a CD137 (4-1BB) agonist, such as an agonistic CD137 antibody. Suitable CD137 antibodies include, for example, urelumab and PF-05082566 (WO12/32433).

In another aspect of the invention, the immuno-oncology agent is a GITR agonist, such as an agonistic GITR antibody. Suitable GITR antibodies include, for example, BMS-986153, BMS-986156, TRX-518 (WO006/105021, WO009/009116) and MK-4166 (WO11/028683).

In another aspect of the invention, the immuno-oncology agent is an IDO antagonist. Suitable IDO antagonists include, for example, INCB-024360 (WO2006/122150, WO07/75598, WO008/36653, WO008/36642), indoximod, or NLG-919 (WO09/73620, WO009/1156652, WO11/56652, WO12/142237).

In another aspect of the invention, the immuno-oncology agent is a TGF-β antagonist. Suitable TGF-β antagonists include, for example, galunisterib (WO2004/048382, WO2007/018818) or tew-7197 (WO2012/002680).

In another aspect of the invention, the immuno-oncology agent is an OX40 agonist, such as an agonistic OX40 antibody. Suitable OX40 antibodies include, for example, MEDI-6383 or MEDI-6469.

In another aspect of the invention, the immuno-oncology agent is an OX40L antagonist, such as an antagonistic OX40 antibody. Suitable OX40L antagonists include, for example, RG-7888 (WO006/029879).

In another aspect of the invention, the immuno-oncology agent is a CD40 agonist, such as an agonistic CD40 antibody. In yet another embodiment, the immuno-oncology agent is a CD40 antagonist, such as an antagonistic CD40 antibody. Suitable CD40 antibodies include, for example, lucatumumab or dacetuzumab.

In another aspect of the invention, the immuno-oncology agent is a CD27 agonist, such as an agonistic CD27 antibody. Suitable CD27 antibodies include, for example, varlilumab.

In another aspect of the invention, the immuno-oncology agent is MGA271 (to B7H3) (WO11/109400).

Another aspect of the invention is a method for the treatment and/or prophylaxis of various types of cancers, comprising administering to a patient in need of such treatment and/or prophylaxis a therapeutically effective amount of one or more compounds of the invention, alone, or, optionally, in combination with another compound of the invention and/or at least one other type of therapeutic agent. Types of cancers that may be treated with the compounds of this invention include, but are not limited to, brain cancers, skin cancers, bladder cancers, ovarian cancers, breast cancers, gastric cancers, pancreatic cancers, prostate cancers, colon cancers, blood cancers, lung cancers and bone cancers. Examples of such cancer types include neuroblastoma, intestine carcinoma such as rectum carcinoma, colon carcinoma, familiar adenomatous polyposis carcinoma and hereditary non-polyposis colorectal cancer, esophageal carcinoma, labial carcinoma, larynx carcinoma, hypopharynx carcinoma, tong carcinoma, salivary gland carcinoma, gastric carcinoma, adenocarcinoma, medullary thyroid carcinoma, papillary thyroid carcinoma, renal carcinoma, kidney parenchymal carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors such as glioblastoma, astrocytoma, meningioma, medulloblastoma and peripheral neuroectodermal tumors, Hodgkin lymphoma, non-Hodgkin lymphoma, Burkitt lymphoma, acute lymphatic leukemia (ALL), chronic lymphatic leukemia (CLL), acute myeloid leukemia (AML), chronic myeloid leukemia (CML), adult T-cell leukemia lymphoma, diffuse large B-cell lymphoma (DLBCL), hepatocellular carcinoma, gall bladder carcinoma, bronchial carcinoma, small cell lung carcinoma, non-small cell lung carcinoma, multiple myeloma, basalioma, teratoma, retinoblastoma, choroid melanoma, seminoma, rhabdomyosarcoma, craniopharyngioma, osteosarcoma, chondrosarcoma, myosarcoma, liposarcoma, fibrosarcoma, Ewing sarcoma and plasmocytoma.

In addition to apoptosis defects found in tumors, defects in the ability to eliminate self-reactive cells of the immune system due to apoptosis resistance are considered to play a key role in the pathogenesis of autoimmune diseases. Autoimmune diseases are characterized in that the cells of the immune system produce antibodies against its own organs and molecules or directly attack tissues resulting in the destruction of the latter. A failure of those self-reactive cells to undergo apoptosis leads to the manifestation of the disease. Defects in apoptosis regulation have been identified in autoimmune diseases such as systemic lupus erythematosus or rheumatoid arthritis.

Another aspect of the invention are methods of treatment wherein compounds of the invention are administered with one or more immuno-oncology agents. The immuno-oncology agents used herein, also known as cancer immunotherapies, are effective to enhance, stimulate, and/or up-regulate immune responses in a subject. Another aspect of the invention is the administration of a compound of the invention with an immuno-oncology agent has a synergic effect in inhibiting tumor growth.

In another aspect of the invention, the compound(s) of the invention are sequentially administered prior to administration of the immuno-oncology agent. In another aspect, compound(s) of the invention are administered concurrently with the immunology-oncology agent. In yet another aspect, compound(s) of the invention are sequentially administered after administration of the immuno-oncology agent.

Immuno-oncology agents include, for example, a small molecule drug, antibody, or other biologic or small molecule. Examples of biologic immuno-oncology agents include, but are not limited to, cancer vaccines, antibodies, and cytokines. In one aspect, the antibody is a monoclonal antibody. In another aspect, the monoclonal antibody is humanized or human.

In another aspect of the invention, the immuno-oncology agent is (i) an agonist of a stimulatory (including a co-stimulatory) receptor or (ii) an antagonist of an inhibitory (including a co-inhibitory) signal on T cells, both of which result in amplifying antigen-specific T cell responses (often referred to as immune checkpoint regulators).

Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTβR, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα, LTβR, Lymphotoxin α 1β2, FAS, FASL, RELT, DR6, TROY, and NGFR.

In another aspect of the invention, the immuno-oncology agent is a cytokine that inhibits T cell activation (e.g., IL-6, IL-10, TGF-β, VEGF, and other immunosuppressive cytokines) or a cytokine that stimulates T cell activation, for stimulating an immune response.

In one aspect, T cell responses can be stimulated by a combination of a compound of the invention and one or more of (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4, and (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD28H.

Other agents that can be combined with compounds of the invention for the treatment of cancer include antagonists of inhibitory receptors on NK cells or agonists of activating receptors on NK cells. For example, compounds of the invention can be combined with antagonists of KIR, such as lirilumab.

Yet other agents for combination therapies include agents that inhibit or deplete macrophages or monocytes, including but not limited to CSF-1R antagonists such as CSF-1R antagonist antibodies including RG7155 (WO11/70024, WO11/107553, WO11/131407, WO13/87699, WO13/119716, WO13/132044) or FPA-008 (WO11/140249; WO13169264; WO14/036357).

In another aspect of the invention, compounds of the invention can be used with one or more of agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell anergy or exhaustion) and agents that trigger innate immune activation and/or inflammation at tumor sites.

In another aspect of the invention, the immuno-oncology agent is a CTLA-4 antagonist, such as an antagonistic CTLA-4 antibody. Suitable CTLA-4 antibodies include, for example, YERVOY (ipilimumab) or tremelimumab.

In another aspect of the invention, the immuno-oncology agent is a PD-1 antagonist, such as an antagonistic PD-1 antibody. Suitable PD-1 antibodies include, for example, OPDIVO (nivolumab), KEYTRUDA (pembrolizumab), or MEDI-0680 (AMP-514; WO2012/145493). The immuno-oncology agent may also include pidilizumab (CT-011), though its specificity for PD-1 binding has been questioned. Another approach to target the PD-1 receptor is the recombinant protein composed of the extracellular domain of PD-L2 (B7-DC) fused to the Fc portion of IgG1, called AMP-224 In another aspect of the invention, the immuno-oncology agent is a PD-L1 antagonist, such as an antagonistic PD-L1 antibody. Suitable PD-L1 antibodies include, for example, MPDL3280A (RG7446; WO2010/077634), durvalumab (MED14736), BMS-936559 (WO2007/005874), and MSB0010718C (WO2013/79174).

In another aspect of the invention, the immuno-oncology agent is a LAG-3 antagonist, such as an antagonistic LAG-3 antibody. Suitable LAG3 antibodies include, for example, BMS-986016 (WO10/19570, WO14/08218), or IMP-731 or IMP-321 (WO008/132601, WO09/44273).

In another aspect of the invention, the immuno-oncology agent is a CD137 (4-1BB) agonist, such as an agonistic CD137 antibody. Suitable CD137 antibodies include, for example, urelumab and PF-05082566 (WO12/32433).

In another aspect of the invention, the immuno-oncology agent is a GITR agonist, such as an agonistic GITR antibody. Suitable GITR antibodies include, for example, BMS-986153, BMS-986156, TRX-518 (WO006/105021, WO009/009116) and MK-4166 (WO11/028683).

In another aspect of the invention, the immuno-oncology agent is an IDO antagonist. Suitable IDO antagonists include, for example, INCB-024360 (WO2006/122150, WO07/75598, WO008/36653, WO008/36642), indoximod, or NLG-919 (WO09/73620, WO009/1156652, WO11/56652, WO12/142237).

In another aspect of the invention, the immuno-oncology agent is a TGF-β antagonist. Suitable TGF-β antagonists include, for example, galunisterib (WO2004/048382, WO2007/018818) or tew-7197 (WO2012/002680).

In another aspect of the invention, the immuno-oncology agent is an OX40 agonist, such as an agonistic OX40 antibody. Suitable OX40 antibodies include, for example, MEDI-6383 or MEDI-6469.

In another aspect of the invention, the immuno-oncology agent is an OX40L antagonist, such as an antagonistic OX40 antibody. Suitable OX40L antagonists include, for example, RG-7888 (WO006/029879).

In another aspect of the invention, the immuno-oncology agent is a CD40 agonist, such as an agonistic CD40 antibody. In yet another embodiment, the immuno-oncology agent is a CD40 antagonist, such as an antagonistic CD40 antibody. Suitable CD40 antibodies include, for example, lucatumumab or dacetuzumab.

In another aspect of the invention, the immuno-oncology agent is a CD27 agonist, such as an agonistic CD27 antibody. Suitable CD27 antibodies include, for example, varlilumab.

In another aspect of the invention, the immuno-oncology agent is MGA271 (to B7H3) (WO11/109400).

The combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner.

Substantially simultaneous administration can be accomplished, for example, by administering to the subject a single dosage form having a fixed ratio of each therapeutic agent or in multiple, single dosage forms for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Combination therapy also can embrace the administration of the therapeutic agents as described above in further combination with other biologically active ingredients and non-drug therapies (e.g., surgery or radiation treatment.) Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

Synthetic Methods

The compounds of the present invention may be prepared by synthetic routes that include processes analogous to those well-known in the chemical arts, particularly in light of the description provided herein. For illustrative purposes, Schemes 1-8 below show general methods for preparing the compounds of the present invention, as well as key intermediates. For a more detailed description of the individual reaction steps, see the Example section below. Those skilled in the art will appreciate that other synthetic routes may be used to synthesize the inventive compounds. Although specific starting materials and reagents are depicted in the Schemes and discussed below, other starting materials and reagents can easily be substituted to provide a variety of compounds of the present invention. In addition, many of the compounds prepared by the methods below can be further modified in light of this disclosure using conventional chemistry well known to those skilled in the art. The structure numbering and variable numbering shown in the synthetic schemes are distinct from, and should not be confused with, the structure or variable numbering in the claims or the rest of the specification. The variables in the schemes are meant only to illustrate how to make some of the compounds of this invention.

Compounds 3 can be prepared by coupling fragments 1 and 2 by reductive amination as shown in Scheme 1. Reaction of aldehyde 1 with amine 2 in the presence of a reducing agent such as sodium triacetoxyborohydride provides 3. Such reactions may be run in the presence or absence of an acid, such as acetic acid.

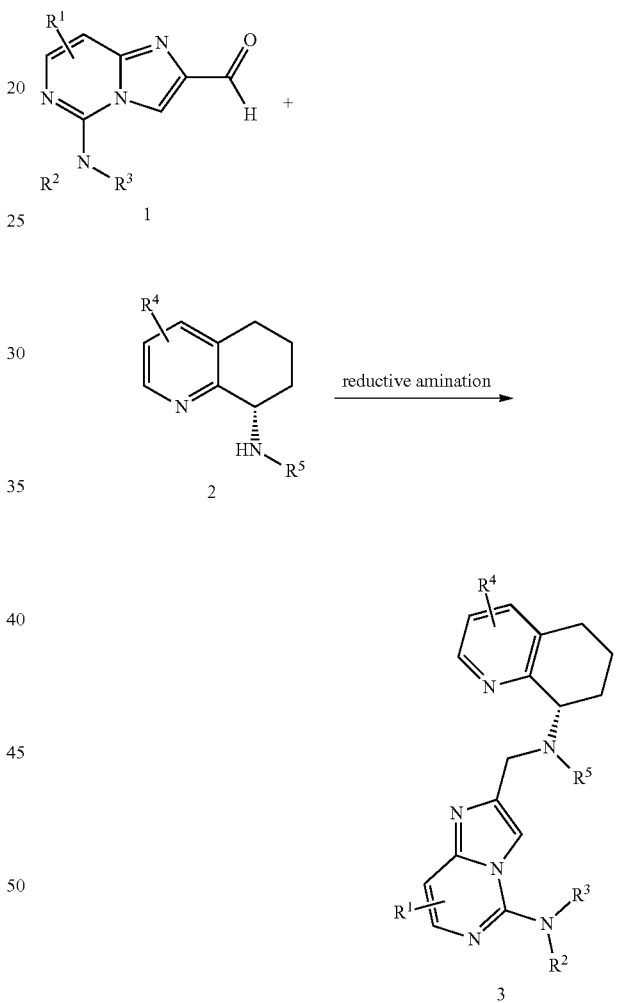

Aldehyde intermediate 1 may itself be prepared starting from commercially available pyrimidine 4 as shown in Scheme 2. Upon treatment with 1,1,3-trichloroacetone, pyrimidine 4 can be converted to imidazopyrimidine 5 which may then be treated with a variety of nucleophiles such as primary and secondary amines to give dichloride intermediate 6. Hydrolysis of the dichloride with, for example, sodium acetate gives the desired intermediate 1. Chiral amine intermediate 2 may be prepared by a variety of methods known in the literature (for example: Org. Process Res. Dev. 2009, 12, 823).

Scheme 2

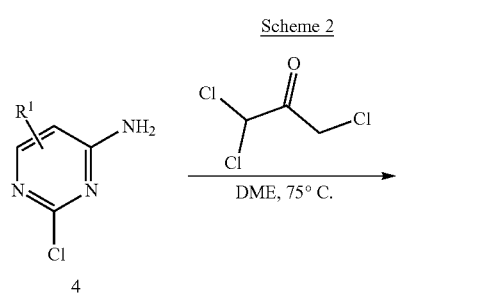

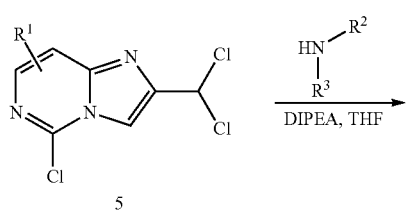

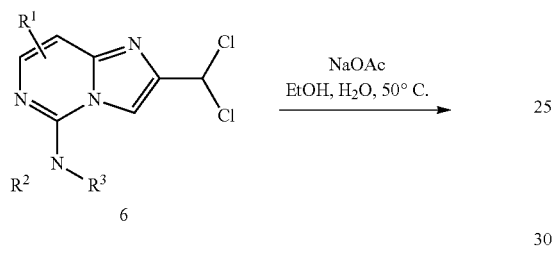

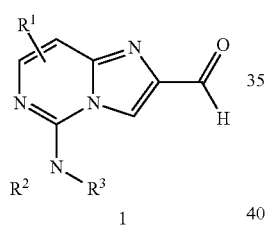

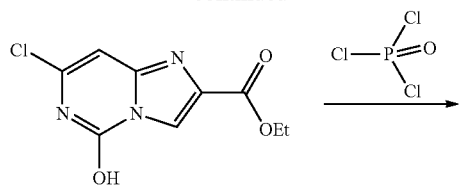

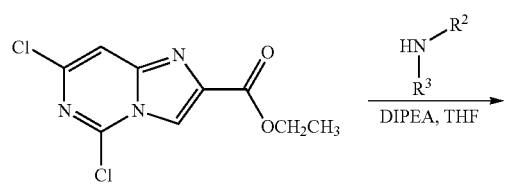

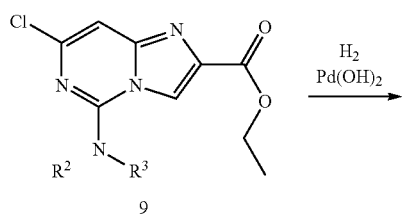

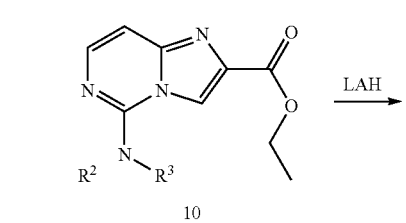

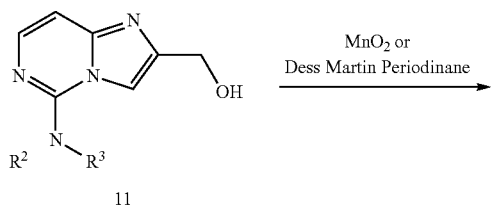

Alternatively, aldehyde 1 may be prepared as illustrated in Scheme 3. Dichloropyrimidine 4 can be treated with ethyl bromopyruvate to give imidazopyrimidine 7. Conversion to dichloride 8 using POCl₃ may be followed by selective displacement of the 5-chloro group to give compound 9. Hydrogenolysis in the presence of a palladium catalyst such as Pearlman's catalyst gives intermediate 10. The ester can then be reduced with LAH and the resulting alcohol oxidized with a variety of reagents such as manganese(IV) oxide or Dess Martin Periodinane to give aldehyde intermediate 1.

Scheme 3

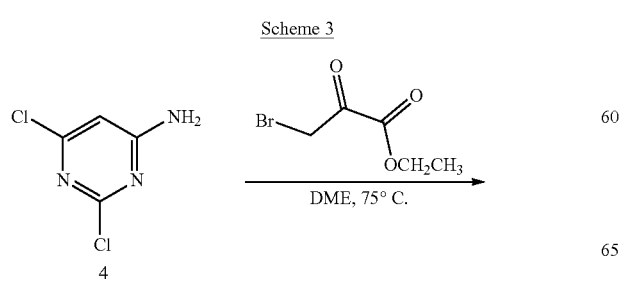

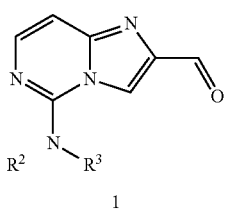

Compound 3 may be further elaborated as shown in Schemes 4-6. When R5 is not hydrogen, treatment with formaldehyde can give hydroxymethyl derivative 12.

Scheme 4

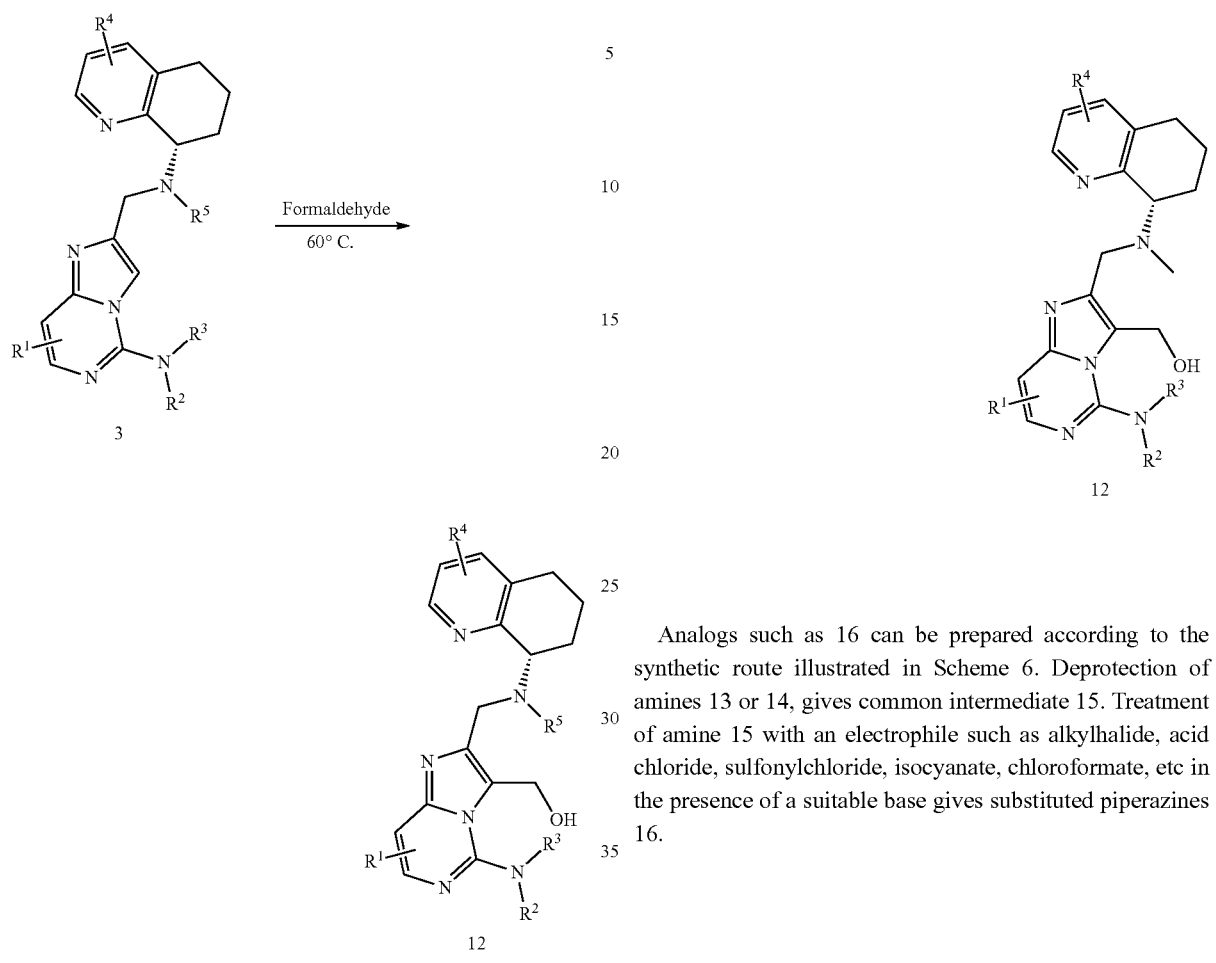

As illustrated in Scheme 5, when R5=H compound 3 can be converted to hydroxymethyl compound 12 where R5 has also been methylated.

Scheme 5

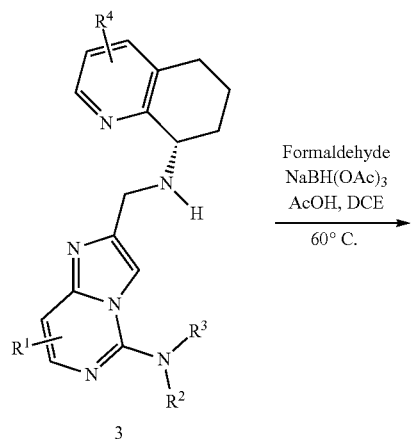

Analogs such as 16 can be prepared according to the synthetic route illustrated in Scheme 6. Deprotection of amines 13 or 14, gives common intermediate 15. Treatment of amine 15 with an electrophile such as alkylhalide, acid chloride, sulfonylchloride, isocyanate, chloroformate, etc in the presence of a suitable base gives substituted piperazines 16.

Scheme 6

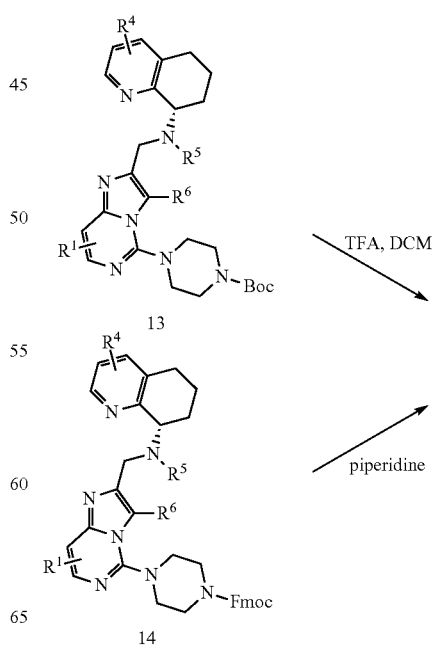

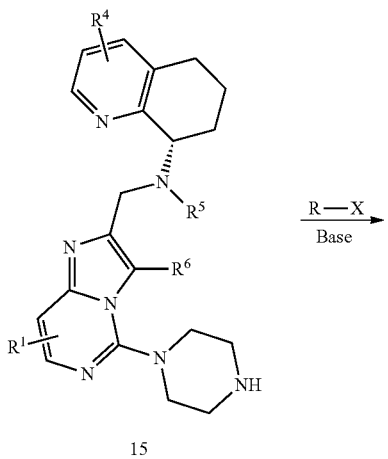

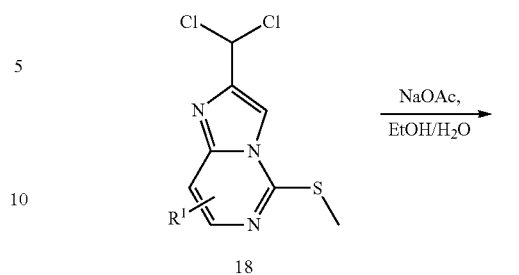

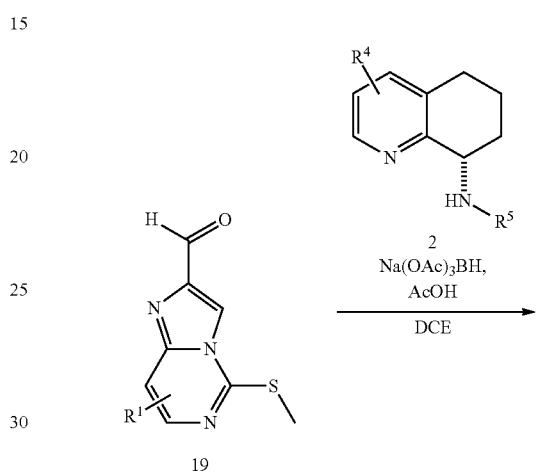

An alternative approach to compound 3 is shown in Scheme 7. Thioether substituted pyrimidine 17 can be first treated with 1,1,3-trichloroacetone to give imidazopyrimidine 18. Hydrolysis of the dichloride moiety gives aldehyde 19. Reductive amination with amine 2 in the presence of a reducing agent such as sodium triacetoxyborohydride gives thioether compound 20. Treatment with an amine nucleophile in the presence of a base, such as triethylamine, gives compound 3.

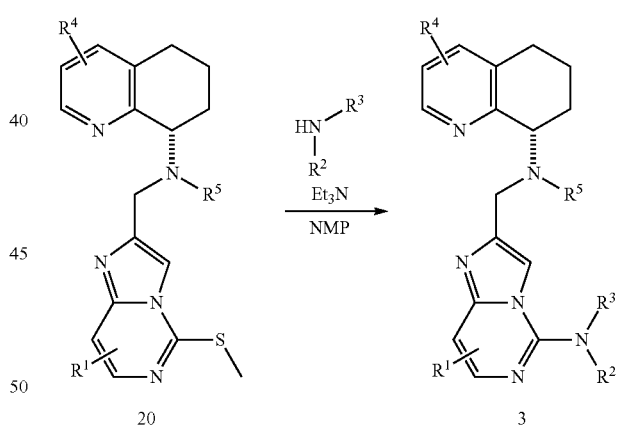

Pyran analogs 22 can be prepared from aldehyde 1 and amine 21 via reductive amination as shown in Scheme 8. Reaction of aldehyde 1 with amine 21 in the presence of a reducing agent such as sodium triacetoxyborohydride provides 22. Such reactions may be run in the presence or absence of an acid, such as acetic acid. Chiral amine intermediate 21 may be prepared as described in the literature (for example: WO2006/076131).

Compounds 22 may be further elaborated as described above. For example, treatment with formaldehyde yields alcohol 23.

Scheme 7

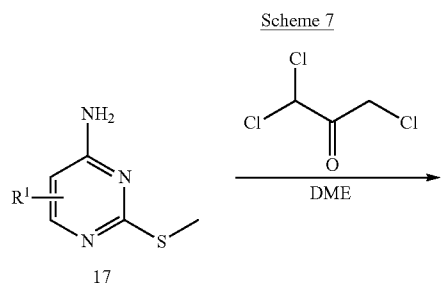

Scheme 8

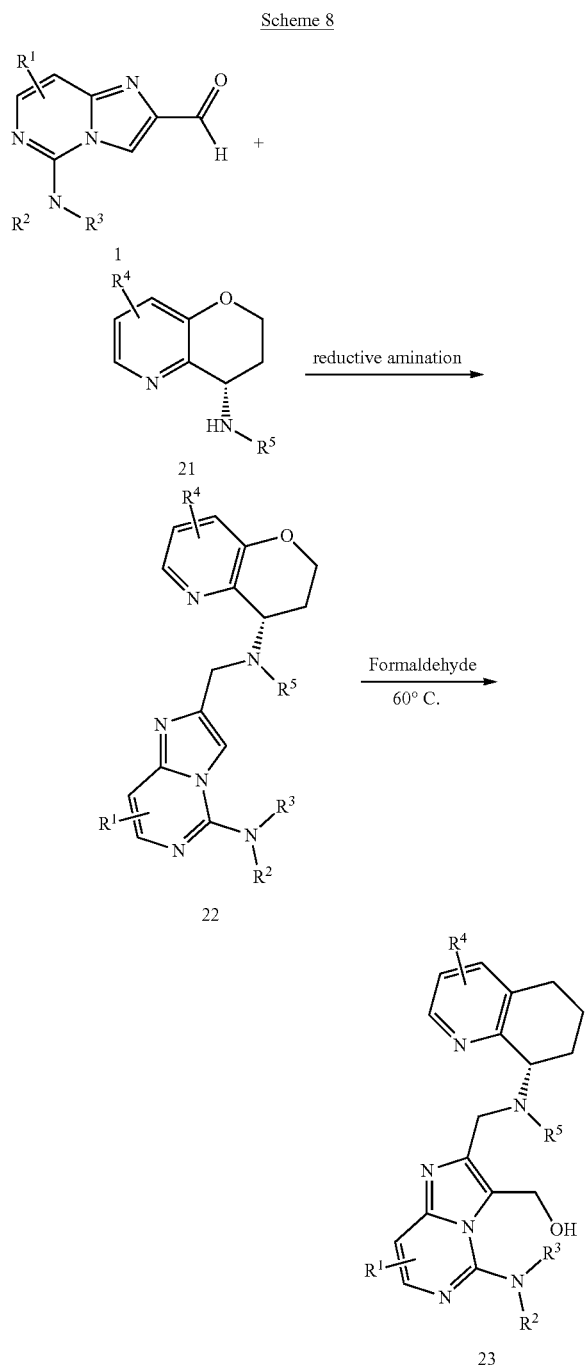

EXAMPLES

All reactions were carried out with continuous magnetic stirring under an atmosphere of dry nitrogen or argon. All evaporations and concentrations were carried out on a rotary evaporator under reduced pressure. Commercial reagents were used as received without additional purification. Solvents were commercial anhydrous grades and were used without further drying or purification. Flash chromatography was performed using prepacked RediSep® Rf silica gel columns or prepacked RediSep® Rf Gold C18 columns on a CombiFlash Rf machine.

Preparative Reverse Phase (RP) HPLC was performed with a linear gradient elution using $H_2O$/MeOH or $H_2O$/MeCN mixtures buffered with 0.1% trifluoroacetic acid or 10 mM $NH_4OAc$ and detection at 220 nm on one of the following columns: C18 Phenomenex Luna S5 ODS 30×100 mm (flow rate=30 mL/min), or C18 Phenomenex Luna Axia 21.20×100 mm column (flow rate=20 mL/min), or C18 Phenomenex Luna Axia 21.20×250 mm column (flow rate=30 mL/min), or Waters XBridge C18 19×250 mm (flow rate=20 mL/min), or Waters XBridge C18 19×200 mm (flow rate=20 mL/min).

All final products were characterized by $^1H$ NMR, RP HPLC and electrospray ionization (ESI) or atmospheric pressure ionization (API) mass spectrometry (MS). $^1H$ NMR spectra were obtained on a 500 MHz or a 400 MHz Bruker instrument. Field strengths are expressed in units of δ (parts per million, ppm) relative to the solvent peaks, and peak multiplicities are designated as follows: s, singlet; d, doublet; dd, doublet of doublets; t, triplet; q, quartet; sxt, sextet; br s, broad singlet; m, multiplet.

ABBREVIATIONS

Abbreviations used in the synthetic methods, schemes, and examples generally follow conventions used in the art.
2D Two dram
20D Twenty dram
Ac Acetyl
AcOH Acetic acid
aq Aqueous
Boc t-Butoxycarbonyl
$Boc_2O$ Di-t-butyl dicarbonate
conc Concentrated
DCE 1,2-Dichloroethane
DCM Dichloromethane
DIPEA N,N-Diisopropylethylamine
DMAP 4-N,N-dimethylaminopyridine
DME 1,2-Dimethoxyethane
DMF N,N-Dimethylformamide
DMSO Dimethyl sulfoxide
eq equivalents
EtOAc Ethyl acetate
EtOH Ethanol
$Et_2O$ Diethyl ether
$Et_3N$ Triethylamine
Fmoc 9-Flourenylmethoxycarbonyl
h Hour(s)
HPLC High performance liquid chromatography
i-PrOH Isopropanol
LAH Lithium aluminum hydride
m or min Minute(s)
Me Methyl
MeCN Acetonitrile
MeOH Methanol
NaOAc Sodium acetate
$Na(OAc)_3BH$ Sodium triacetoxyborohydride
$NH_4OAc$ Ammonium acetate
NMP N-methylpyrrolidinone
NMR Nuclear magnetic resonance
Pd/C Palladium on carbon
Ph Phenyl
$POCl_3$ Phosphorus(III) oxychloride
RT or rt Room temperature
sat Saturated
t-Bu Tertiary butyl
t-BuOH Tertiary butanol
TEA Triethylamine TFA Trifluoroacetic acid
THF Tetrahydrofuran Example 1

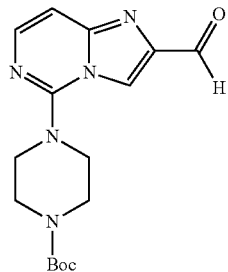

tert-Butyl 4-(2-formylimidazo[1,2-c]pyrimidin-5-yl)
piperazine-1-carboxylate

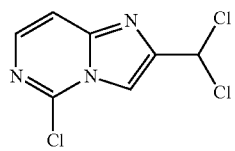 [SMILES: Clc1nccc2nc(C(Cl)Cl)cn12]

A) 5-Chloro-2-(dichloromethyl)imidazo[1,2-c]pyrimidine

A 250 mL round bottom flask was charged with 2-chloropyrimidin-4-amine (10 g, 77 mmol) and DME (100 ml). 1,1,3-Trichloroacetone (16.5 ml, 154 mmol) was added slowly and the reaction was stirred at 80° C. for 16 hours. The reaction solution was cooled, filtered and the precipitate washed with diethyl ether. The filtrate which contained the product was concentrated to near dryness. The residue was diluted with DCM, washed with saturated aqueous sodium bicarbonate solution followed by saturated aqueous sodium chloride solution, dried with anhydrous sodium sulfate, filtered and concentrated in vacuo. The crude product mixture was purified by a silica gel ISCO 120 g column eluting with 0-100% ethyl acetate/DCM over a 15 minute gradient. The appropriate fractions were isolated and concentrated in vacuo to afford the product (1.14 g, 6.24% yield) as a solid. $^1$H NMR (400 MHz, CHLOROFORM-d) δ 7.99 (s, 1H), 7.93 (d, J=6.4 Hz, 1H), 7.53 (dd, J=6.4, 0.7 Hz, 1H), 6.93 (d, J=0.6 Hz, 1H); MS (ESI$^+$) m/z 235.9 (M+H)$^+$.

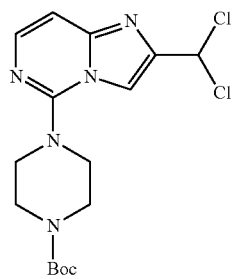 [SMILES: CC(C)(C)OC(=O)N1CCN(c2nccc3nc(C(Cl)Cl)cn23)CC1]

B) tert-Butyl 4-(2-(dichloromethyl)imidazo[1,2-c]pyrimidin-5-yl)piperazine-1-carboxylate A flask was charged with 5-chloro-2-(dichloromethyl)imidazo[1,2-c]pyrimidine (1.12 g, 4.74 mmol), 1-boc-piperazine (0.882 g, 4.7 mmol) and DIPEA (0.827 mL, 4.74 mmol) in tetrahydrofuran (20 mL). The reaction solution was stirred at RT for 18 hours. The reaction was quenched with water and extracted with DCM (3×). The pooled organic extracts were washed with water followed by saturated aqueous sodium chloride solution, dried with anhydrous sodium sulfate, filtered and concentrated in vacuo. The crude product mixture was purified by a silica gel ISCO 40 g column eluting with 0-100% ethyl acetate/DCM over a 15 minute gradient. The appropriate fractions were isolated and concentrated in vacuo to afford the product (1.86 g, 100% yield) as a solid. $^1$H NMR (400 MHz, CHLOROFORM-d) δ 7.81 (d, J=6.4 Hz, 1H), 7.64 (s, 1H), 7.21 (dd, J=6.4, 0.7 Hz, 1H), 6.92 (d, J=0.5 Hz, 1H), 3.80-3.64 (m, 4H), 3.50-3.38 (m, 4H), 1.52 (s, 9H); MS (ESI$^+$) m/z 387 (M+H)$^+$.

C) tert-Butyl 4-(2-formylimidazo[1,2-c]pyrimidin-5-yl)piperazine-1-carboxylate

A mixture of tert-butyl 4-(2-(dichloromethyl)imidazo[1,2-c]pyrimidin-5-yl)piperazine-1-carboxylate (1.87 g, 4.84 mmol) and sodium acetate (0.993 g, 12.1 mmol) in EtOH (10 mL) and water (20 mL) was stirred at 50° C. overnight. After cooling to RT, the reaction mixture was diluted with ethyl acetate, washed with saturated aqueous sodium bicarbonate solution followed by saturated aqueous sodium chloride solution, dried with anhydrous sodium sulfate, filtered and concentrated in vacuo. The crude product mixture was purified by a silica gel ISCO 80 g column eluting with 0-10% methanol/DCM over a 15 minute gradient. The appropriate fractions were isolated and concentrated in vacuo to afford the title compound (1.12 g, 69.8% yield) as a solid. $^1$H NMR (400 MHz, CHLOROFORM-d) δ 10.20 (s, 1H), 8.04 (d, J=0.6 Hz, 1H), 7.84 (d, J=6.5 Hz, 1H), 7.27 (dd, J=6.5, 0.8 Hz, 1H), 3.74-3.65 (m, 4H), 3.49-3.40 (m, 4H), 1.57-1.50 (m, 9H); MS (ESI$^+$) m/z 332 (M+H)$^+$.

Example 2

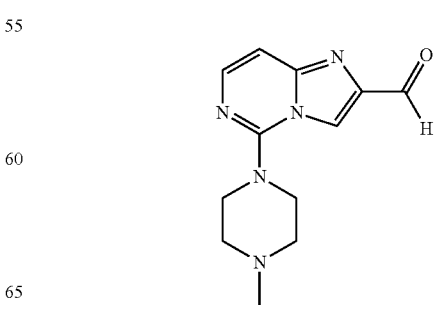

5-(4-Methylpiperazin-1-yl)imidazo[1,2-c]pyrimidine-2-carbaldehyde

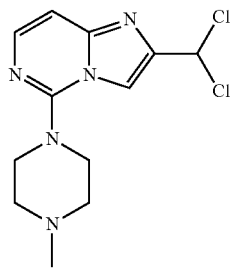 [SMILES: CN1CCN(c2nccc3nc(C(Cl)Cl)cn23)CC1]

A) 2-(Dichloromethyl)-5-(4-methylpiperazin-1-yl)imidazo[1,2-c]pyrimidine

To a solution of 5-chloro-2-(dichloromethyl)imidazo[1,2-c]pyrimidine (134 mg, 0.567 mmol) in THF (2 mL) at rt was added 1-methylpiperazine (0.063 mL, 0.567 mmol) followed by DIPEA (0.119 mL, 0.680 mmol). After stirring at rt 15 min, LCMS showed complete conversion. The reaction mixture was concentrated in vacuo and then purified directly by flash chromatography using an Isco 40 g column eluting with 0-10% MeOH/DCM to give the desired product as an orange oil. $^1$H NMR (400 MHz, CHLOROFORM-d) δ 7.81 (d, J=8 Hz, 1H), 7.63 (s, 1H), 7.22 (d, J=8 Hz, 1H), 6.93 (s, 1H), 3.73-3.70 (m, 4H), 3.10-3.00 (m, 4H), 2.64 (s, 3H); MS (ESI$^+$) m/z 300.0 (M+H)$^+$.

B) 5-(4-Methylpiperazin-1-yl)imidazo[1,2-c]pyrimidine-2-carbaldehyde

A mixture of 2-(dichloromethyl)-5-(4-methylpiperazin-1-yl)imidazo[1,2-c]pyrimidine (50 mg, 0.167 mmol) and sodium acetate (34.2 mg, 0.416 mmol) in EtOH (0.3 mL)/water (0.6 mL) was stirred at rt for 3 h and then at 50° C. overnight. After cooling to rt, the reaction was purified directly by flash chromatography using an Isco 40 g column eluting with 0-20% MeOH/DCM to give the title compound (13 mg, 31.8% yield) as a yellow solid. $^1$H NMR (400 MHz, CHLOROFORM-d) δ 10.19 (s, 1H), 8.03 (s, 1H), 7.83 (d, J=8 Hz, 1H), 7.24 (d, J=8 Hz, 1H), 3.56-3.51 (m, 4H), 2.73-2.71 (m, 4H), 2.48 (s, 3H); MS (ESI$^+$) m/z 246.1 (M+H)$^+$.

Example 3

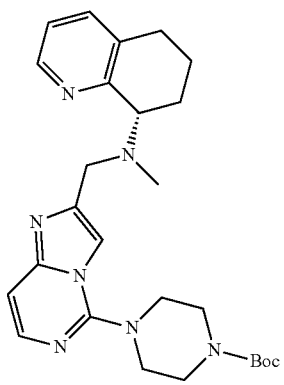 [SMILES: CN(Cc1cn2c(N3CCN(C(=O)OC(C)(C)C)CC3)nccc2n1)[C@H]1CCCc2cccnc21]

(S)-tert-Butyl 4-(2-((methyl(5,6,7,8-tetrahydroquinolin-8-yl)amino)methyl)imidazo[1,2-c]pyrimidin-5-yl)piperazine-1-carboxylate A mixture of tert-butyl 4-(2-formylimidazo[1,2-c]pyrimidin-5-yl)piperazine-1-carboxylate (0.5 g, 1.51 mmol) and (S)—N-methyl-5,6,7,8-tetrahydroquinolin-8-amine (0.269 g, 1.66 mmol) was stirred in DCE (15 mL) and acetic acid (0.15 mL) for 15 minutes. Solid sodium triacetoxyborohydride (0.480 g, 2.26 mmol) was added and the solution was stirred at RT for 16 hours. The reaction mixture was quenched with water, extracted with DCM (3×), washed with saturated aqueous sodium bicarbonate solution followed by saturated aqueous sodium chloride solution, dried with anhydrous sodium sulfate, filtered and concentrated in vacuo. The crude product mixture was purified by a silica gel 80 g ISCO column, eluting with 0-70% (20% NH$_3$/MeOH)/DCM over a 15 min gradient. The appropriate fractions were isolated and concentrated to afford the product (575 mg, 80%) as a solid. $^1$H NMR (400 MHz, CHLOROFORM-d) δ 8.53 (dd, J=4.6, 1.5 Hz, 1H), 7.74-7.65 (m, 2H), 7.38 (dt, J=7.7, 0.7 Hz, 1H), 7.18-7.02 (m, 2H), 4.23-4.04 (m, 1H), 3.95 (s, 2H), 3.67 (q, J=4.6 Hz, 4H), 3.49 (s, 3H), 3.40 (t, J=5.0 Hz, 4H), 2.95-2.63 (m, 2H), 2.40 (s, 3H), 2.24-1.91 (m, 6H), 1.82-1.58 (m, 1H), 1.51 (s, 9H); MS (ESI$^+$) m/z 478.3 (M+H)$^+$.

Example 4

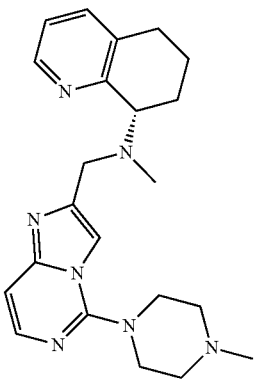 [SMILES: CN1CCN(c2nccc3nc(CN(C)[C@H]4CCCc5cccnc54)cn23)CC1]

(S)—N-Methyl-N-((5-(4-methylpiperazin-1-yl)imidazo[1,2-c]pyrimidin-2-yl)methyl)-5,6,7,8-tetrahydroquinolin-8-amine A mixture of 5-(4-methylpiperazin-1-yl)imidazo[1,2-c]pyrimidine-2-carbaldehyde (13 mg, 0.053 mmol) and (S)—N-methyl-5,6,7,8-tetrahydroquinolin-8-amine (8.60 mg, 0.053 mmol) in DCM (1 mL) was charged with a drop of acetic acid followed by sodium triacetoxyborohydride (14.60 mg, 0.069 mmol). After stirring rt 1 h, LCMS indicated the reaction was complete. The reaction mixture was concentrated in vacuo and the residue was purified directly by prep hplc using a C18 Phen Luna S5 ODS 21.20×100 mm column eluting with 0-100% solvent A/B over a 15 minute gradient (Solvent A: 95% $H_2O$/5% MeCN/ 10 mM $NH_4OAc$; Solvent B: 5% $H_2O$/95% MeCN/10 mM $NH_4OAc$). The product-containing fractions eluted as a broad peak from 4.7-8.7 min. The desired fractions were combined and then lyophilized to give the title compound (12 mg, 58% yield) as a tan solid. $^1H$ NMR (400 MHz, CD3OD) δ 8.48 (d, J=4 Hz, 1H), 7.89 (s, 1H), 7.80 (d, J=8 Hz, 1H), 7.61 (d, J=8 Hz, 1H), 7.28 (dd, J=8, 4 Hz, 1H), 7.14 (d, J=8 Hz, 1H), 4.38-4.34 (m, 1H), 4.12 (d, J=8 Hz, 2H), 3.60-3.52 (m, 4H), 2.92-2.78 (m, 6H), 2.55 (s, 3H), 2.47 (s, 3H), 2.32-2.30 (m, 1H), 2.17-2.07 (m, 2H), 1.96-1.82 (m, 1H); MS ($ESI^+$) m/z 392.2 $(M+H)^+$.

Example 5

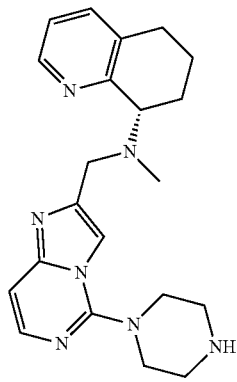 [SMILES: CN(Cc1cn2c(N3CCNCC3)nccc2n1)[C@H]1CCCc2cccnc21]

(S)—N-Methyl-N-((5-(piperazin-1-yl)imidazo[1,2-c] pyrimidin-2-yl)methyl)-5,6,7,8-tetrahydroquinolin-8-amine (S)-tert-Butyl 4-(2-((methyl(5,6,7,8-tetrahydroquinolin-8-yl)amino)methyl)imidazo[1,2-c]pyrimidin-5-yl)piperazine-1-carboxylate (375 mg, 0.785 mmol) was dissolved in DCM and TFA (0.012 mL, 0.151 mmol). The reaction solution was stirred at RT for 2 hours. The solution was concentrated in vacuo. The crude compound was purified via preparative LC/MS using a Waters XBridge C18 column, 19×200 mm; eluting with 0-40% aqueous $CH_3CN$ with 0.1% TFA over a 20 minute gradient. The appropriate fractions were isolated, passed through a PL-$HCO_3$ cartridge and concentrated to afford the product (250 mg, 80%) as a solid. $^1H$ NMR (400 MHz, CHLOROFORM-d) δ 8.54 (d, J=3.5 Hz, 1H), 7.87 (s, 1H), 7.74 (d, J=6.4 Hz, 1H), 7.46-7.37 (m, 1H), 7.22-7.03 (m, 2H), 4.52-4.27 (m, 3H), 3.72-3.52 (m, 4H), 3.28 (d, J=2.8 Hz, 4H), 3.00-2.66 (m, 2H), 2.58 (s, 3H), 2.47-2.21 (m, 1H), 2.21-1.87 (m, 2H), 1.87-1.65 (m, 1H); MS ($ESI^+$) m/z 378.3 (M+H)+.

Example 6

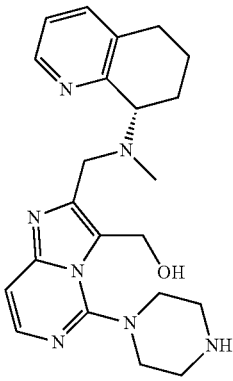 [SMILES: CN(Cc1nc2ccnc(N3CCNCC3)n2c1CO)[C@H]1CCCc2cccnc21]

(S)-(2-((Methyl(5,6,7,8-tetrahydroquinolin-8-yl) amino)methyl)-5-(piperazin-1-yl)imidazo[1,2-c] pyrimidin-3-yl)methanol A) (S)-(9H-Fluoren-9-yl)methyl 4-(2-((methyl(5,6, 7,8-tetrahydroquinolin-8-yl)amino)methyl)imidazo [1,2-c]pyrimidin-5-yl)piperazine-1-carboxylate A flask was charged with (S)—N-methyl-N-((5-(piperazin-1-yl)imidazo[1,2-c]pyrimidin-2-yl)methyl)-5,6,7,8-tetrahydroquinolin-8-amine (120 mg, 0.318 mmol), TEA (0.111 mL, 0.795 mmol) in DCM (5 mL) and 9-fluorenylmethyl chloroformate (90 mg, 0.350 mmol) added slowly to the reaction mixture. The reaction was stirred at RT for 2 hours. The reaction was quenched with methanol and then concentrated in vacuo. The crude product mixture was purified by a C18 Gold 50 g ISCO column eluting with 0-100% aq MeOH with 0.1% TFA over a 15 min gradient. The appropriate fractions were isolated and concentrated in vacuo to afford the product (110 mg, 58% yield) as a solid. $^1H$ NMR (400 MHz, CHLOROFORM-d) δ 8.54 (dd, J=4.6, 1.5 Hz, 1H), 7.80 (d, J=7.5 Hz, 2H), 7.77-7.68 (m, 2H), 7.61 (d, J=7.5 Hz, 2H), 7.51-7.31 (m, 5H), 7.19-7.01 (m, 2H), 4.60-4.45 (m, 2H), 4.30 (t, J=6.5 Hz, 1H), 4.25-4.11 (m, 1H), 4.11-3.90 (m, 2H), 3.70 (br s, 4H), 3.39 (d, J=1.8 Hz, 4H), 3.00-2.59 (m, 3H), 2.49-2.34 (m, 4H), 2.34-1.91 (m, 8H), 1.87-1.61 (m, 1H); MS ($ESI^+$) m/z 600 $(M+H)^+$.

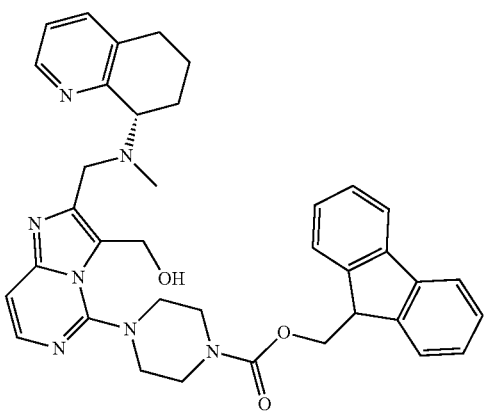 [SMILES: CN(Cc1nc2ccnc(N3CCN(C(=O)OCC4c5ccccc5-c5ccccc54)CC3)n2c1CO)[C@H]1CCCc2cccnc21]

B) (9H-Fluoren-9-yl)methyl (S)-4-(3-(hydroxymethyl)-2-((methyl(5,6,7,8-tetrahydroquinolin-8-yl)amino)methyl)imidazo[1,2-c]pyrimidin-5-yl)piperazine-1-carboxylate A solution of (S)-(9H-fluoren-9-yl)methyl 4-(2-((methyl (5,6,7,8-tetrahydroquinolin-8-yl)amino)methyl)imidazo[1,2-c]pyrimidin-5-yl)piperazine-1-carboxylate (105 mg, 0.175 mmol) in DCE (2 mL) was charged with formaldehyde, 37% aq (0.096 mL, 3.50 mmol) and acetic acid (0.5 mL). Solid sodium triacetoxyborohydride (37.1 mg, 0.175 mmol) was then added. The reaction solution was stirred at 70° C. for 16 hours. The reaction was cooled, quenched with water, and extracted with DCM (3×). The organic layer was washed with saturated aqueous sodium chloride, dried with anhydrous sodium sulfate, and concentrated in vacuo. The crude product mixture was purified using a silica gel ISCO 40 g column, eluting with 0-50% of (20% NH$_3$/MeOH)/DCM over a 15 min gradient. The appropriate fractions were isolated and concentrated in vacuo to afford the product as a solid; MS (ES): m/z=630 (M+H)$^+$.

C) (S)-(2-((Methyl(5,6,7,8-tetrahydroquinolin-8-yl)amino)methyl)-5-(piperazin-1-yl)imidazo[1,2-c]pyrimidin-3-yl)methanol A solution of (S)-(9H-fluoren-9-yl)methyl 4-(3-(hydroxymethyl)-2-((methyl(5,6,7,8-tetrahydroquinolin-8-yl)amino)methyl)imidazo[1,2-c]pyrimidin-5-yl)piperazine-1-carboxylate (36 mg, 0.057 mmol) in DMF (4 mL) was charged with piperidine (113 µl, 1.14 mmol). The reaction was stirred at RT for 15 min. The crude product mixture was purified using a C18 Phen Luna Axia 21.20×250 mm column, eluting with 10-50% aq CH$_3$CN with 0.1% TFA over a 10 min gradient. The desired fractions were combined, passed through a PL-HCO$_3$ cartridge and freeze-dried to afford the product (13 mg, 53% yield) as a solid. $^1$H NMR (400 MHz, METHANOL-d$_4$) δ 8.66-8.28 (m, 1H), 7.78 (d, J=6.2 Hz, 1H), 7.60-7.39 (m, 1H), 7.17 (d, J=6.4 Hz, 2H), 5.21 (d, J=7.9 Hz, 2H), 4.25-3.85 (m, 4H), 3.57-3.22 (m, 8H), 3.12 (t, J=4.6 Hz, 6H), 2.17 (s, 9H); MS (ES): m/z=408.1 (M+H)$^+$.

Example 7

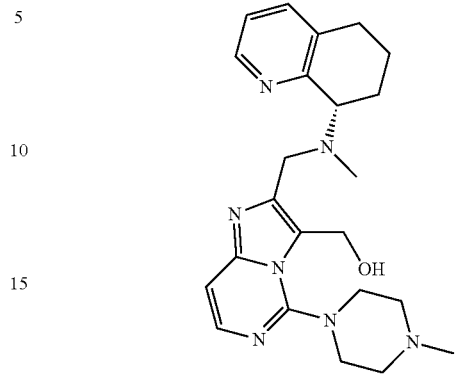

(S)-(2-((Methyl(5,6,7,8-tetrahydroquinolin-8-yl)amino)methyl)-5-(4-methylpiperazin-1-yl)imidazo[1,2-c]pyrimidin-3-yl)methanol A solution of (S)—N-methyl-N-((5-(4-methylpiperazin-1-yl)imidazo[1,2-c]pyrimidin-2-yl)methyl)-5,6,7,8-tetrahydroquinolin-8-amine (40 mg, 0.102 mmol) in DCE (1 mL) was charged with formaldehyde, 37% aq (0.056 mL, 2.043 mmol) and acetic acid (0.5 mL). Solid sodium triacetoxyborohydride (21.65 mg, 0.102 mmol) was then added. After stirring at 60° C. 48 h, the reaction was quenched with saturated aqueous sodium bicarbonate solution and extracted with 20% MeOH/DCM (3×). The pooled organic extracts were concentrated in vacuo. The residue was purified directly by prep hplc using a C18 Phen Luna Axia 21.20×250 mm column eluting with 0-100% solvent A/B over a 30 minute gradient (Solvent A: 95% H$_2$O/5% MeCN/10 mM NH$_4$OAc; Solvent B: 5% H$_2$O/95% MeCN/10 mM NH$_4$OAc). The alcohol product eluted at 16.8 min. The desired fractions were combined and then lyophilized to give the title compound (14 mg, 31% yield) as a white solid. $^1$H NMR (400 MHz, METHANOL-d$_4$) δ 8.42 (d, J=4 Hz, 1H), 7.79 (d, J=4 Hz, 1H), 7.57 (d, J=4, 1 Hz, 1H), 7.25-7.20 (m, 2H), 5.20 (d, J=8 Hz, 2H), 4.24-4.11 (m, 3H), 3.75-3.40 (m, 4H), 3.05-2.78 (m, 6H), 2.52 (s, 3H), 2.33 (s, 3H), 2.35-2.30 (m, 1H), 2.13-2.04 (m, 2H), 1.88-1.72 (m, 1H); MS (ES): m/z=422.3 (M+H)$^+$.

Example 8

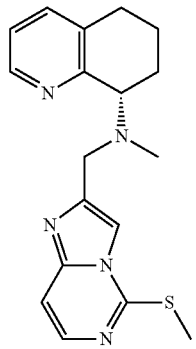 [SMILES: CSc1nccc2nc(CN(C)[C@H]3CCCc4cccnc43)cn12]

(S)—N-Methyl-N-((5-(methylthio)imidazo[1,2-c]
pyrimidin-2-yl)methyl)-5,6,7,8-tetrahydroquinolin-
8-amine

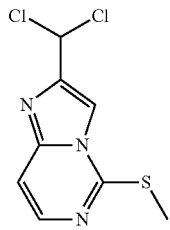

A) 2-(Dichloromethyl)-5-(methylthio)imidazo[1,2-c]
pyrimidine

A clear solution of 2-(methylthio)pyrimidin-4-amine (AstaTech, 150 mg, 1.06 mmol) and 1,1,3-trichloropropan-2-one (Aldrich, 0.17 mL, 1.59 mmol) in DME (1.5 mL) was stirred at 70° C. overnight. Additional 1,1,3-trichloropropan-2-one (0.17 mL, 1.59 mmol) was added and the reaction mixture was stirred at 70° C. for 4 h. DMF (2.0 mL) was added followed by additional 1,1,3-trichloropropan-2-one (0.17 mL, 1.59 mmol). The brown reaction mixture was stirred at 70° C. for 2 h. Additional 1,1,3-trichloropropan-2-one (0.17 mL, 1.59 mmol) was added and heating was continued overnight. The reaction mixture was poured into a separatory funnel containing sat. NaHCO$_3$. The aqueous layer was extracted 3× with CH$_2$Cl2 (extensive emulsion). The organic extracts were washed with 10% LiCl and sat. NaCl and then dried over Na$_2$SO$_4$ together with the emulsion. Concentration in vacuo gave a crude solid which was purified using column chromatography on an ISCO system (330 g column, gradient from 0 to 40% EtOAc/hexanes over 35 min) to give the title compound (45 mg, 17% yield). $^1$H NMR (400 MHz, DMSO-d$_6$) δ 8.01-7.98 (m, 2H), 7.58 (s, 1H), 7.45 (d, J=6.5 Hz, 1H), 2.77 (s, 3H); MS (ESI$^+$) m/z 248.0 (M+H)$^+$.

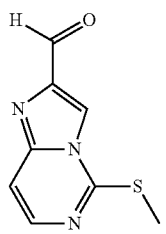

B) 5-(Methylthio)imidazo[1,2-c]pyrimidine-2-carbaldehyde

To a solution of 2-(dichloromethyl)-5-(methylthio)imidazo[1,2-c]pyrimidine (45 mg, 0.18 mmol) in EtOH (1.2 mL) and water (1.6 mL) was added sodium acetate (37 mg, 0.45 mmol). The resulting reaction mixture was stirred overnight at 50° C. The reaction mixture was concentrated at 50° C. under a stream of N$_2$ and then purified directly using column chromatography on an ISCO system (12 g column, gradient from 0 to 10% MeOH/CH$_2$Cl$_2$ over 11 min) to give the title compound (32 mg, 91% yield) as a pale yellow solid. $^1$H NMR (400 MHz, CHLOROFORM-d) δ 10.19 (s, 1H), 8.12 (d, J=0.7 Hz, 1H), 7.95 (d, J=6.5 Hz, 1H), 7.36 (dd, J=6.5, 0.9 Hz, 1H), 2.82 (s, 3H); MS (ESI$^+$) m/z 194.1 (M+H)$^+$.

C) (S)—N-Methyl-N-((5-(methylthio)imidazo[1,2-c]
pyrimidin-2-yl)methyl)-5,6,7,8-tetrahydroquinolin-
8-amine To a solution of (S)—N-methyl-5,6,7,8-tetrahydroquinolin-8-amine (27 mg, 0.17 mmol) and 5-(methylthio)imidazo[1,2-c]pyrimidine-2-carbaldehyde (32 mg, 0.17 mmol) in DCE (1.5 mL) was added 1 drop of AcOH. After stirring for 10 min, sodium triacetoxyborohydride (53 mg, 0.25 mmol) was added. The resulting reaction mixture was stirred for 1.5 h at room temperature, then concentrated under a stream of N$_2$ and purified using column chromatography on an ISCO system (12 g column, gradient from 0 to 8% MeOH/CH$_2$Cl2 over 10 min, then 10 to 20% NH$_3$/MeOH/CH$_2$Cl2 over 5 min) to give the title compound (45 mg, 79% yield) as a colorless oil. $^1$H NMR (400 MHz, DMSO-d$_6$) δ 8.54 (br s, 1H), 7.82 (d, J=6.4 Hz, 1H), 7.69 (br s, 1H), 7.39 (d, J=7.6 Hz, 1H), 7.25 (br s, 1H), 7.09 (dd, J=7.6, 4.8 Hz, 1H), 4.21 (br s, 1H), 4.07 (br s, 2H), 2.93-2.64 (m, 5H), 2.41 (br s, 3H), 2.18 (d, J=3.3 Hz, 1H), 2.11-1.89 (m, 2H), 1.80-1.61 (m, 1H); MS (ESI$^+$) m/z 340.1 (M+H)$^+$.

Example 9

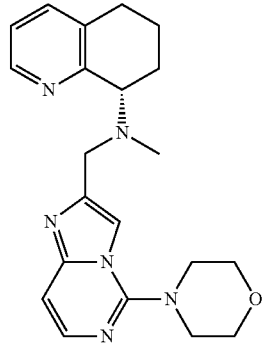 [SMILES: CN(Cc1cn2c(N3CCOCC3)nccc2n1)[C@H]1CCCc2cccnc21]

(S)—N-Methyl-N-((5-morpholinoimidazo[1,2-c]
pyrimidin-2-yl)methyl)-5,6,7,8-tetrahydroquinolin-
8-amine To a microwave vial containing (S)—N-methyl-N-((5-(methylthio)imidazo[1,2-c]pyrimidin-2-yl)methyl)-5,6,7,8-tetrahydroquinolin-8-amine (10 mg, 0.029 mmol) and morpholine (8 μL, 0.09 mmol) in NMP (0.5 mL) was added Et$_3$N (20 μL, 0.15 mmol). The vial was irradiated at 100° C. for 1 h in the microwave. Additional morpholine (100 μL) was added followed by Et$_3$N (100 μL). The reaction mixture was irradiated at 150° C. for 6 h and then stirred at room temperature overnight. Additional morpholine (200 μL) was added and the reaction mixture was irradiated at 180° C. for 8 h, then concentrated under stream of N$_2$ to ~300 μL. The solution was diluted with DMF and purified directly via preparative LC/MS (column: Waters XBridge C18, 19×200 mm, 5 m particles; mobile phase A: 5:95 acetonitrile:water with 10 mM ammonium acetate; mobile phase B: 95:5 acetonitrile:water with 10 mM ammonium acetate; gradient: 0-40% B over 20 minutes, then a 5-minute hold at 100% B; flow: 20 mL/min) to give the title compound (4 mg, 31% yield). $^1$H NMR (500 MHz, DMSO-$d_6$) δ 8.43 (d, J=3.8 Hz, 1H), 7.80-7.65 (m, 2H), 7.49 (d, J=7.4 Hz, 1H), 7.22-7.09 (m, 2H), 4.03-3.88 (m, 3H), 3.83 (br s, 4H), 2.85-2.64 (m, 2H), 2.55 (s, 4H), 2.24 (s, 3H), 1.96 (br s, 3H), 1.65 (d, J=5.6 Hz, 1H); MS (ESI$^+$) m/z 379.2 (M+H)$^+$.

Example 10

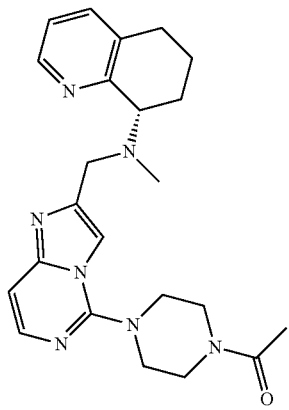 [SMILES: CC(=O)N1CCN(c2nccc3nc(CN(C)[C@H]4CCCc5cccnc54)cn23)CC1]

(S)-1-(4-(2-((Methyl(5,6,7,8-tetrahydroquinolin-8-yl)amino)methyl)imidazo[1,2-c]pyrimidin-5-yl)piperazin-1-yl)ethanone A vial was charged with (S)—N-methyl-N-((5-(piperazin-1-yl)imidazo[1,2-c]pyrimidin-2-yl)methyl)-5,6,7,8-tetrahydroquinolin-8-amine (25 mg, 0.066 mmol), TEA (0.023 mL, 0.166 mmol) in DCM (1 mL) and acetyl chloride (5.18 μl, 0.073 mmol) was added. The reaction was stirred at RT for 2 hours. The reaction solution was removed in vacuo. The crude material was purified via preparative LC/MS using a XBridge C18 column, 19×200 mm; eluting with 10-50% Mobile Phase B (Mobile Phase A: 5:95 acetonitrile:water with 10-mM ammonium acetate; Mobile Phase B: 95:5 acetonitrile:water with 10-mM ammonium acetate) over a 25 minute gradient. The desired fractions were combined and dried via centrifugal evaporation to afford the product (2.3 mg, 53% yield) as a solid. $^1$H NMR (500 MHz, DMSO-$d_6$) δ 8.43 (d, J=4.0 Hz, 1H), 7.87-7.62 (m, 2H), 7.50 (d, J=7.3 Hz, 1H), 7.28-7.01 (m, 2H), 4.01-3.85 (m, 2H), 3.68 (br s, 3H), 3.53-3.25 (m, 2H), 3.25-2.93 (m, 1H), 2.93-2.60 (m, 3H), 2.22 (s, 3H), 2.07 (s, 3H), 2.03-1.57 (m, 6H); MS (ESI$^+$) m/z 420.3 (M+H)$^+$.

Example 11

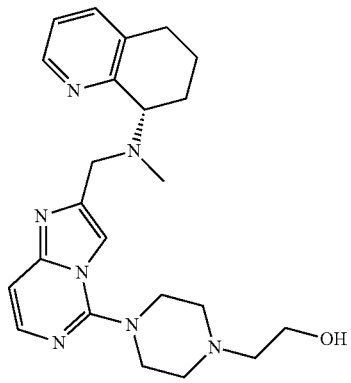 [SMILES: CN(Cc1cn2c(N3CCN(CCO)CC3)nccc2n1)[C@H]1CCCc2cccnc21]

(S)-2-(4-(2-((Methyl(5,6,7,8-tetrahydroquinolin-8-yl)amino)methyl)imidazo[1,2-c]pyrimidin-5-yl)piperazin-1-yl)ethanol In a 2D vial was added (S)—N-methyl-N-((5-(piperazin-1-yl)imidazo[1,2-c]pyrimidin-2-yl)methyl)-5,6,7,8-tetrahydroquinolin-8-amine (20 mg, 0.053 mmol), potassium carbonate (7.32 mg, 0.053 mmol) and 2-bromoethanol (6.62 mg, 0.053 mmol) in DMF (2 mL). The reaction solution was heated to 65° C. for 6 hours. The crude material was purified via preparative LC/MS using a XBridge C18 column, 19×200 mm; eluting with 0-50% Mobile Phase A to B (Mobile Phase A: 5:95 acetonitrile:water with 10-mM ammonium acetate; Mobile Phase B: 95:5 acetonitrile:water with 10-mM ammonium acetate) over a 25 minute gradient. The desired fractions were combined and dried via centrifugal evaporation to afford the product (7 mg, 30% yield) as a solid. $^1$H NMR (500 MHz, DMSO-$d_6$) δ 8.42 (d, J=3.8 Hz, 1H), 7.73-7.63 (m, 2H), 7.49 (d, J=7.5 Hz, 1H), 7.17 (dd, J=7.5, 4.8 Hz, 1H), 7.10 (d, J=6.3 Hz, 1H), 4.04-3.83 (m, 3H), 3.61-3.52 (m, 1H), 3.36 (br s, 2H), 2.93-2.73 (m, 2H), 2.72-2.62 (m, 5H), 2.55 (m, 2H), 2.22 (s, 3H), 2.05-1.57 (m, 6H); MS (ESI$^+$) m/z 422.3 (M+H)+.

Example 12

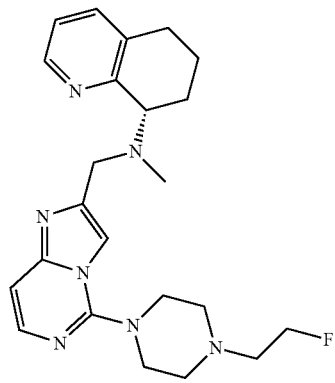 [SMILES: CN(Cc1cn2c(N3CCN(CCF)CC3)nccc2n1)[C@H]1CCCc2cccnc21]

(S)—N-((5-(4-(2-Fluoroethyl)piperazin-1-yl)imidazo[1,2-c]pyrimidin-2-yl)methyl)-N-methyl-5,6,7,8-tetrahydroquinolin-8-amine In a 2D vial was added (S)—N-methyl-N-((5-(piperazin-1-yl)imidazo[1,2-c]pyrimidin-2-yl)methyl)-5,6,7,8-tetrahydroquinolin-8-amine (20 mg, 0.053 mmol), potassium carbonate (7.32 mg, 0.053 mmol) and 1-bromo-2-fluoroethane (7.40 mg, 0.058 mmol) in acetonitrile (2 mL). The reaction solution was heated to 65° C. for 6 hrs. The reaction was filtered and the filtrate concentrated in vacuo. The residue was dissolved in DMF (2 mL) for purification. The crude product mixture was purified by preparative LC/MS using a XBridge C18 column, 19×200 mm; eluting with 20-60% Mobile Phase A to B (Mobile Phase A: 5:95 acetonitrile:water with 10-mM ammonium acetate; Mobile Phase B: 95:5 acetonitrile:water with 10-mM ammonium acetate) over a 25 minute gradient. The desired fractions were combined and dried via centrifugal evaporation to afford the product (7.5 mg, 33% yield) as a solid. $^1$H NMR (500 MHz, DMSO-d$_6$) δ 8.41 (d, J=3.9 Hz, 1H), 7.74-7.64 (m, 2H), 7.49 (d, J=7.3 Hz, 1H), 7.29-7.03 (m, 2H), 4.69-4.47 (m, 2H), 4.04-3.75 (m, 3H), 3.58-3.30 (m, 2H), 2.83-2.59 (m, 8H), 2.21 (s, 3H), 2.03-1.43 (m, 5H); MS (ESI$^+$) m/z 424.3 (M+H)$^+$.

Example 13

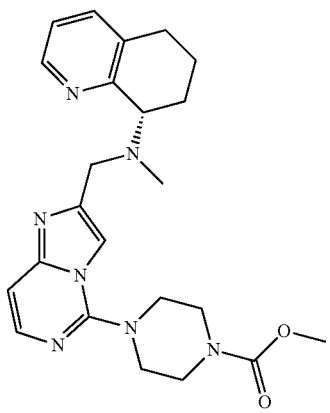 [SMILES: COC(=O)N1CCN(c2nccc3nc(CN(C)[C@H]4CCCc5cccnc54)cn23)CC1]

(S)-Methyl 4-(2-((methyl(5,6,7,8-tetrahydroquinolin-8-yl)amino)methyl)imidazo[1,2-c]pyrimidin-5-yl)piperazine-1-carboxylate A 2D vial was charged with (S)—N-methyl-N-((5-(piperazin-1-yl)imidazo[1,2-c]pyrimidin-2-yl)methyl)-5,6,7,8-tetrahydroquinolin-8-amine (25 mg, 0.066 mmol), TEA (0.023 mL, 0.166 mmol) in DCM (1 mL) and methyl carbonochloridate (6.88 mg, 0.073 mmol) was added. The reaction was stirred at RT for 2 hours. The crude material was purified via preparative LC/MS using a XBridge C18 column, 19×200 mm; eluting with 0-50% Mobile Phase A to B (Mobile Phase A: 5:95 acetonitrile:water with 10-mM ammonium acetate; Mobile Phase B: 95:5 acetonitrile:water with 10-mM ammonium acetate) over a 25 minute gradient. The desired fractions were combined and dried via centrifugal evaporation to afford the product (5 mg, 17% yield) as a solid. $^1$H NMR (500 MHz, DMSO-d$_6$) δ 8.53 (d, J=4.1 Hz, 1H), 8.04-7.89 (m, 1H), 7.83 (d, J=6.4 Hz, 1H), 7.69 (d, J=7.7 Hz, 1H), 7.38 (dd, J=7.6, 4.7 Hz, 1H), 7.26 (d, J=6.5 Hz, 1H), 4.72 (d, J=5.6 Hz, 1H), 4.57-4.33 (m, 2H), 4.22-3.58 (m, 2H), 3.40 (br s, 4H), 2.97-2.71 (m, 6H), 2.59-2.35 (m, 7H), 2.17-2.00 (m, 2H), 1.76 (d, J=9.7 Hz, 1H); MS (ESI$^+$) m/z 436.3 (M+H)$^+$.

Example 14

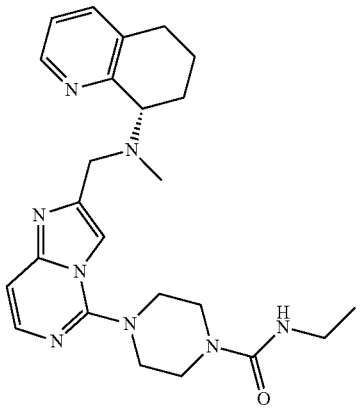 [SMILES: CCNC(=O)N1CCN(c2nccc3nc(CN(C)[C@H]4CCCc5cccnc54)cn23)CC1]

(S)—N-ethyl-4-(2-((methyl(5,6,7,8-tetrahydroquinolin-8-yl)amino)methyl)imidazo[1,2-c]pyrimidin-5-yl)piperazine-1-carboxamide A vial was charged with (S)—N-methyl-N-((5-(piperazin-1-yl)imidazo[1,2-c]pyrimidin-2-yl)methyl)-5,6,7,8-tetrahydroquinolin-8-amine (20 mg, 0.053 mmol) in DCM (1 mL) and isocyanatoethane (4.14 mg, 0.058 mmol) added slowly. The reaction was stirred at RT for 2 hours. The reaction solution was concentrated in vacuo and dissolved in DMF for purification. The crude material was purified via preparative LC/MS using a XBridge C18 column, 19×200 mm; eluting with 0-100% Mobile Phase A to B (Mobile Phase A: 5:95 acetonitrile:water with 10-mM ammonium acetate; Mobile Phase B: 95:5 acetonitrile:water with 10-mM ammonium acetate) over a 25 minute gradient. The desired fractions were combined and dried via centrifugal evaporation to afford the product (24.8 mg, 100% yield) as a solid. $^1$H NMR (500 MHz, DMSO-d$_6$) δ 8.44 (d, J=4.1 Hz, 1H), 7.86-7.66 (m, 2H), 7.52 (d, J=7.5 Hz, 1H), 7.25-7.05 (m, 2H), 6.64 (t, J=5.1 Hz, 1H), 4.16-3.83 (m, 2H), 3.58-3.01 (m, 4H), 2.89-2.61 (m, 2H), 2.53 (d, J=19.5 Hz, 6H), 2.42-1.59 (m, 8H), 1.04 (t, J=7.1 Hz, 3H); MS (ESI$^+$) m/z 449.3 (M+H)+.

Example 15

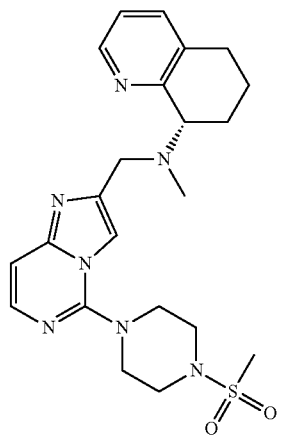 [SMILES: CN(Cc1cn2c(N3CCN(S(C)(=O)=O)CC3)nccc2n1)[C@H]1CCCc2cccnc21]

(S)—N-Methyl-N-((5-(4-(methylsulfonyl)piperazin-1-yl)imidazo[1,2-c]pyrimidin-2-yl)methyl)-5,6,7,8-tetrahydroquinolin-8-amine A vial was charged with (S)—N-methyl-N-((5-(piperazin-1-yl)imidazo[1,2-c]pyrimidin-2-yl)methyl)-5,6,7,8-tetrahydroquinolin-8-amine (20 mg, 0.053 mmol) in DCM (1 mL) and methanesulfonyl chloride (6.68 mg, 0.058 mmol) added slowly. The reaction was stirred at RT for 2 hours. The reaction solution was removed in vacuo and the crude residue was purified by preparative LC/MS using a XBridge C18 column, 19×200 mm; eluting with 0-50% Mobile Phase A to B (Mobile Phase A: 5:95 acetonitrile:water with 10-mM ammonium acetate; Mobile Phase B: 95:5 acetonitrile:water with 10-mM ammonium acetate) over a 17 minute gradient. The desired fractions were combined and dried via centrifugal evaporation to afford the product (11.1 mg, 45.4% yield) as a solid. $^1$H NMR (500 MHz, DMSO-$d_6$) δ 8.48 (br s, 1H), 7.78 (d, J=6.1 Hz, 2H), 7.60 (br s, 1H), 7.23 (d, J=6.1 Hz, 2H), 4.54-4.04 (m, 1H), 3.91 (s, 2H), 3.56-3.45 (m, 1H), 3.44-3.27 (m, 2H), 3.17 (s, 3H), 2.98 (s, 3H), 2.76 (br s, 6H), 2.12-1.62 (m, 5H); MS (ESI$^+$) m/z 456.2 (M+H)$^+$.

Example 16

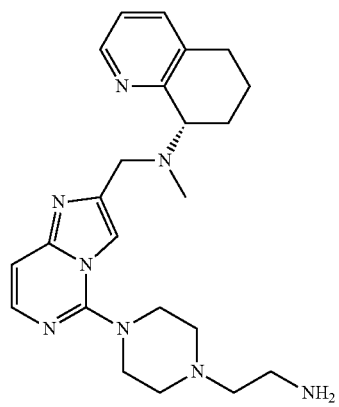 [SMILES: CN(Cc1cn2c(N3CCN(CCN)CC3)nccc2n1)[C@H]1CCCc2cccnc21]

(S)—N-((5-(4-(2-Aminoethyl)piperazin-1-yl)imidazo[1,2-c]pyrimidin-2-yl)methyl)-N-methyl-5,6,7,8-tetrahydroquinolin-8-amine In a 2D vial was added (S)—N-methyl-N-((5-(piperazin-1-yl)imidazo[1,2-c]pyrimidin-2-yl)methyl)-5,6,7,8-tetrahydroquinolin-8-amine (23 mg, 0.061 mmol), potassium carbonate (8.42 mg, 0.061 mmol) and tert-butyl (2-bromoethyl)carbamate (13.65 mg, 0.061 mmol) in DMF (2 mL). The reaction solution was heated to 65° C. for 16 hours. The reaction was filtered, and the filtrate concentrated in vacuo. The above mixture was dissolved in DCM (5 mL) and TFA (0.5 mL). The reaction solution was stirred at RT for 1 hour, then solution concentrated in vacuo. The crude product mixture was purified by preparative LC/MS using a LUNA Phenomenex column, 30×100 mm; eluting with 0-60% Mobile Phase A to B (Mobile Phase A: 5:95 acetonitrile:water with 0.1% TFA; Mobile Phase B: 95:5 acetonitrile:water with 0.1% TFA) over a 17 minute gradient. The desired fractions were combined, passed through a PL-HCO$_3$ cartridge and freeze-dried to afford the product (5 mg, 19% yield) as a solid. $^1$H NMR (400 MHz, CHLOROFORM-d) δ 8.55 (d, J=3.3 Hz, 1H), 7.71 (d, J=6.4 Hz, 1H), 7.55 (s, 1H), 7.41 (d, J=7.5 Hz, 1H), 7.21-7.06 (m, 2H), 4.15 (dd, J=8.7, 6.1 Hz, 1H), 3.96 (d, J=5.0 Hz, 2H), 3.54-3.38 (m, 4H), 3.00 (t, J=6.0 Hz, 2H), 2.77-2.60 (m, 8H), 2.34-2.26 (m, 3H), 2.21-1.87 (m, 4H); MS (ESI$^+$) m/z 421.2 (M+H)$^+$.

Example 17

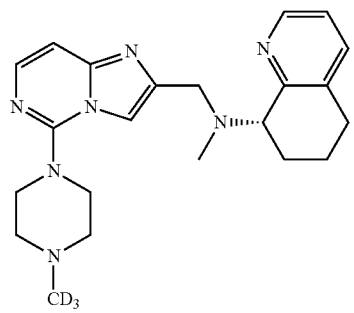 [SMILES: [2H]C([2H])([2H])N1CCN(c2nccc3nc(CN(C)[C@H]4CCCc5cccnc54)cn23)CC1]

(S)—N-Methyl-N-((5-(4-(methyl-$d_3$)piperazin-1-yl)imidazo[1,2-c]pyrimidin-2-yl)methyl)-5,6,7,8-tetrahydroquinolin-8-amine

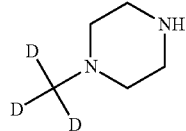

A) 1-(Methyl-$d_3$)piperazine. 2 TFA salt tert-Butyl piperazine-1-carboxylate (1.27 g, 6.82 mmol) and potassium carbonate (0.942 g, 6.82 mmol) were stirred at rt in DMF (5 mL). Iodomethane-$d_3$ (0.646 mL, 6.82 mmol) was added and the resulting reaction mixture was continue stirred at rt overnight. An aliquot showed the desired material by LC/MS (M+H)+204.1. The reaction mixture was quenched with 10% aq LiCl and the solution extracted with ethyl acetate 3×. The combined organic extracts were washed 3× with 10% aq LiCl. The organic fraction was dried with anhydrous sodium sulfate, filtered and the filtrate concentrated in vacuo. The residue was dissolved in DCM (5 mL) and then treated with 5 ml of TFA at rt. The reaction mixture was stirred 1 h at rt and then concentrated in vacuo. The residue was further dried under high vacuum to afford the desired solid product (1.0 gm, 42% yield) as a 2.TFA salt. $^1$H NMR (400 MHz, DMSO-$d_6$) δ 3.36-3.25 (m, 4H), 2.39-2.24 (m, 4H).

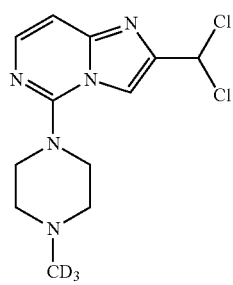 [SMILES: [2H]C([2H])([2H])N1CCN(c2nccc3nc(C(Cl)Cl)cn23)CC1]

B) 2-(Dichloromethyl)-5-(4-(methyl-d₃)piperazin-1-yl)imidazo[1,2-c]pyrimidine To a solution of 1-(methyl-d₃)piperazine. 2 TFA salt (0.087 g, 0.846 mmol) and N,N-diisopropylethylamine (0.147 mL, 0.846 mmol) in 0.5 ml of THF was added 5-chloro-2-(dichloromethyl)imidazo[1,2-c]pyrimidine (0.2 g, 0.846 mmol) in 0.5 ml of THF at rt. The reaction mixture was stirred at rt for 15 h. The reaction mixture was concentrated in vacuo and the residue wet loaded with MeOH on to a C-18 50 gm ISCO column, eluting 0-100% aq CH₃CN with 0.1% TFA over a 13 minute gradient. The appropriate fractions were isolated and quenched with sat aq NaHCO₃. The solution was extracted with DCM 3×, the combined organic fractions were dried with anhydrous sodium sulfate, filtered and the filtrate concentrated in vacuo. The residue was further dried under high vacuum to afford the desire product (0.030 gm, 12% yield) as a solid. $^1$H NMR (400 MHz, CHLOROFORM-d) δ 8.03 (d, J=0.6 Hz, 1H), 7.87-7.74 (m, 1H), 7.37-7.13 (m, 1H), 6.91 (d, J=0.5 Hz, 1H), 3.62-3.40 (m, 4H), 2.80-2.52 (m, 4H); MS (ESI$^+$) m/z 303.1 (M+H)$^+$.

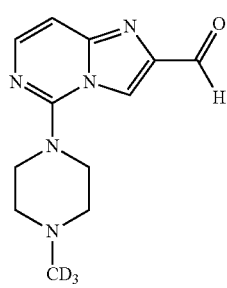 [SMILES: [2H]C([2H])([2H])N1CCN(c2nccc3nc(C=O)cn23)CC1]

C) 5-(4-(Methyl-d₃)piperazin-1-yl)imidazo[1,2-c]pyrimidine-2-carbaldehyde 2-(Dichloromethyl)-5-(4-(methyl-d₃)piperazin-1-yl)imidazo[1,2-c]pyrimidine (0.025 g, 0.082 mmol) was dissolved in ethanol (0.2 mL, 0.082 mmol) and water (0.4 ml) and the resulting solution was then treated with sodium acetate (0.017 g, 0.206 mmol) at rt. The resulting reaction mixture was then heated to 50° C. with stirring overnight. The reaction mixture was diluted with sat aq NaCl and the solution extracted with DCM 3×. The combined organic extracts were dried with anhydrous sodium sulfate, filtered and the filtrate concentrated in vacuo to afford the desired product (0.020 gm, 98% yield) as an oil. $^1$H NMR (400 MHz, CHLOROFORM-d) δ 10.20 (s, 1H), 8.04 (d, J=0.7 Hz, 1H), 7.84 (d, J=6.5 Hz, 1H), 7.24 (dd, J=6.5, 0.9 Hz, 1H), 3.62-3.42 (m, 4H), 2.73-2.56 (m, 4H); MS (ESI$^+$) m/z 249.1 (M+H)$^+$.

D) (S)—N-Methyl-N-((5-(4-(methyl-d₃)piperazin-1-yl)imidazo[1,2-c]pyrimidin-2-yl)methyl)-5,6,7,8-tetrahydroquinolin-8-amine 5-(4-(Methyl-d₃)piperazin-1-yl)imidazo[1,2-c]pyrimidine-2-carbaldehyde (0.02 g, 0.081 mmol) and (S)—N-methyl-5,6,7,8-tetrahydroquinolin-8-amine (0.013 g, 0.081 mmol) were dissolved in 1/1 DCE (0.5 mL)/2-propanol (0.5 mL) along with 2 drops of acetic acid at rt. The reaction mixture was stirred at rt for 1 h. Sodium triacetoxyborohydride (0.017 g, 0.081 mmol) was added and the resulting reaction mixture was stirred at rt for 12 h. LC/MS indicated desired product. The reaction mixture was concentrated in vacuo and the residue dissolved in 1 ml of 1/1 1N HCl/MeOH. The solution was wet loaded on to a C-18 ISCO 50 gm gold column eluting 0-70% aq CH₃CN with 0.1% TFA over a 15 minute gradient. The appropriate fractions were isolated and quenched with 10% aq NaHCO₃. The solution was extracted with DCM 3×, the combined organic extracts were dried with anhydrous sodium sulfate, filtered and the filtrate concentrated in vacuo. The residue was dissolved in aq CH₃CN and freeze dried to afford the desired product (0.025 gm, 76% yield) as a solid. $^1$H NMR (400 MHz, METHANOL-d₄) δ 8.50-8.31 (m, 1H), 7.88 (d, J=0.6 Hz, 1H), 7.76 (d, J=6.4 Hz, 1H), 7.54 (dt, J=7.8, 0.7 Hz, 1H), 7.20 (dd, J=7.7, 4.6 Hz, 1H), 7.09 (dd, J=6.4, 0.7 Hz, 1H), 4.08 (dd, J=8.6, 5.6 Hz, 1H), 3.90-3.76 (m, 2H), 3.64-3.47 (m, 4H), 2.97-2.81 (m, 2H), 2.75 (t, J=4.6 Hz, 4H), 2.35 (s, 3H), 2.21-1.96 (m, 3H), 1.78-1.65 (m, 1H); MS (ESI$^+$) m/z 395.2 (M+H)$^+$.

Examples 18-69

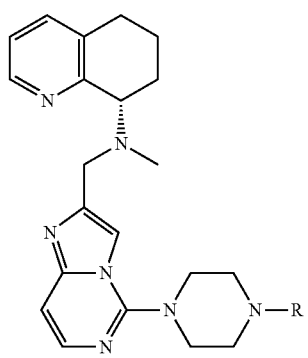

The following examples were prepared according to the procedures described for the synthesis of Examples 10-16:

| Ex. No. | Structure | Name | LC/MS (M + H)+ |
|---|---|---|---|
| 18 | 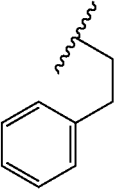 [SMILES: *CCc1ccccc1] | (S)-N-methyl-N-({5-[4-(2-phenylethyl)piperazin-1-yl]imidazo[1,2-c]pyrimidin-2-yl}methyl)-5,6,7,8-tetrahydroquinolin-8-amine | 482.3 |
| 19 | 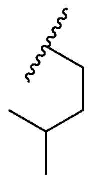 [SMILES: *CCC(C)C] | (S)-N-methyl-N-({5-[4-(3-methylbutyl)piperazin-1-yl]imidazo[1,2-c]pyrimidin-2-yl}methyl)-5,6,7,8-tetrahydroquinolin-8-amine | 448.3 |
| 20 | 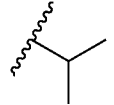 | (S)-N-methyl-N-({5-[4-(propan-2-yl)piperazin-1-yl]imidazo[1,2-c]pyrimidin-2-yl}methyl)-5,6,7,8-tetrahydroquinolin-8-amine | 420.3 |
| 21 | 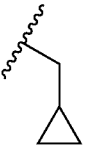 [SMILES: *CC1CC1] | (8S)-N-({5-[4-(cyclopropylmethyl)piperazin-1-yl]imidazo[1,2-c]pyrimidin-2-yl}methyl)-N-methyl-5,6,7,8-tetrahydroquinolin-8-amine | 432.2 |
| 22 | 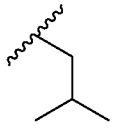 [SMILES: *CC(C)C] | (S)-N-methyl-N-({5-[4-(2-methylpropyl)piperazin-1-yl]imidazo[1,2-c]pyrimidin-2-yl}methyl)-5,6,7,8-tetrahydroquinolin-8-amine | 434.4 |
| 23 | 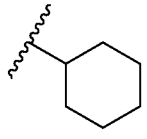 [SMILES: *C1CCCCC1] | (S)-N-{[5-(4-cyclohexylpiperazin-1-yl)imidazo[1,2-c]pyrimidin-2-yl]methyl}-N-methyl-5,6,7,8-tetrahydroquinolin-8-amine | 460.4 |
| 24 | 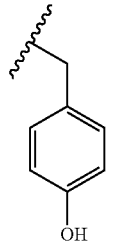 [SMILES: *Cc1ccc(O)cc1] | 4-({4-[2-({methyl[(S)-5,6,7,8-tetrahydroquinolin-8-yl]amino}methyl)imidazo[1,2-c]pyrimidin-5-yl]piperazin-1-yl}methyl)phenol | 484.1 |
| 25 | 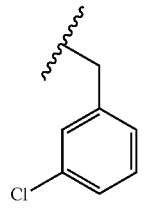 [SMILES: *Cc1cccc(Cl)c1] | (S)-N-[(5-{4-[(3-chlorophenyl)methyl]piperazin-1-yl}imidazo[1,2-c]pyrimidin-2-yl)methyl]-N-methyl-5,6,7,8-tetrahydroquinolin-8-amine | 502.2 |

-continued

| Ex. No. | Structure | Name | LC/MS (M + H)+ |
|---|---|---|---|
| 26 | 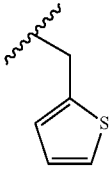 | (S)-N-methyl-N-({5-[4-(thiophen-2-ylmethyl)piperazin-1-yl]imidazo[1,2-c]pyrimidin-2-yl}methyl)-5,6,7,8-tetrahydroquinolin-8-amine | 474.3 |
| 27 | 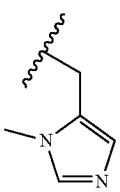 [SMILES: *Cc1cncn1C] | (S)-N-methyl-N-[(5-{4-[(1-methyl-1H-imidazol-5-yl)methyl]piperazin-1-yl}imidazo[1,2-c]pyrimidin-2-yl)methyl]-5,6,7,8-tetrahydroquinolin-8-amine | 472.4 |
| 28 | 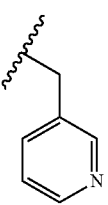 | (S)-N-methyl-N-({5-[4-(pyridin-3-ylmethyl)piperazin-1-yl]imidazo[1,2-c]pyrimidin-2-yl}-5,6,7,8-tetrahydroquinolin-8-amine | 469.2 |
| 29 | 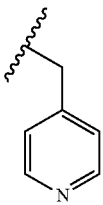 [SMILES: *Cc1ccncc1] | (S)-N-methyl-N-({5-[4-(pyridin-4-ylmethyl)piperazin-1-yl]imidazo[1,2-c]pyrimidin-2-yl}methyl)-5,6,7,8-tetrahydroquinolin-8-amine | 469.4 |
| 30 | 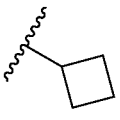 [SMILES: *C1CCC1] | (S)-N-{[5-(4-cyclobutylpiperazin-1-yl)imidazo[1,2-c]pyrimidin-2-yl]methyl}-N-methyl-5,6,7,8-tetrahydroquinolin-8-amine | 432.2 |
| 31 | 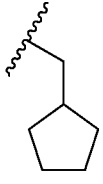 | (S)-N-({5-[4-(cyclopentylmethyl)piperazin-1-yl]imidazo[1,2-c]pyrimidin-2-yl}methyl)-N-methyl-5,6,7,8-tetrahydroquinolin-8-amine | 460.2 |
| 32 | 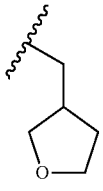 | (S)-N-methyl-N-({5-[4-(oxolan-3-ylmethyl)piperazin-1-yl]imidazo[1,2-c]pyrimidin-2-yl}methyl)-5,6,7,8-tetrahydroquinolin-8-amine | 462.4 |
| 33 | 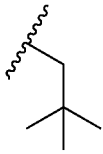 | (S)-N-({5-[4-(2,2-dimethylpropyl)piperazin-1-yl]imidazo[1,2-c]pyrimidin-2-yl}methyl)-N-methyl-5,6,7,8-tetrahydroquinolin-8-amine | 448.3 |

-continued

| Ex. No. | Structure | Name | LC/MS (M + H)+ |
|---|---|---|---|
| 34 | 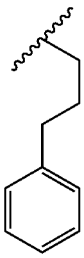 [SMILES: *CCCc1ccccc1] | (S)-N-methyl-N-({5-[4-(3-phenylpropyl)piperazin-1-yl]imidazo[1,2-c]pyrimidin-2-yl}methyl)-5,6,7,8-tetrahydroquinolin-8-amine | 496.3 |
| 35 | 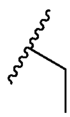 | (S)-N-{[5-(4-ethylpiperazin-1-yl)imidazo[1,2-c]pyrimidin-2-yl]methyl}-N-methyl-5,6,7,8-tetrahydroquinolin-8-amine | 406.2 |
| 36 | 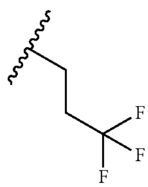 [SMILES: *CCC(F)(F)F] | (S)-N-methyl-N-({5-[4-(3,3,3-trifluoropropyl)piperazin-1-yl]imidazo[1,2-c]pyrimidin-2-yl}methyl)-5,6,7,8-tetrahydroquinolin-8-amine | 474.3 |
| 37 | 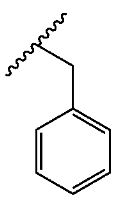 [SMILES: *Cc1ccccc1] | (S)-N-{[5-(4-benzylpiperazin-1-yl)imidazo[1,2-c]pyrimidin-2-yl]methyl}-N-methyl-5,6,7,8-tetrahydroquinolin-8-amine | 468.3 |
| 38 | 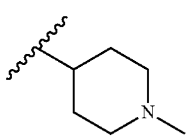 [SMILES: *C1CCN(C)CC1] | (S)-N-methyl-N-({5-[4-(1-methylpiperidin-4-yl)piperazin-1-yl]imidazo[1,2-c]pyrimidin-2-yl}methyl)-5,6,7,8-tetrahydroquinolin-8-amine | 475.4 |
| 39 | 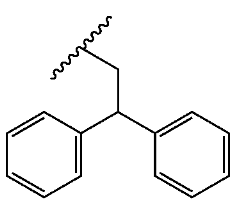 [SMILES: *CC(c1ccccc1)c1ccccc1] | (S)-N-({5-[4-(2,2-diphenylethyl)piperazin-1-yl]imidazo[1,2-c]pyrimidin-2-yl}methyl)-N-methyl-5,6,7,8-tetrahydroquinolin-8-amine | 558.3 |
| 40 | 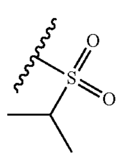 | (S)-N-methyl-N-({5-[4-(propane-2-sulfonyl)piperazin-1-yl]imidazo[1,2-c]pyrimidin-2-yl}methyl)-5,6,7,8-tetrahydroquinolin-8-amine | 484.0 |
| 41 | 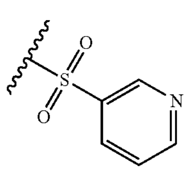 [SMILES: *S(=O)(=O)c1cccnc1] | (S)-N-methyl-N-({5-[4-(pyridine-3-sulfonyl)piperazin-1-yl]imidazo[1,2-c]pyrimidin-2-yl}methyl)-5,6,7,8-tetrahydroquinolin-8-amine | 519.0 |

-continued

| Ex. No. | Structure | Name | LC/MS (M + H)+ |
|---|---|---|---|
| 42 | 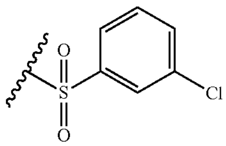 [SMILES: *S(=O)(=O)c1cccc(Cl)c1] | (S)-N-({5-[4-(3-chlorobenzenesulfonyl)piperazin-1-yl]imidazo[1,2-c]pyrimidin-2-yl}methyl)-N-methyl-5,6,7,8-tetrahydroquinolin-8-amine | 552.3 |
| 43 | 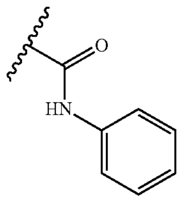 [SMILES: *C(=O)Nc1ccccc1] | 4-[2-({methyl[(S)-5,6,7,8-tetrahydroquinolin-8-yl]amino}methyl)imidazo[1,2-c]pyrimidin-5-yl]-N-phenylpiperazine-1-carboxamide | 497.2 |
| 44 | 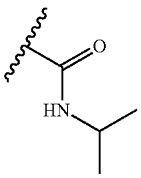 [SMILES: *C(=O)NC(C)C] | 4-[2-({methyl[(S)-5,6,7,8-tetrahydroquinolin-8-yl]amino}methyl)imidazo[1,2-c]pyrimidin-5-yl]-N-(propan-2-yl)piperazine-1-carboxamide | 463.1 |
| 45 | 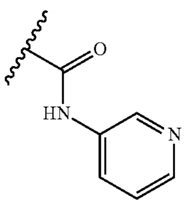 [SMILES: *C(=O)Nc1cccnc1] | 4-[2-({methyl[(S)-5,6,7,8-tetrahydroquinolin-8-yl]amino}methyl)imidazo[1,2-c]pyrimidin-5-yl]-N-(pyridin-3-yl)piperazine-1-carboxamide | 498.0 |
| 46 | 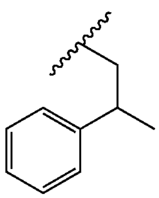 [SMILES: *CC(C)c1ccccc1] | (S)-N-methyl-N-({5-[4-(2-phenylpropyl)piperazin-1-yl]imidazo[1,2-c]pyrimidin-2-yl}methyl)-5,6,7,8-tetrahydroquinolin-8-amine | 496.4 |
| 47 | 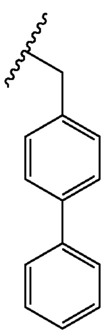 [SMILES: *Cc1ccc(-c2ccccc2)cc1] | (S)-N-methyl-N-[(5-{4-[(4-phenylphenyl)methyl]piperazin-1-yl}imidazo[1,2-c]pyrimidin-2-yl)methyl]-5,6,7,8-tetrahydroquinolin-8-amine | 544.1 |
| 48 | 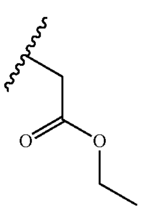 [SMILES: *CC(=O)OCC] | ethyl 2-{4-[2-({methyl[(S)-5,6,7,8-tetrahydroquinolin-8-yl]amino}methyl)imidazo[1,2-c]pyrimidin-5-yl]piperazin-1-yl}acetate | 464.1 |

-continued

| Ex. No. | Structure | Name | LC/MS (M + H)+ |
|---|---|---|---|
| 49 | *imidazole CH2* | (S)-N-({5-[4-(1H-imidazol-2-ylmethyl)piperazin-1-yl]imidazo[1,2-c]pyrimidin-2-yl}methyl)-N-methyl-5,6,7,8-tetrahydroquinolin-8-amine | 458.1 |
| 50 | *CH2COOH* | 2-{4-[2-({methyl[(S)-5,6,7,8-tetrahydroquinolin-8-yl]amino}methyl)imidazo[1,2-c]pyrimidin-5-yl]piperazin-1-yl}acetic acid | 436.1 |
| 51 | *N-methylimidazole CH2* | (S)-N-methyl-N-[(5-{4-[(1-methyl-1H-imidazol-2-yl)methyl]piperazin-1-yl}imidazo[1,2-c]pyrimidin-2-yl)methyl]-5,6,7,8-tetrahydroquinolin-8-amine | 472.4 |
| 52 | *3-methylphenyl CH2* | (S)-N-methyl-N-[(5-{4-[(3-methylphenyl)methyl]piperazin-1-yl}imidazo[1,2-c]pyrimidin-2-yl)methyl]-5,6,7,8-tetrahydroquinolin-8-amine | 482.4 |
| 53 | *4-methylphenyl CH2* | (S)-N-methyl-N-[(5-{4-[(4-methylphenyl)methyl]piperazin-1-yl}imidazo[1,2-c]pyrimidin-2-yl)methyl]-5,6,7,8-tetrahydroquinolin-8-amine | 482.1 |
| 54 | *furan-2-yl CH2* | (S)-N-({5-[4-(furan-2-ylmethyl)piperazin-1-yl]imidazo[1,2-c]pyrimidin-2-yl}methyl)-N-methyl-5,6,7,8-tetrahydroquinolin-8-amine | 458.3 |
| 55 | *pyridin-2-yl CH2* | (S)-N-methyl-N-({5-[4-(pyridin-2-ylmethyl)piperazin-1-yl]imidazo[1,2-c]pyrimidin-2-yl}methyl)-5,6,7,8-tetrahydroquinolin-8-amine | 469.1 |
| 56 | *N-methylpyrrol-2-yl CH2* | (S)-N-methyl-N-[(5-{4-[(1-methyl-1H-pyrrol-2-yl)methyl]piperazin-1-yl}imidazo[1,2-c]pyrimidin-2-yl)methyl]-5,6,7,8-tetrahydroquinolin-8-amine | 471.4 |

-continued

| Ex. No. | Structure | Name | LC/MS (M + H)+ |
|---|---|---|---|
| 57 | 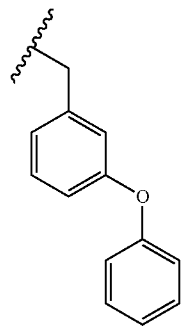 [SMILES: *Cc1cccc(Oc2ccccc2)c1] | (8S)-N-methyl-N-[(5-{4-[(3-phenoxyphenyl)methyl]piperazin-1-yl}imidazo[1,2-c]pyrimidin-2-yl)methyl]-5,6,7,8-tetrahydroquinolin-8-amine | 560.2 |
| 58 | 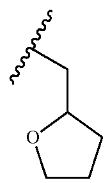 [SMILES: *CC1CCCO1] | (S)-N-methyl-N-({5-[4-(oxolan-2-ylmethyl)piperazin-1-yl]imidazo[1,2-c]pyrimidin-2-yl}methyl)-5,6,7,8-tetrahydroquinolin-8-amine | 462.1 |
| 59 | 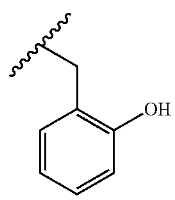 [SMILES: *Cc1ccccc1O] | 2-({4-[2-({methyl[(S)-5,6,7,8-tetrahydroquinolin-8-yl]amino}methyl)imidazo[1,2-c]pyrimidin-5-yl]piperazin-1-yl}methyl)phenol | 484.1 |
| 60 | 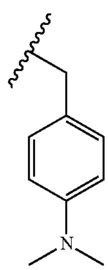 [SMILES: *Cc1ccc(N(C)C)cc1] | (8S)-N-{[5-(4-{[4-(dimethylamino)phenyl]methyl}piperazin-1-yl)imidazo[1,2-c]pyrimidin-2-yl]methyl}-N-methyl-5,6,7,8-tetrahydroquinolin-8-amine | 511.3 |
| 61 | 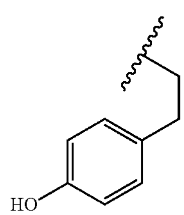 [SMILES: *CCc1ccc(O)cc1] | 4-(2-{4-[2-({methyl[(S)-5,6,7,8-tetrahydroquinolin-8-yl]amino}methyl)imidazo[1,2-c]pyrimidin-5-yl]piperazin-1-yl}ethyl)phenol | 498.2 |
| 62 | 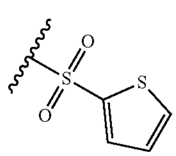 [SMILES: *S(=O)(=O)c1cccs1] | (S)-N-methyl-N-({5-[4-(thiophene-2-sulfonyl)piperazin-1-yl]imidazo[1,2-c]pyrimidin-2-yl}methyl)-5,6,7,8-tetrahydroquinolin-8-amine | 523.9 |
| 63 | 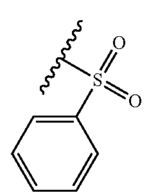 [SMILES: *S(=O)(=O)c1ccccc1] | (S)-N-({5-[4-(benzenesulfonyl)piperazin-1-yl]imidazo[1,2-c]pyrimidin-2-yl}methyl)-N-methyl-5,6,7,8-tetrahydroquinolin-8-amine | 518.0 |

-continued

| Ex. No. | Structure | Name | LC/MS (M + H)+ |
|---|---|---|---|
| 64 | 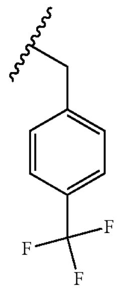 [SMILES: *Cc1ccc(C(F)(F)F)cc1] | (S)-N-methyl-N-{[5-(4-{[4-(trifluoromethyl)phenyl]methyl}piperazin-1-yl)imidazo[1,2-c]pyrimidin-2-yl]methyl}-5,6,7,8-tetrahydroquinolin-8-amine | 536.4 |
| 65 | 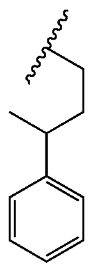 [SMILES: *CCC(C)c1ccccc1] | (S)-N-methyl-N-({5-[4-(3-phenylbutyl)piperazin-1-yl]imidazo[1,2-c]pyrimidin-2-yl}methyl)-5,6,7,8-tetrahydroquinolin-8-amine | 510.4 |
| 66 | 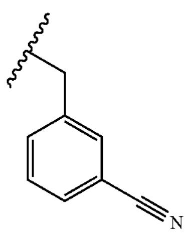 [SMILES: *Cc1cccc(C#N)c1] | 3-({4-[2-({methyl[(S)-5,6,7,8-tetrahydroquinolin-8-yl]amino}methyl)imidazo[1,2-c]pyrimidin-5-yl]piperazin-1-yl}methyl)benzonitrile | 493.1 |
| 67 | 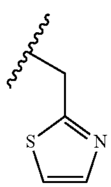 [SMILES: *Cc1nccs1] | (S)-N-methyl-N-({5-[4-(1,3-thiazol-2-ylmethyl)piperazin-1-yl]imidazo[1,2-c]pyrimidin-2-yl}methyl)-5,6,7,8-tetrahydroquinolin-8-amine | 475.0 |
| 68 | 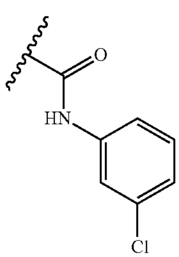 [SMILES: *C(=O)Nc1cccc(Cl)c1] | N-(3-chlorophenyl)-4-[2-({methyl[(S)-5,6,7,8-tetrahydroquinolin-8-yl]amino}methyl)imidazo[1,2-c]pyrimidin-5-yl]piperazine-1-carboxamide | 531.0 |
| 69 | 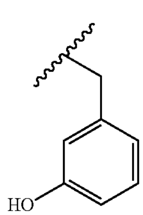 | 3-({4-[2-({methyl[(S)-5,6,7,8-tetrahydroquinolin-8-yl]amino}methyl)imidazo[1,2-c]pyrimidin-5-yl]piperazin-1-yl}methyl)phenol | 484.1 |

Example 70

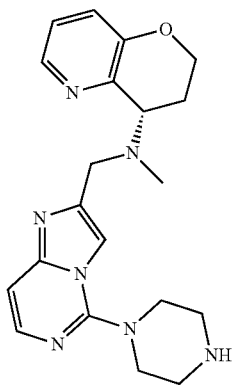 [SMILES: CN(Cc1cn2c(N3CCNCC3)nccc2n1)[C@H]1CCOc2cccnc21]

(S)—N-Methyl-N-((5-(piperazin-1-yl)imidazo[1,2-c]
pyrimidin-2-yl)methyl)-3,4-dihydro-2H-pyrano[3,2-
b]pyridin-4-amine

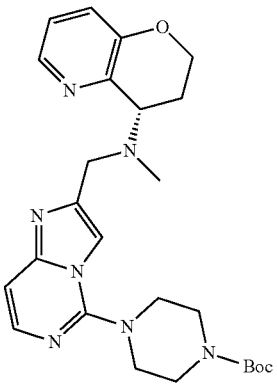 [SMILES: CN(Cc1cn2c(N3CCN(C(=O)OC(C)(C)C)CC3)nccc2n1)[C@H]1CCOc2cccnc21]

A) tert-Butyl (S)-4-(2-(((3,4-dihydro-2H-pyrano[3,
2-b]pyridin-4-yl)(methyl)amino)methyl)imidazo[1,
2-c]pyrimidin-5-yl)piperazine-1-carboxylate A mixture of tert-butyl 4-(2-formylimidazo[1,2-c]pyrimidin-5-yl)piperazine-1-carboxylate (40 mg, 0.121 mmol) and (S)—N-methyl-3,4-dihydro-2H-pyrano[3,2-b]pyridin-4-amine (23.79 mg, 0.145 mmol) in DCE (1 mL) was stirred at rt for 5 min. Solid sodium triacetoxyborohydride (64.0 mg, 0.302 mmol) was then added. After stirring at rt 1 h, the reaction mixture was concentrated in vacuo. The residue was purified by flash chromatography using an Isco 40 g column eluting with 0-15% MeOH/DCM containing 2N ammonia to give the title compound (34 mg, 59% yield) as a colorless oil. $^1$H NMR (400 MHz, CD3OD) δ 8.17 (d, J=4 Hz, 1H), 7.85 (s, 1H), 7.76 (d, J=4 Hz, 1H), 7.22-7.20 (m, 2H), 7.10 (dd, J=8, 4 Hz, 1H), 4.48-4.46 (m, 1H), 4.25-4.20 (m, 1H), 4.12-4.08 (m, 1H), 3.92-3.90 (m, 2H), 3.71-3.70 (m, 4H), 3.46-3.43 (m, 4H), 2.37 (s, 3H), 2.37-2.34 (m, 1H), 2.18-2.15 (m, 1H); MS (ESI$^+$) m/z 480.2 (M+H)$^+$.

B) (S)—N-Methyl-N-((5-(piperazin-1-yl)imidazo[1,
2-c]pyrimidin-2-yl)methyl)-3,4-dihydro-2H-pyrano
[3,2-b]pyridin-4-amine A solution of (S)-tert-butyl 4-(2-(((3,4-dihydro-2H-pyrano[3,2-b]pyridin-4-yl)(methyl)amino)methyl)imidazo[1,2-c]pyrimidin-5-yl)piperazine-1-carboxylate (27 mg, 0.056 mmol) in DCM (3 mL) was treated with TFA (1 mL). After stirring at rt 2 h, the reaction was concentrated in vacuo. The residue was purified directly by prep hplc using a C18 Phen Luna Axia 21.20×250 mm column eluting with 0-100% solvent A/B over a 30 minute gradient (Solvent A: 95% H$_2$O/5% MeCN/10 mM NH$_4$OAc; Solvent B: 5% H$_2$O/95% MeCN/10 mM NH$_4$OAc). The product eluted at 10.4 min. The desired fractions were combined and then lyophilized to give the title compound (15 mg, 67% yield) as a white solid. $^1$H NMR (400 MHz, CD3OD) δ 8.17 (d, J=4 Hz, 1H), 7.90 (s, 1H), 7.81 (d, J=8 Hz, 1H), 7.23-7.22 (m, 1H), 7.17 (dd, J=8, 4 Hz, 1H), 4.49-4.46 (m, 1H), 4.25-4.15 (m, 2H), 3.95 (q, J=8 Hz, 2H), 3.68-3.66 (m, 4H), 3.43-3.40 (m, 4H), 2.39 (s, 3H), 2.39-2.35 (m, 1H), 2.20-2.15 (m, 1H); MS (ESI$^+$) m/z 380.2 (M+H)$^+$.

Example 71

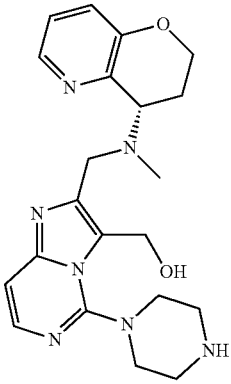 [SMILES: CN(Cc1nc2ccnc(N3CCNCC3)n2c1CO)[C@H]1CCOc2cccnc21]

(S)-(2-(((3,4-Dihydro-2H-pyrano[3,2-b]pyridin-4-yl)
(methyl)amino)methyl)-5-(piperazin-1-yl)imidazo[1,
2-c]pyrimidin-3-yl)methanol

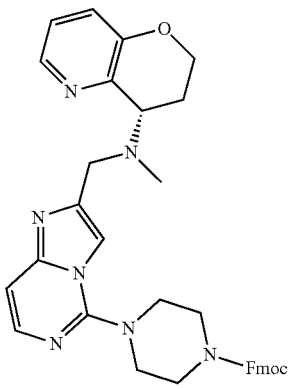

A) (9H-Fluoren-9-yl)methyl (S)-4-(2-(((3,4-di-hydro-2H-pyrano[3,2-b]pyridin-4-yl)(methyl)amino) methyl)imidazo[1,2-c]pyrimidin-5-yl)piperazine-1-carboxylate To a solution of (S)—N-methyl-N-((5-(piperazin-1-yl)imidazo[1,2-c]pyrimidin-2-yl)methyl)-3,4-dihydro-2H-pyrano[3,2-b]pyridin-4-amine, 4 TFA (46.8 mg, 0.056 mmol) in THF (2 mL) was added (9H-fluoren-9-yl)methyl (2,5-dioxopyrrolidin-1-yl) carbonate (22.67 mg, 0.067 mmol) and DIPEA (0.098 mL, 0.560 mmol). After stirring at rt for 30 min, the reaction mixture was purified directly by flash chromatography using an Isco 40 g column eluting with 0-20% MeOH/DCM to give the title compound (43 mg, 128% yield) as a colorless oil. $^1$H NMR (400 MHz, CD3OD) δ 8.16 (d, J=4 Hz, 1H), 7.83-7.75 (m, 4H), 7.65 (d, J=8 Hz, 1H), 7.42-7.32 (m, 4H), 7.20 (d, J=4 Hz, 2H), 7.10 (d, J=4 Hz, 1H), 4.60 (d, J=8 Hz, 2H), 4.49-4.45 (m, 1H), 4.38-4.35 (m, 1H), 4.25-4.20 (m, 1H), 4.12-4.08 (m, 1H), 3.92-3.90 (m, 2H), 3.70-3.52 (m, 4H), 3.46-3.35 (m, 4H), 2.36 (s, 3H), 2.37-2.34 (m, 1H), 2.18-2.15 (m, 1H); MS (ESI$^+$) m/z 602.2 (M+H)$^+$.

B) (S)-(2-(((3,4-Dihydro-2H-pyrano[3,2-b]pyridin-4-yl)(methyl)amino)methyl)-5-(piperazin-1-yl)imidazo[1,2-c]pyrimidin-3-yl)methanol A solution of (S)-(9H-fluoren-9-yl)methyl 4-(2-(((3,4-dihydro-2H-pyrano[3,2-b]pyridin-4-yl)(methyl)amino) methyl)imidazo[1,2-c]pyrimidin-5-yl)piperazine-1-carboxylate (33.7 mg, 0.056 mmol) in DCE (1 mL) was charged with formaldehyde, 37% aq (0.031 mL, 1.120 mmol) and acetic acid (0.5 mL). Solid sodium triacetoxyborohydride (11.87 mg, 0.056 mmol) was then added. After stirring at 50° C. over the weekend and then at 60° C. for 24 h, the reaction was quenched with saturated aqueous sodium bicarbonate solution and extracted with ethyl acetate. The pooled organic extracts were dried over anhydrous sodium sulfate, filtered, and concentrated in vacuo. The residue was purified by flash chromatography using an Isco 40 g column eluting with 0-10% MeOH/DCM to give impure Fmoc-protected alcohol (13 mg) as a colorless oil. The Fmoc-protected alcohol was dissolved in in DCM (2 mL) and piperidine (0.017 mL, 0.168 mmol) was added. After stirring at rt for 2 h, the reaction mixture was concentrated in vacuo. The residue was purified by prep hplc using a C18 Phen Luna S5 21.20×100 mm column eluting with 0-100% solvent A/B over a 15 minute gradient (Solvent A: 95% H$_2$O/5% MeCN/10 mM NH$_4$OAc; Solvent B: 5% H$_2$O/95% MeCN/10 mM NH$_4$OAc). The product eluted at 7.2 min. The desired fractions were combined and then lyophilized to give the title compound (2.3 mg, 10% yield) as a white solid. $^1$H NMR (400 MHz, CD3OD) δ 8.13 (d, J=4 Hz, 1H), 7.80 (d, J=4 Hz, 1H), 7.23-7.19 (m, 3H), 5.19 (d, J=4 Hz, 2H), 4.46-4.42 (m, 1H), 4.22-4.13 (m, 2H), 4.05 (q, J=8 Hz, 2H), 3.80-3.55 (m, 8H), 2.38-2.34 (m, 2H), 2.28-2.25 (m, 2H), 2.22 (s, 3H); MS (ESI$^+$) m/z 410.2 (M+H)$^+$.

Example 72

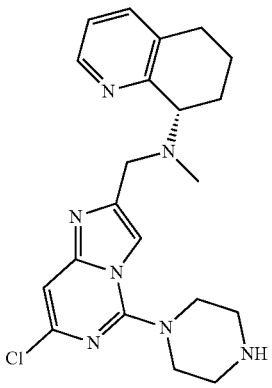 [SMILES: CN(Cc1cn2c(N3CCNCC3)nc(Cl)cc2n1)[C@H]1CCCc2cccnc21]

(S)—N-((7-Chloro-5-(piperazin-1-yl)imidazo[1,2-c]pyrimidin-2-yl)methyl)-N-methyl-5,6,7,8-tetrahydroquinolin-8-amine

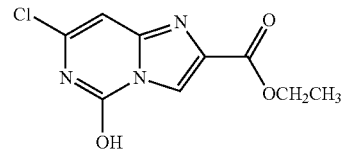

A) Ethyl 7-chloro-5-hydroxyimidazo[1,2-c]pyrimidine-2-carboxylate

A 20D vial was charged with 2,6-dichloropyrimidin-4-amine (2 g, 12.2 mmol), ethyl 3-bromo-2-oxopropanoate (3.84 mL, 30.5 mmol) in acetic acid (20 mL). The reaction was heated at 120° C. for 2 hours. The reaction was concentrated in vacuo and the residue dissolved in diethyl ether and filtered. The filtered dark brown precipitate (2.95 g, 100% yield) was used as in in next step without purification. $^1$H NMR (400 MHz, METHANOL-d$_4$) δ 8.57 (s, 1H), 6.91 (d, J=0.6 Hz, 1H), 4.48 (q, J=7.1 Hz, 2H), 1.44 (t, J=7.2 Hz, 3H); MS (ESI$^+$) m/z 242.1 (M+H)$^+$.

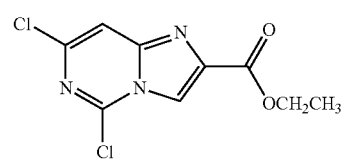 [SMILES: CCOC(=O)c1cn2c(Cl)nc(Cl)cc2n1]

B) Ethyl 5,7-dichloroimidazo[1,2-c]pyrimidine-2-carboxylate

A 20D vial was charged with ethyl 7-chloro-5-hydroxyimidazo[1,2-c]pyrimidine-2-carboxylate (2.95 g g, 12.19 mmol) and phosphorus oxychloride (12.74 ml, 137 mmol). The reaction was heated with a reflux condenser at 120° C. for 8 hours. The reaction was cooled and excess POCl$_3$ removed, and ice water added. The aqueous solution was basified with NaOH (1N solution) to pH=8, and the product extracted with DCM (3×). The organic layers were washed with water followed by saturated aqueous sodium chloride, dried with anhydrous sodium sulfate, filtered, and concentrated in vacuo to give a solid (2.7 g, 85% yield) which was used as is in the next step without purification. $^1$H NMR (400 MHz, CHLOROFORM-d) δ 8.32 (d, J=0.7 Hz, 1H), 7.61 (d, J=0.9 Hz, 1H), 4.51 (q, J=7.1 Hz, 2H), 1.48 (t, J=7.2 Hz, 3H); MS (ESI$^+$) m/z 260.1 (M+H)+.

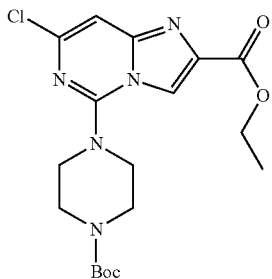 [SMILES: CCOC(=O)c1cn2c(N3CCN(C(=O)OC(C)(C)C)CC3)nc(Cl)cc2n1]

C) Ethyl 5-(4-(tert-butoxycarbonyl)piperazin-1-yl)-7-chloroimidazo[1,2-c]pyrimidine-2-carboxylate A flask was charged with ethyl 5,7-dichloroimidazo[1,2-c]pyrimidine-2-carboxylate (2.7 g, 10.4 mmol) and 1-boc-piperazine (2.31 g, 12.5 mmol) in DCM (15 mL). The reaction solution was stirred at 0° C., then warmed to RT for 3 days. The reaction was quenched with water and extracted with DCM (3×), washed with water followed by saturated aqueous sodium chloride, dried with anhydrous sodium sulfate, filtered, and concentrated in vacuo. The crude product mixture was purified by a silica gel ISCO 40 g column, eluting with 0-100% of ethyl acetate/DCM over a 15 minute gradient. The appropriate fractions were isolated and concentrated in vacuo to afford the product (1.2 g, 28% yield over 3 steps) as a solid. $^1$H NMR (400 MHz, CHLOROFORM-d) δ 7.97 (s, 1H), 7.18 (s, 1H), 4.43 (q, J=7.1 Hz, 2H), 3.65 (dd, J=6.1, 3.8 Hz, 4H), 3.59-3.34 (m, 4H), 1.47 (s, 9H), 1.45-1.34 (m, 3H); MS (ESI$^+$) m/z 410.1 (M+H)$^+$.

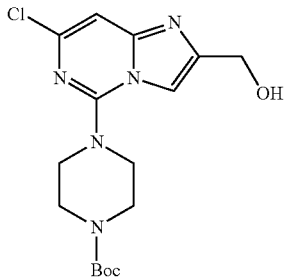 [SMILES: CC(C)(C)OC(=O)N1CCN(c2nc(Cl)cc3nc(CO)cn23)CC1]

D) tert-Butyl 4-(7-chloro-2-(hydroxymethyl)imidazo[1,2-c]pyrimidin-5-yl)piperazine-1-carboxylate To a solution of ethyl 5-(4-(tert-butoxycarbonyl)piperazin-1-yl)-7-chloroimidazo[1,2-c]pyrimidine-2-carboxylate (0.375 g, 0.915 mmol) in THF (12 mL) at 0° C. was added dropwise a solution of LiAlH$_4$ (1M in THF, 1.10 mL, 1.10 mmol). After stirring at 0° C. for 60 min, the reaction mixture was quenched dropwise with water followed by 1N aqueous NaOH solution and stirred at rt for 30 minutes. The mixture was diluted with ethyl acetate, filtered through anhydrous sodium sulfate, and the filtrate concentrated. The crude product mixture was purified by a silica gel ISCO 12 g column, eluting with 0-100% of ethyl acetate/DCM over a 15 minute gradient. The appropriate fractions were isolated and concentrated in vacuo to afford the product (60 mg, 18% yield) as a solid. $^1$H NMR (400 MHz, METHANOL-d$_4$) δ 7.65 (d, J=0.7 Hz, 1H), 7.11 (d, J=0.6 Hz, 1H), 4.74 (d, J=0.7 Hz, 2H), 3.67 (d, J=3.3 Hz, 4H), 3.59-3.43 (m, 4H), 1.61-1.48 (m, 9H); MS (ESI$^+$) m/z 368.1 (M+H)$^+$.

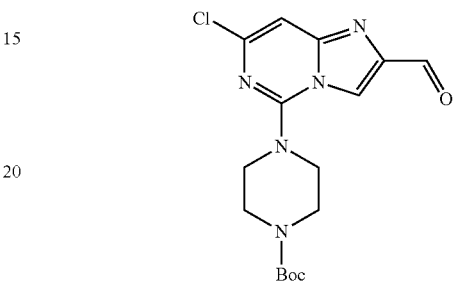

E) tert-Butyl 4-(7-chloro-2-formylimidazo[1,2-c]pyrimidin-5-yl)piperazine-1-carboxylate In a flask, tert-butyl 4-(7-chloro-2-(hydroxymethyl)imidazo[1,2-c]pyrimidin-5-yl)piperazine-1-carboxylate (60 mg, 0.163 mmol) was dissolved in 1/1 acetonitrile/CHCl$_3$ and the resulting solution then treated with manganese dioxide (142 mg, 1.63 mmol). The reaction mixture was stirred at RT for 3 days. The reaction mixture was then filtered through a pad of celite, washing the celite with several portions of CHCl$_3$. The filtrate was concentrated in vacuo. The residue was purified by a 30 g Rf Gold® Reversed-phase C18 column, eluting with 10% to 100% of 0.1% TFA in acetonitrile/0.1% ammonium acetate in water over a 15 minute gradient. The appropriate fractions were isolated and concentrated in vacuo to afford the product (40 mg, 67% yield) as a solid. $^1$H NMR (400 MHz, CHLOROFORM-d) δ 10.14 (s, 1H), 8.00 (d, J=0.6 Hz, 1H), 7.37-7.15 (m, 1H), 5.31 (s, 1H), 3.85-3.38 (m, 11H), 2.21-1.88 (m, 2H), 1.54-1.34 (m, 15H); MS (ESI$^+$) m/z 366 (M+H)$^+$.

F) (S)—N-((7-chloro-5-(piperazin-1-yl)imidazo[1,2-c]pyrimidin-2-yl)methyl)-N-methyl-5,6,7,8-tetrahydroquinolin-8-amine To a solution of (S)—N-methyl-5,6,7,8-tetrahydroquinolin-8-amine (21.3 mg, 0.131 mmol) in DCE (10 mL) was added tert-butyl 4-(7-chloro-2-formylimidazo[1,2-c]pyrimidin-5-yl)piperazine-1-carboxylate (40 mg, 0.109 mmol). The reaction was stirred at RT for 30 min. Solid sodium triacetoxyborohydride (34.8 mg, 0.164 mmol) was added and stirred at rt for 3 days. The reaction was quenched with 1N NaOH aqueous solution, extracted with DCM, dried with anhydrous sodium sulfate and concentrated in vacuo. The crude product mixture was purified by a silica gel 12 g ISCO column, eluting with 0-70% (20% NH$_3$/MeOH)/DCM over a 15 min gradient. The appropriate fractions were isolated and concentrated to afford tert-butyl (S)-4-(7-chloro-2-((methyl(5,6,7,8-tetrahydroquinolin-8-yl)amino)methyl)imidazo[1,2-c]pyrimidin-5-yl)piperazine-1-carboxylate (32 mg, 57% yield) as a solid.

The above product was dissolved in DCM (8 mL) and TFA (1.4 mL) was added. The reaction was stirred at RT for 2 hours. The solution was concentrated in vacuo. The crude compound was purified via preparative LC/MS using a Waters XBridge C18 column, 19×200 mm; eluting with 0-70% aqueous methanol with 0.1% TFA over a 20 minute gradient. The appropriate fractions were isolated, passed through a PL-HCO$_3$ cartridge and concentrated to afford the title compound (13 mg, 27%) as a solid. $^1$H NMR (400 MHz, METHANOL-d$_4$) δ 8.45 (d, J=3.4 Hz, 1H), 7.93 (d, J=0.5 Hz, 1H), 7.57 (dd, J=7.6, 0.7 Hz, 1H), 7.23 (dd, J=7.6, 4.8 Hz, 1H), 7.12 (d, J=0.6 Hz, 1H), 4.19 (dd, J=9.1, 5.8 Hz, 1H), 4.04-3.81 (m, 2H), 3.70-3.53 (m, 4H), 3.21 (dd, J=6.1, 4.0 Hz, 4H), 3.03-2.73 (m, 2H), 2.51-2.33 (m, 3H), 2.29-1.66 (m, 4H); MS (ESI$^+$) m/z 412.2 (M+H)$^+$.

Example 73

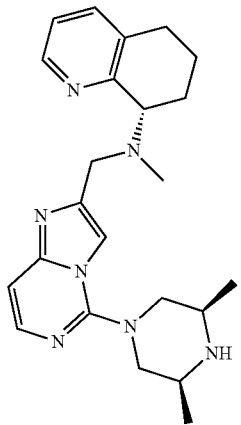 [SMILES: C[C@@H]1CN(c2nccc3nc(CN(C)[C@H]4CCCc5cccnc54)cn23)C[C@H](C)N1]

(S)—N-((5-((3S,5R)-3,5-Dimethylpiperazin-1-yl) imidazo[1,2-c]pyrimidin-2-yl)methyl)-N-methyl-5,6, 7,8-tetrahydroquinolin-8-amine

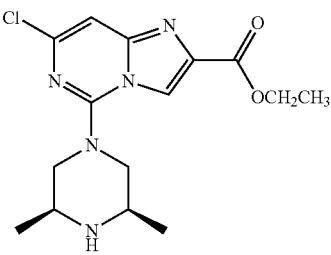 [SMILES: CCOC(=O)c1cn2c(N3C[C@@H](C)N[C@@H](C)C3)nc(Cl)cc2n1]

A) Ethyl 7-chloro-5-((3S,5R)-3,5-dimethylpiper-azin-1-yl)imidazo[1,2-c]pyrimidine-2-carboxylate To a solution of ethyl 5,7-dichloroimidazo[1,2-c]pyrimidine-2-carboxylate (0.5 g, 1.92 mmol, Step B of EXAMPLE 72) in THF (3 mL) was added DIPEA (1.68 mL, 9.61 mmol) followed by cis 2,6-dimethylpiperazine (0.66 g, 5.8 mmol). After stirring at rt 2 h, the reaction was diluted with ethyl acetate, washed with saturated aqueous sodium bicarbonate solution, dried over anhydrous sodium sulfate, filtered, and concentrated in vacuo. The residue was purified by flash chromatography using an Isco 80 g column eluting with 0-5% MeOH/DCM to give the product (135 mg, 21% yield) as a yellow oil. $^1$H NMR (400 MHz, METHANOL-d$_4$) δ 8.25 (s, 1H), 7.14 (s, 1H), 4.43 (q, J=8 Hz, 2H), 4.02 (d, J 8 Hz, 2H), 3.33-3.32 (m, 2H), 2.95-2.89 (m, 2H), 1.42 (t, J=8 Hz, 3H), 1.27 (d, J 8 Hz, 6H); MS (ESI$^+$) m/z 338.1 (M+H)$^+$.

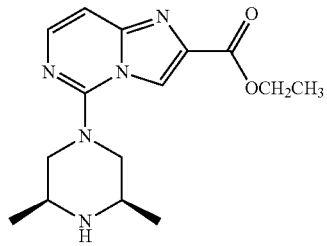 [SMILES: CCOC(=O)c1cn2c(N3C[C@@H](C)N[C@@H](C)C3)nccc2n1]

B) Ethyl 5-((3S,5R)-3,5-dimethylpiperazin-1-yl) imidazo[1,2-c]pyrimidine-2-carboxylate To a solution of ethyl 7-chloro-5-((3S,5R)-3,5-dimethyl-piperazin-1-yl)imidazo[1,2-c]pyrimidine-2-carboxylate (135 mg, 0.40 mmol) in MeOH (2 mL) under nitrogen was added Pearlman's Catalyst (28.1 mg, 0.040 mmol). A balloon filled with hydrogen was added and the reaction was stirred at rt 1 h. The reaction was flushed with nitrogen and then filtered to remove the palladium catalyst. The filtrate was concentrated in vacuo to give the crude product (103 mg, 85% yield) as a white solid. $^1$H NMR (400 MHz, METHANOL-d$_4$) δ 8.55 (s, 1H), 8.08 (d, J=8 Hz, 1H), 7.37 (d, J=8 Hz, 1H), 4.48 (q, J=4 Hz, 2H), 4.16-4.12 (m, 2H), 3.79-3.74 (m, 2H), 3.37-3.28 (m, 2H), 1.49-1.41 (m, 9H); MS (ESI$^+$) m/z 304.1 (M+H)+.

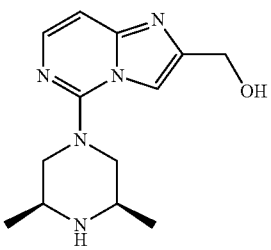 [SMILES: C[C@@H]1CN(c2nccc3nc(CO)cn23)C[C@H](C)N1]

C) (5-((3S,5R)-3,5-Dimethylpiperazin-1-yl)imidazo [1,2-c]pyrimidin-2-yl)methanol To a solution of ethyl 5-((3S,5R)-3,5-dimethylpiperazin-1-yl)imidazo[1,2-c]pyrimidine-2-carboxylate (100 mg, 0.33 mmol) in THF (2 mL) at −78° C. was added LAH, 1M THF (0.49 mL, 0.49 mmol). The reaction was slowly warmed to 0° C. and was then quenched with 1N aqueous sodium hydroxide solution (0.5 mL). After stirring at rt for 30 min, the reaction was concentrated in vacuo. The residue was purified directly by flash chromatography using an Isco 40 g column eluting with 0-20% MeOH/DCM containing 2N ammonia to give the product (49 mg, 57% yield) as a pale yellow oil. $^1$H NMR (400 MHz, METHANOL-d$_4$) δ 7.78 (d, J=4 Hz, 1H), 7.62 (s, 1H), 7.10 (d, J=4 Hz, 1H), 4.78 (s, 2H), 3.83-3.79 (m, 2H), 3.16-3.13 (m, 2H), 2.68-2.62 (m, 2H), 1.17 (d, J=4 Hz, 6H); MS (ESI$^+$) m/z 262.2 (M+H)$^+$.

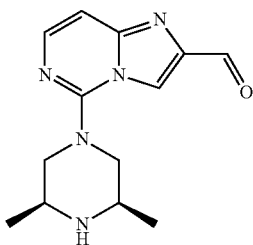 [SMILES: C[C@@H]1CN(c2nccc3nc(C=O)cn23)C[C@H](C)N1]

D) 5-((3S,5R)-3,5-Dimethylpiperazin-1-yl)imidazo[1,2-c]pyrimidine-2-carbaldehyde To a solution of (5-((3S,5R)-3,5-dimethylpiperazin-1-yl)imidazo[1,2-c]pyrimidin-2-yl)methanol (49 mg, 0.188 mmol) in DCM (5 mL) was added manganese dioxide (163 mg, 1.88 mmol). After stirring at rt 3 h, the reaction mixture was filtered through a pad of celite using DCM to give the crude product (25 mg, 51% yield) as a colorless oil. $^1$H NMR (400 MHz, METHANOL-$d_4$) δ 10.08 (s, 1H), 7.78 (d, J=8 Hz, 1H), 7.63 (s, 1H), 7.11 (d, J=8 Hz, 1H), 3.81-3.78 (m, 2H), 3.15-3.13 (m, 2H), 2.68-2.64 (m, 2H), 1.17 (d, J=4 Hz, 6H); MS (ESI$^+$) m/z 260.2 (M+H)$^+$.

E) (S)—N-((5-((3S,5R)-3,5-Dimethylpiperazin-1-yl)imidazo[1,2-c]pyrimidin-2-yl)methyl)-N-methyl-5,6,7,8-tetrahydroquinolin-8-amine A mixture of 5-((3S,5R)-3,5-dimethylpiperazin-1-yl)imidazo[1,2-c]pyrimidine-2-carbaldehyde (25 mg, 0.096 mmol) and (S)—N-methyl-5,6,7,8-tetrahydroquinolin-8-amine (23.5 mg, 0.145 mmol) in DCE (1.5 mL) was charged with sodium triacetoxyborohydride (30.7 mg, 0.145 mmol). After stirring rt 1 h, the reaction mixture was concentrated in vacuo. The residue was dissolved in MeOH and then purified by prep hplc using a C18 Phen Luna S5 ODS 21.20×100 mm column eluting with 0-90% solvent A/B over a 15 minute gradient (Solvent A: 95% H$_2$O/5% MeCN/10 mM NH$_4$OAc; Solvent B: 5% H$_2$O/95% MeCN/10 mM NH$_4$OAc). The product eluted at 6.3 min. The desired fractions were combined and then lyophilized to give the title compound (29 mg, 72% yield) as a yellow solid. $^1$H NMR (400 MHz, METHANOL-$d_4$) δ 8.48 (d, J=4 Hz, 1H), 7.96 (s, 1H), 7.81 (d, J=4 Hz, 1H), 7.61 (d, J=8 Hz, 1H), 7.27 (dd, J=4, 8 Hz, 1H), 7.17 (d, J=4 Hz, 1H), 4.34-4.32 (m, 1H), 4.12 (q, J=8 Hz, 2H), 4.00-3.96 (m, 2H), 3.53-3.49 (m, 2H), 3.00-2.84 (m, 4H), 2.52 (s, 3H), 2.38-2.32 (m, 1H), 2.12-2.05 (m, 2H), 1.98-1.94 (m, 1H), 1.35-1.31 (m, 6H); MS (ESI$^+$) m/z 406.2 (M+H)$^+$.

Examples 74-96

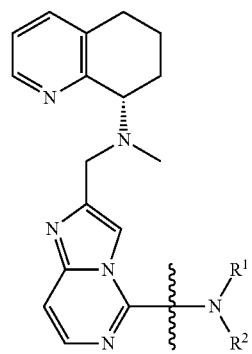

The following examples were prepared according to the procedures described for the synthesis of Example 73:

| Ex. No. | Structure | Name | LC/MS (M + H)$^+$ |
|---|---|---|---|
| 74 | 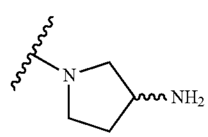 [SMILES: *N1CCC(N)C1] | (8S)-N-((5-(3-aminopyrrolidin-1-yl)imidazo[1,2-c]pyrimidin-2-yl)methyl)-N-methyl-5,6,7,8-tetrahydroquinolin-8-amine | 378.2 |
| 75 | 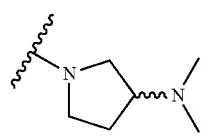 [SMILES: *N1CCC(N(C)C)C1] | (8S)-N-((5-(3-(dimethylamino)pyrrolidin-1-yl)imidazo[1,2-c]pyrimidin-2-yl)methyl)-N-methyl-5,6,7,8-tetrahydroquinolin-8-amine | 378.2 |
| 76 | 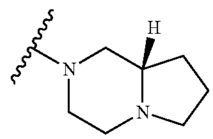 [SMILES: *N1CCN2CCC[C@H]2C1] | (S)-N-((5-((S)-hexahydropyrrolo[1,2-a]pyrazin-2(1H)-yl)imidazo[1,2-c]pyrimidin-2-yl)methyl)-N-methyl-5,6,7,8-tetrahydroquinolin-8-amine | 418.1 |
| 77 | 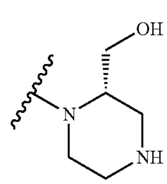 [SMILES: *N1CCNC[C@H]1CO] | ((S)-1-(2-((methyl((S)-5,6,7,8-tetrahydroquinolin-8-yl)amino)methyl)imidazo[1,2-c]pyrimidin-5-yl)piperazin-2-yl)methanol | 408.2 |

-continued

| Ex. No. | Structure | Name | LC/MS (M + H)+ |
|---|---|---|---|
| 78 | isomer 1 | (8S)-N-methyl-N-((5-(3-phenylpiperazin-1-yl)imidazo[1,2-c]pyrimidin-2-yl)methyl)-5,6,7,8-tetrahydroquinolin-8-amine | 454.1 |
| 79 | isomer 2 | (8S)-N-methyl-N-((5-(3-phenylpiperazin-1-yl)imidazo[1,2-c]pyrimidin-2-yl)methyl)-5,6,7,8-tetrahydroquinolin-8-amine | 454.1 |
| 80 | cis | (8S)-N-((5-(hexahydropyrrolo[3,4-c]pyrrol-2(1H)-yl)imidazo[1,2-c]pyrimidin-2-yl)methyl)-N-methyl-5,6,7,8-tetrahydroquinolin-8-amine | 404.1 |
| 81 | cis | (8S)-N-methyl-N-((5-(5-methylhexahydropyrrolo[3,4-c]pyrrol-2(1H)-yl)imidazo[1,2-c]pyrimidin-2-yl)methyl)-5,6,7,8-tetrahydroquinolin-8-amine | 418.0 |
| 82 | 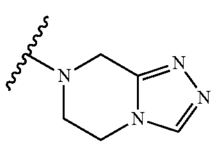 [SMILES: *N1CCn2cnnc2C1] | (S)-N-((5-(5,6-dihydro-[1,2,4]triazolo[4,3-a]pyrazin-7(8H)-yl)imidazo[1,2-c]pyrimidin-2-yl)methyl)-N-methyl-5,6,7,8-tetrahydroquinolin-8-amine | 416.0 |
| 83 | 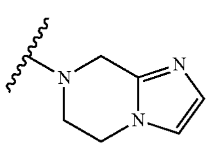 [SMILES: *N1CCn2ccnc2C1] | (S)-N-((5-(5,6-dihydroimidazo[1,2-a]pyrazin-7(8H)-yl)imidazo[1,2-c]pyrimidin-2-yl)methyl)-N-methyl-5,6,7,8-tetrahydroquinolin-8-amine | 415.0 |
| 84 | 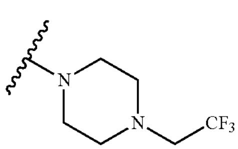 [SMILES: *N1CCN(CC(F)(F)F)CC1] | (S)-N-methyl-N-((5-(4-(2,2,2-trifluoroethyl)piperazin-1-yl)imidazo[1,2-c]pyrimidin-2-yl)methyl)-5,6,7,8-tetrahydroquinolin-8-amine | 460.0 |
| 85 | 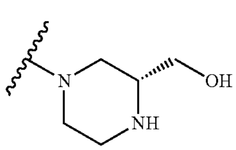 [SMILES: *N1CCN[C@@H](CO)C1] | ((R)-4-(2-((methyl((S)-5,6,7,8-tetrahydroquinolin-8-yl)amino)methyl)imidazo[1,2-c]pyrimidin-5-yl)piperazin-2-yl)methanol | 408.0 |
| 86 | 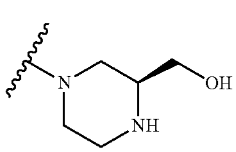 [SMILES: *N1CCN[C@H](CO)C1] | ((S)-4-(2-((methyl((S)-5,6,7,8-tetrahydroquinolin-8-yl)amino)methyl)imidazo[1,2-c]pyrimidin-5-yl)piperazin-2-yl)methanol | 408.1 |

-continued

| Ex. No. | Structure | Name | LC/MS (M + H)+ |
|---|---|---|---|
| 87 | 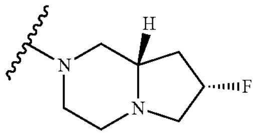 [SMILES: *N1CCN2C[C@@H](F)C[C@H]2C1] | (S)-N-((5-((7S,8aS)-7-fluorohexahydropyrrolo[1,2-a]pyrazin-2(1H)-yl)imidazo[1,2-c]pyrimidin-2-yl)methyl)-N-methyl-5,6,7,8-tetrahydroquinolin-8-amine | 436.1 |
| 88 | isomer 1 | (8S)-N-((5-(3,6-diazabicyclo[3.2.0]heptan-3-yl)imidazo[1,2-c]pyrimidin-2-yl)methyl)-N-methyl-5,6,7,8-tetrahydroquinolin-8-amine | 390.0 |
| 89 | isomer 2 | (8S)-N-((5-(3,6-diazabicyclo[3.2.0]heptan-3-yl)imidazo[1,2-c]pyrimidin-2-yl)methyl)-N-methyl-5,6,7,8-tetrahydroquinolin-8-amine | 390.0 |
| 90 | 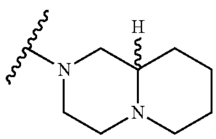 [SMILES: *N1CCN2CCCCC2C1] | (8S)-N-methyl-N-((5-(octahydro-2H-pyrido[1,2-a]pyrazin-2-yl)imidazo[1,2-c]pyrimidin-2-yl)methyl)-5,6,7,8-tetrahydroquinolin-8-amine | 432.0 |
| 91 | isomer 1 | (8S)-N-((5-(hexahydropyrazino[2,1-c][1,4]oxazin-8(1H)-yl)imidazo[1,2-c]pyrimidin-2-yl)methyl)-N-methyl-5,6,7,8-tetrahydroquinolin-8-amine | 433.9 |
| 92 | isomer 2 | (8S)-N-((5-(hexahydropyrazino[2,1-c][1,4]oxazin-8(1H)-yl)imidazo[1,2-c]pyrimidin-2-yl)methyl)-N-methyl-5,6,7,8-tetrahydroquinolin-8-amine | 433.9 |
| 93 | cis, isomer 1 | (8S)-N-((5-(hexahydropyrrolo[3,4-b]pyrrol-5(1H)-yl)imidazo[1,2-c]pyrimidin-2-yl)methyl)-N-methyl-5,6,7,8-tetrahydroquinolin-8-amine | 403.9 |
| 94 | cis, isomer 2 | (8S)-N-((5-(hexahydropyrrolo[3,4-b]pyrrol-5(1H)-yl)imidazo[1,2-c]pyrimidin-2-yl)methyl)-N-methyl-5,6,7,8-tetrahydroquinolin-8-amine | 403.9 |

-continued

| Ex. No. | Structure | Name | LC/MS (M + H)+ |
|---|---|---|---|
| 95 | cis isomer 1 | (8S)-N-((5-(hexahydro-1H-pyrrolo[3,4-b]pyridin-6(2H)-yl)imidazo[1,2-c]pyrimidin-2-yl)methyl)-N-methyl-5,6,7,8-tetrahydroquinolin-8-amine | 417.9 |
| 96 | cis isomer 2 | (8S)-N-((5-(hexahydro-1H-pyrrolo[3,4-b]pyridin-6(2H)-yl)imidazo[1,2-c]pyrimidin-2-yl)methyl)-N-methyl-5,6,7,8-tetrahydroquinolin-8-amine | 417.9 |

Example 97

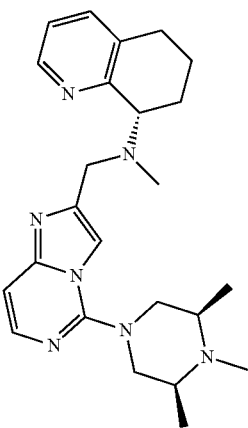 [SMILES: C[C@@H]1CN(c2nccc3nc(CN(C)[C@H]4CCCc5cccnc54)cn23)C[C@H](C)N1C]

(S)—N-Methyl-N-((5-((3S,5R)-3,4,5-trimethylpiperazin-1-yl)imidazo[1,2-c]pyrimidin-2-yl)methyl)-5,6,7,8-tetrahydroquinolin-8-amine A solution of (S)—N-((5-((3S,5R)-3,5-dimethylpiperazin-1-yl)imidazo[1,2-c]pyrimidin-2-yl)methyl)-N-methyl-5,6,7,8-tetrahydroquinolin-8-amine (18 mg, 0.044 mmol, EXAMPLE 73) in DCE (2 mL) was charged with formaldehyde, 37% aq (0.024 mL, 0.89 mmol) and acetic acid (0.2 mL). Solid sodium triacetoxyborohydride (18.8 mg, 0.089 mmol) was then added. After stirring at rt 30 min, the reaction was concentrated in vacuo. The residue was dissolved in MeOH and then purified by prep hplc using a C18 Phen Luna S5 ODS 21.20×100 mm column eluting with 0-90% solvent A/B over a 15 minute gradient (Solvent A: 95% H$_2$O/5% MeCN/10 mM NH$_4$OAc; Solvent B: 5% H$_2$O/95% MeCN/10 mM NH$_4$OAc). The product eluted at 7.2 min. The desired fractions were combined and then lyophilized to give the title compound (9 mg, 48% yield) as a yellow sticky solid. $^1$H NMR (400 MHz, CD3OD) δ 8.48 (d, J=4 Hz, 1H), 7.90 (s, 1H), 7.80 (d, J=4 Hz, 1H), 7.62-7.60 (m, 1H), 7.29-7.26 (m, 1H), 7.13 (d, J=4 Hz, 1H), 4.36-4.35 (m, 1H), 4.13-4.11 (q, J=8 Hz, 2H), 3.85-3.81 (m, 2H), 2.99-2.71 (m, 6H), 2.54 (s, 3H), 2.47 (s, 3H), 2.38-2.30 (m, 1H), 2.12-2.06 (m, 2H), 1.85-1.78 (m, 1H), 1.27-1.23 (m, 6H); MS (ESI+) m/z 420.3 (M+H)+.

Examples 98-103

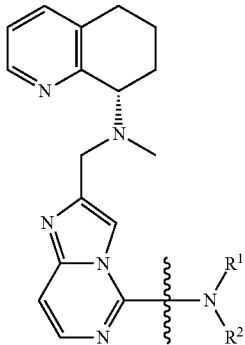

The following examples were prepared according to the procedures described for the synthesis of Example 97:

| Ex. No. | Structure | Name | LC/MS (M + H)+ |
|---|---|---|---|
| 98 | 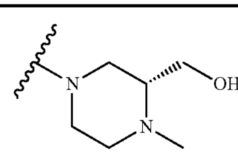 | ((R)-1-methyl-4-(2-((methyl((S)-5,6,7,8-tetrahydroquinolin-8-yl)amino)methyl)imidazo[1,2-c]pyrimidin-5-yl)piperazin-2-yl)methanol | 422.1 |

-continued

| Ex. No. | Structure | Name | LC/MS (M + H)+ |
|---|---|---|---|
| 99 | 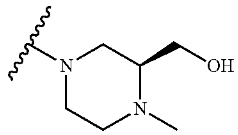 [SMILES: *N1CCN(C)[C@H](CO)C1] | ((S)-1-methyl-4-(2-((methyl((S)-5,6,7,8-tetrahydroquinolin-8-yl)amino)methyl)imidazo[1,2-c]pyrimidin-5-yl)piperazin-2-yl)methanol | 422.1 |
| 100 | cis isomer 1 | (8S)-N-methyl-N-((5-(1-methylhexahydropyrrolo[3,4-b]pyrrol-5(1H)-yl)imidazo[1,2-c]pyrimidin-2-yl)methyl)-5,6,7,8-tetrahydroquinolin-8-amine | 417.9 |
| 101 | cis isomer 2 | (8S)-N-methyl-N-((5-(1-methylhexahydropyrrolo[3,4-b]pyrrol-5(1H)-yl)imidazo[1,2-c]pyrimidin-2-yl)methyl)-5,6,7,8-tetrahydroquinolin-8-amine | 417.9 |
| 102 | cis isomer 1 | (8S)-N-methyl-N-((5-(1-methyloctahydro-6H-pyrrolo[3,4-b]pyridin-6-yl)imidazo[1,2-c]pyrimidin-2-yl)methyl)-5,6,7,8-tetrahydroquinolin-8-amine | 431.9 |
| 103 | cis isomer 2 | (8S)-N-methyl-N-((5-(1-methyloctahydro-6H-pyrrolo[3,4-b]pyridin-6-yl)imidazo[1,2-c]pyrimidin-2-yl)methyl)-5,6,7,8-tetrahydroquinolin-8-amine | 431.9 |

Example 104

(S)—N-((7-methoxy-5-(piperazin-1-yl)imidazo[1,2-c]pyrimidin-2-yl)methyl)-N-methyl-5,6,7,8-tetrahydroquinolin-8-amine

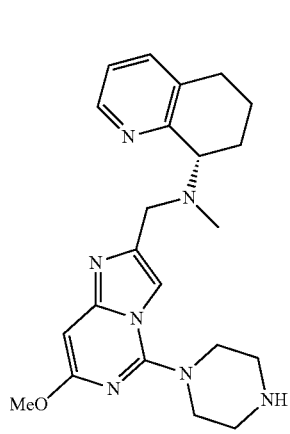 [SMILES: COc1cc2nc(CN(C)[C@H]3CCCc4cccnc43)cn2c(N2CCNCC2)n1]

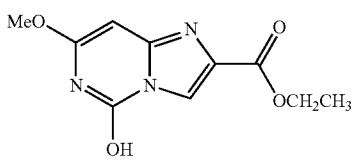 [SMILES: CCOC(=O)c1cn2c(O)nc(OC)cc2n1]

A) Ethyl 5-hydroxy-7-methoxyimidazo[1,2-c]pyrimidine-2-carboxylate

A 50 mL flask was charged with 2,6-dimethoxypyrimidin-4-amine (1 g, 6.45 mmol). THF (2.5 mL) and diethyl ether (2.5 mL) were added followed by ethyl 3-bromo-2-oxopropanoate (1.62 mL, 12.9 mmol). The reaction was stirred at rt overnight. The heterogeneous reaction was cooled to 0° C. and the precipitated intermediate salt (MW 269) was collected by vacuum filtration and washed with ether. The precipitate was dissolved in MeOH (8 mL) and heated at 60° C. for 8 h. After cooling to rt, the reaction was concentrated in vacuo. The residue was suspended in ethyl acetate, washed with saturated aqueous sodium bicarbonate solution, dried over anhydrous sodium sulfate, filtered, and concentrated in vacuo. The resulting solid was suspended in DCM/MeOH and filtered to give the product (667 mg, 44% yield) as a white solid. $^1$H NMR (400 MHz, METHANOL-d4) δ 8.57 (s, 1H), 6.91 (d, J=0.6 Hz, 1H), 4.48 (q, J=7.1 Hz, 2H), 1.44 (t, J=7.2 Hz, 3H); MS (ESI$^+$) m/z 238.1 (M+H)$^+$.

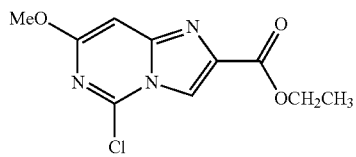 [SMILES: CCOC(=O)c1cn2c(Cl)nc(OC)cc2n1]

B) Ethyl 5-chloro-7-methoxyimidazo[1,2-c]pyrimidine-2-carboxylate

A 100 mL round bottom flask was charged with ethyl 5-hydroxy-7-methoxyimidazo[1,2-c]pyrimidine-2-carboxylate (1.1 g, 4.64 mmol). Phosphorus oxychloride (5 ml, 53.6 mmol) was added followed by two drops of DMF. The reaction was heated at 110° C. 4 h. After cooling to rt, the reaction was concentrated in vacuo to give the crude product as a brown solid. MS (ESI$^+$) m/z 256.0 (M+H)$^+$.

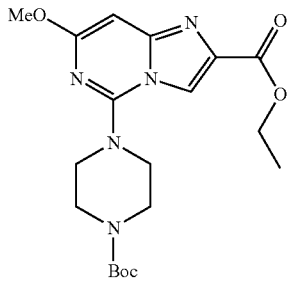

C) Ethyl 5-(4-(tert-butoxycarbonyl)piperazin-1-yl)-7-methoxyimidazo[1,2-c]pyrimidine-2-carboxylate A 25 mL round bottom flask was charged with ethyl 5-chloro-7-methoxyimidazo[1,2-c]pyrimidine-2-carboxylate (0.2 g, 0.78 mmol). DCM (5 mL) was added and the flask was cooled to 0° C. 1-BOC-Piperazine (0.29 g, 1.57 mmol) was then added followed by DIPEA (0.410 mL, 2.35 mmol) (exotherm). After stirring at rt overnight, the reaction was concentrated in vacuo. The residue was diluted with ethyl acetate, washed with saturated aqueous sodium bicarbonate solution, dried over anhydrous sodium sulfate, filtered, and concentrated in vacuo. The crude product was purified by flash chromatography using an Isco 40 g column eluting with 0-100% EtOAc/hexanes to give the product (190 mg, 60% yield) as an amber oil. $^1$H NMR (400 MHz, METHANOL-d$_4$) δ 8.09 (s, 1H), 6.32 (s, 1H), 4.43 (q, J=8 Hz, 2H), 3.93 (s, 3H), 3.73-3.68 (m, 4H), 3.56-3.53 (m, 4H), 1.55 (s, 9H), 1.25 (t, J=8 Hz, 3H); MS (ESI$^+$) m/z 406.2 (M+H)+.

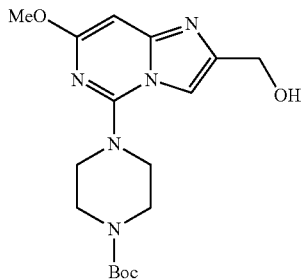 [SMILES: COc1cc2nc(CO)cn2c(N2CCN(C(=O)OC(C)(C)C)CC2)n1]

D) tert-Butyl 4-(2-(hydroxymethyl)-7-methoxyimidazo[1,2-c]pyrimidin-5-yl)piperazine-1-carboxylate To a solution of ethyl 5-(4-(tert-butoxycarbonyl)piperazin-1-yl)-7-methoxyimidazo[1,2-c]pyrimidine-2-carboxylate (170 mg, 0.419 mmol) in THF (5 mL) at −78° C. was added LAH, 1M THF (0.63 mL, 0.63 mmol). The reaction was slowly warmed to 0° C. and was then quenched with 1N aqueous sodium hydroxide solution (1 mL). After stirring at rt for 30 min, the reaction was concentrated in vacuo. The residue was purified directly by flash chromatography using an Isco 40 g column eluting with 0-10% MeOH/DCM to give the product (72 mg, 47% yield) as a yellow oil. $^1$H NMR (400 MHz, METHANOL-d$_4$) δ 7.49 (s, 1H), 6.33 (s, 1H), 4.70 (s, 2H), 3.94 (s, 3H), 3.68-3.67 (m, 4H), 3.54-3.50 (m, 4H), 1.51 (s, 9H); MS (ESI$^+$) m/z 364.1 (M+H)$^+$.

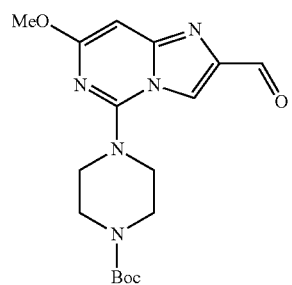 [SMILES: COc1cc2nc(C=O)cn2c(N2CCN(C(=O)OC(C)(C)C)CC2)n1]

E) tert-Butyl 4-(2-formyl-7-methoxyimidazo[1,2-c]pyrimidin-5-yl)piperazine-1-carboxylate To a solution of tert-butyl 4-(2-(hydroxymethyl)-7-methoxyimidazo[1,2-c]pyrimidin-5-yl)piperazine-1-carboxylate (72 mg, 0.198 mmol) in DCE (5 mL) was added manganese dioxide (172 mg, 1.98 mmol). After stirring at 50° C. for 8 h and then at rt overnight, the reaction mixture was filtered through a pad of celite with 10% MeOH/DCM to give the crude product (60 mg, 84% yield) as a brown oil. MS (ESI$^+$) m/z 362.1 (M+H)$^+$.

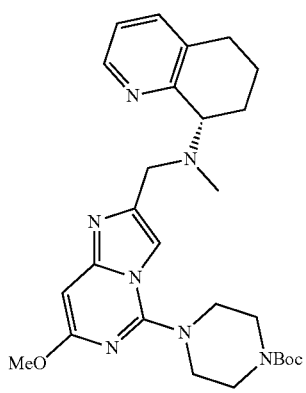 [SMILES: COc1cc2nc(CN(C)[C@H]3CCCc4cccnc43)cn2c(N2CCN(C(=O)OC(C)(C)C)CC2)n1]

F) tert-Butyl (S)-4-(7-methoxy-2-((methyl(5,6,7,8-tetrahydroquinolin-8-yl)amino)methyl)imidazo[1,2-c]pyrimidin-5-yl)piperazine-1-carboxylate A mixture of tert-butyl 4-(2-formyl-7-methoxyimidazo[1,2-c]pyrimidin-5-yl)piperazine-1-carboxylate (60 mg, 0.166 mmol) and (S)—N-methyl-5,6,7,8-tetrahydroquinolin-8-amine (40.4 mg, 0.249 mmol) in DCE (1.5 mL) was charged with sodium triacetoxyborohydride (52.8 mg, 0.249 mmol). After stirring rt 1 h, the reaction mixture was diluted with ethyl acetate, washed with saturated aqueous sodium bicarbonate solution, dried over anhydrous sodium sulfate, filtered, and concentrated in vacuo. The residue was purified by flash chromatography using an Isco 40 g column eluting with 0-10% MeOH/DCM containing 2N ammonia to give the product (58 mg, 69% yield) as a yellow oil. $^1$H NMR (400 MHz, METHANOL-$d_4$) δ 8.45 (d, J=4 Hz, 1H), 8.38 (d, J=4 Hz, 1H), 7.75 (s, 1H), 7.56-7.52 (m, 2H), 7.22-7.19 (m, 2H), 6.29 (s, 1H), 4.10-4.08 (m, 1H), 3.92 (s, 3H), 3.78 (d, J=8 Hz, 2H), 3.70-3.68 (m, 4H), 3.52-3.49 (m, 4H), 2.85-2.78 (m, 2H), 2.50 (s, 3H), 2.34-1.76 (m, 4H), 1.52 (s, 9H); MS (ESI$^+$) m/z 508.2 (M+H)$^+$.

G) (S)—N-((7-Methoxy-5-(piperazin-1-yl)imidazo[1,2-c]pyrimidin-2-yl)methyl)-N-methyl-5,6,7,8-tetrahydroquinolin-8-amine To a solution of (S)-tert-butyl 4-(7-methoxy-2-((methyl(5,6,7,8-tetrahydroquinolin-8-yl)amino)methyl)imidazo[1,2-c]pyrimidin-5-yl)piperazine-1-carboxylate (58 mg, 0.114 mmol) in DCM (1 mL) was added TFA (1 mL). After stirring at rt for 1 h, the reaction mixture was concentrated in vacuo. The residue was purified by flash chromatography using an Isco 40 g column eluting with 0-10% MeOH/DCM containing 2N ammonia. The desired fractions were combined, concentrated in vacuo, and then lyophilized from acetonitrile/water to give the title compound (26 mg, 53% yield) as a white solid. $^1$H NMR (400 MHz, METHANOL-$d_4$) δ 8.44 (d, J=4 Hz, 1H), 7.70 (s, 1H), 7.53 (dd, J=8, 4 Hz, 1H), 7.20 (dd, J=8, 4 Hz, 1H), 6.27 (s, 1H), 4.09-4.05 (m, 1H), 3.92 (s, 3H), 3.79 (q, J=8 Hz, 2H), 3.52-3.49 (m, 4H), 3.09-3.07 (m, 4H), 2.88-2.78 (m, 2H), 2.34 (s, 3H), 2.10-2.00 (m, 3H), 1.78-1.70 (m, 1H); MS (ESI$^+$) m/z 408.2 (M+H)$^+$.

Example 105

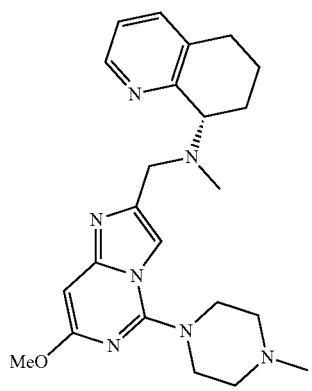 [SMILES: COc1cc2nc(CN(C)[C@H]3CCCc4cccnc43)cn2c(N2CCN(C)CC2)n1]

(S)—N-((7-Methoxy-5-(4-methylpiperazin-1-yl)imidazo[1,2-c]pyrimidin-2-yl)methyl)-N-methyl-5,6,7,8-tetrahydroquinolin-8-amine A solution of (S)—N-((7-methoxy-5-(piperazin-1-yl)imidazo[1,2-c]pyrimidin-2-yl)methyl)-N-methyl-5,6,7,8-tetrahydroquinolin-8-amine (20 mg, 0.049 mmol, Example 104) in DCE (2 mL) was charged with formaldehyde, 37% aq (0.027 mL, 0.982 mmol) and acetic acid (0.2 mL). Solid sodium triacetoxyborohydride (20.8 mg, 0.098 mmol) was then added. After stirring at rt 30 min, the reaction was concentrated in vacuo. The residue was purified by flash chromatography using an Isco 40 g column eluting with 0-20% MeOH/DCM containing 2N ammonia. The desired fractions were combined, concentrated in vacuo, and then lyophilized from acetonitrile/water to give the title compound (13 mg, 57% yield) as a white solid. $^1$H NMR (400 MHz, METHANOL-$d_4$) δ 8.45 (d, J=4 Hz, 1H), 7.72 (s, 1H), 7.57 (dd, J=8, 4, Hz, 1H), 7.24 (dd, J=8, 4 Hz, 1H), 6.31 (s, 1H), 3.95 (s, 3H), 3.93-3.90 (m, 2H), 3.60-3.56 (m, 4H), 2.91-2.72 (m, 6H), 2.43 (s, 6H), 2.24-2.03 (m, 3H), 1.78-1.70 (m, 1H); MS (ESI$^+$) m/z 422.2 (M+H)$^+$.

Example 106

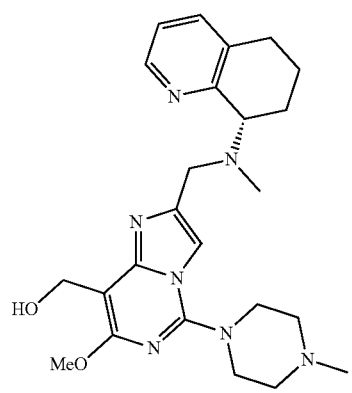 [SMILES: COc1nc(N2CCN(C)CC2)n2cc(CN(C)[C@H]3CCCc4cccnc43)nc2c1CO]

(S)-(7-Methoxy-2-((methyl(5,6,7,8-tetrahydroquinolin-8-yl)amino)methyl)-5-(4-methylpiperazin-1-yl)imidazo[1,2-c]pyrimidin-8-yl)methanol In EXAMPLE 105, further elution of the Isco column with 0-20% MeOH/DCM containing 2N ammonia gave the product. The desired fractions were combined, concentrated in vacuo, and then lyophilized from acetonitrile/water to give the title compound (8 mg, 34% yield) as a white solid. $^1$H NMR (400 MHz, METHANOL-$d_4$) δ 8.45 (d, J=4 Hz, 1H), 7.73 (s, 1H), 7.54 (dd, J=8, 4, Hz, 1H), 7.21 (dd, J=8, 4 Hz, 1H), 4.84 (s, 2H), 4.12-4.09 (m, 1H), 4.03 (s, 3H), 3.87-3.83 (m, 2H), 3.62-3.60 (m, 4H), 2.89-2.72 (m, 6H), 2.43 (s, 3H), 2.38 (s, 3H), 2.15-2.01 (m, 3H), 1.78-1.70 (m, 1H); MS (ESI$^+$) m/z 452.2 (M+H)$^+$.

Example 107

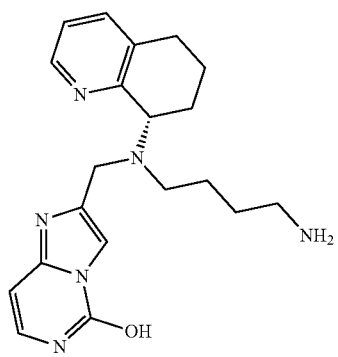 [SMILES: NCCCCN(Cc1cn2c(O)nccc2n1)[C@H]1CCCc2cccnc21]

(S)-2-(((4-Aminobutyl)(5,6,7,8-tetrahydroquinolin-8-yl)amino)methyl)imidazo[1,2-c]pyrimidin-5-ol

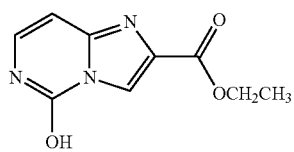 [SMILES: CCOC(=O)c1cn2c(O)nccc2n1]

A) Ethyl 5-hydroxyimidazo[1,2-c]pyrimidine-2-carboxylate

A 250 mL round bottom flask was charged with ethyl 7-chloro-5-hydroxyimidazo[1,2-c]pyrimidine-2-carboxylate (2.9 g, 12.2 mmol, Step A of Example 72) and MeOH (50 mL). The flask was flushed with nitrogen and then 10% Pd/C (343 mg, 0.244 mmol) was added. The reaction was stirred under an atmosphere of hydrogen (balloon) for 3 days. The palladium catalyst was removed by filtration and the filtrate concentrated to give a yellow solid. The solid was suspended in MeOH and filtered to give the crude product (997 mg, 39% yield) as a white solid. $^1$H NMR (400 MHz, DMSO-$d_6$) δ 11.84 (br s, 1H), 8.27 (s, 1H), 7.38 (d, J=8 Hz, 1H), 6.62 (d, J=8 Hz, 1H), 4.30 (q, J=8 Hz, 2H), 1.31 (t, J=8 Hz, 3H); MS (ESI$^+$) m/z 208.1 (M+H)$^+$.

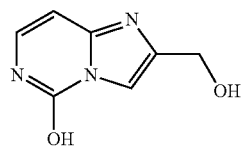 [SMILES: OCc1cn2c(O)nccc2n1]

B) 2-(Hydroxymethyl)imidazo[1,2-c]pyrimidin-5-ol

To a solution of ethyl 5-hydroxyimidazo[1,2-c]pyrimidine-2-carboxylate (345 mg, 1.67 mmol) in THF (10 mL) at 0° C. was added LAH (2.5 mL, 2.5 mmol). After stirring at rt overnight, a second shot (1.5 eq, 2.5 mL) of LAH was added. After stirring at rt for 4 h, the reaction mixture was quenched with wet sodium sulfate. After the bubbling stopped, the reaction was filtered and the solid was washed with copious warm 20% MeOH/DCM. The filtrate was concentrated in vacuo. The residue was purified by flash chromatography using an Isco 40 g column eluting with 0-20% MeOH/DCM to give the product (155 mg, 56% yield) as a yellow solid. $^1$H NMR (400 MHz, DMSO-$d_6$) δ 11.46 (br s, 1H), 7.54 (s, 1H), 7.23 (d, J=8 Hz, 1H), 6.50 (d, J=8 Hz, 1H), 5.26 (t, J=6 Hz), 4.48 (d, J=6 Hz, 2H); MS (ESI$^+$) m/z 166.1 (M+H)$^+$.

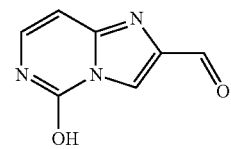 [SMILES: O=Cc1cn2c(O)nccc2n1]

C) 5-Hydroxyimidazo[1,2-c]pyrimidine-2-carbaldehyde

To a solution of 2-(hydroxymethyl)imidazo[1,2-c]pyrimidin-5-ol (150 mg, 0.91 mmol) in DCM (5 mL) was added manganese dioxide (395 mg, 4.5 mmol). After stirring at 40° C. for 2 h, a second shot of manganese dioxide was added (5 eq). After stirring at rt 1 h, the reaction mixture was filtered through a pad of celite to give the crude product (82 mg, 55% yield) as a tan solid. MS (ESI$^+$) m/z 164.1 (M+H)$^+$.

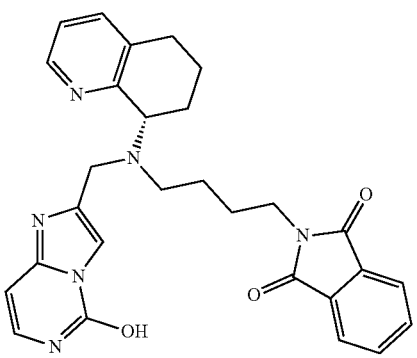 [SMILES: O=C1c2ccccc2C(=O)N1CCCCN(Cc1cn2c(O)nccc2n1)[C@H]1CCCc2cccnc21]

D) (S)-2-(4-(((5-Hydroxyimidazo[1,2-c]pyrimidin-2-yl)methyl)(5,6,7,8-tetrahydroquinolin-8-yl)amino)butyl)isoindoline-1,3-dione A mixture of 5-hydroxyimidazo[1,2-c]pyrimidine-2-carbaldehyde (17 mg, 0.104 mmol) and (S)-2-(4-((5,6,7,8- tetrahydroquinolin-8-yl)amino)butyl)isoindoline-1,3-dione (54.6 mg, 0.156 mmol) in DCE (2 mL) was charged with sodium triacetoxyborohydride (33.1 mg, 0.156 mmol). After stirring rt 1 h, LCMS indicated no reaction. MeOH (1 mL) was added to solubilize the reaction mixture. After stirring at rt 1 h, LCMS indicated the desired product. The crude reaction mixture was diluted with ethyl acetate, washed with saturated aqueous sodium bicarbonate solution, dried over anhydrous sodium sulfate, filtered, and concentrated in vacuo. The residue was purified directly by flash chromatography using an Isco 40 g column eluting with 0-10% MeOH/DCM containing 2N ammonia to give the product (21 mg, 41% yield) as a colorless oil. $^1$H NMR (400 MHz, METHANOL-$d_4$) δ 8.36 (d, J=4 Hz, 1H), 7.84-7.78 (m, 4H), 7.74 (s, 1H), 7.42 (d, J=4 Hz, 1H), 7.19 (d, J=8 Hz, 1H), 7.11 (d, J=4 Hz, 1H), 6.48 (d, J=8 Hz, 1H), 4.12-4.08 (m, 1H), 3.87-3.79 (m, 2H), 3.58 (t, J=8 Hz, 2H), 2.90-2.70 (m, 4H), 2.12-2.00 (m, 3H), 1.65-1.61 (m, 3H), 1.43-1.40 (m, 2H); MS (ESI$^+$) m/z 497.2 (M+H)$^+$.

E) (S)-2-(((4-Aminobutyl)(5,6,7,8-tetrahydroquinolin-8-yl)amino)methyl)imidazo[1,2-c]pyrimidin-5-ol To a solution of (S)-2-(4-(((5-hydroxyimidazo[1,2-c]pyrimidin-2-yl)methyl)(5,6,7,8-tetrahydroquinolin-8-yl)amino)butyl)isoindoline-1,3-dione (21 mg, 0.042 mmol) in EtOH (1 mL) was added hydrazine (0.023 mL, 0.254 mmol) (35% aq.). After stirring at rt 2 h, the reaction mixture was purified by flash chromatography using an Isco 40 g column eluting with 0-10% MeOH/DCM containing 2N ammonia to give the title compound (17 mg, 100% yield) as a white solid. $^1$H NMR (400 MHz, METHANOL-$d_4$) δ 8.52 (d, J=4 Hz, 1H), 7.91 (s, 1H), 7.71 (d, J=4 Hz, 1H), 7.39-7.36 (m, 1H), 7.30 (d, J=8 Hz, 1H), 6.62 (d, J=8 Hz, 1H), 4.68-4.66 (m, 1H), 4.35-4.31 (m, 2H), 3.30-3.21 (m, 1H), 3.03-2.89 (m, 5H), 2.55-2.48 (m, 1H), 2.25-2.12 (m, 2H), 1.90-1.70 (m, 5H); MS (ESI$^+$) m/z 367.2 (M+H)$^+$.

Example 108

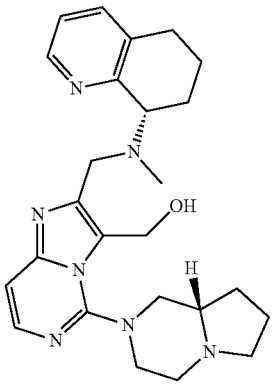 [SMILES: CN(Cc1nc2ccnc(N3CCN4CCC[C@H]4C3)n2c1CO)[C@H]1CCCc2cccnc21]

(5-((S)-Hexahydropyrrolo[1,2-a]pyrazin-2(1H)-yl)-2-((methyl((S)-5,6,7,8-tetrahydroquinolin-8-yl)amino)methyl)imidazo[1,2-c]pyrimidin-3-yl)methanol A solution of (S)—N-((5-((S)-hexahydropyrrolo[1,2-a]pyrazin-2(1H)-yl)imidazo[1,2-c]pyrimidin-2-yl)methyl)-N-methyl-5,6,7,8-tetrahydroquinolin-8-amine (80 mg, 0.192 mmol) in acetic acid (2 mL) was charged with formaldehyde, 37% aq (1 mL, 36.3 mmol). After stirring at 60° C. for 2 days, the reaction was concentrated in vacuo. The residue was filtered to remove polymerized formaldehyde and then purified by flash chromatography using an Isco 40 g column eluting with 0-15% MeOH/DCM containing 2N ammonia to give the impure product (57 mg) as a colorless oil. The impure product was dissolved in MeOH and then purified a second time by prep hplc using a C18 Phen Luna Axia 21.20×250 mm column eluting with 0-100% solvent A/B over a 30 minute gradient (Solvent A: 95% H$_2$O/5% MeCN/10 mM NH$_4$OAc; Solvent B: 5% H$_2$O/95% MeCN/10 mM NH$_4$OAc). The product eluted at 19.5 min. The desired fractions were combined and then lyophilized to give the title compound (30 mg, 0.066 mmol, 34% yield) as a white sticky solid. $^1$H NMR (400 MHz, METHANOL-$d_4$) δ 8.40 (d, J=4 Hz, 1H), 7.79 (d, J=4 Hz, 1H), 7.57 (d, J=4, 1 Hz, 1H), 7.24-7.19 (m, 2H), 5.20 (d, J=8 Hz, 2H), 4.22-4.10 (m, 3H), 3.92-3.90 (m, 1H), 3.75-3.70 (m, 1H), 3.33-3.25 (m, 3H), 2.95-2.47 (m, 6H), 2.31 (s, 3H), 2.20-1.55 (m, 8H); MS (ES): m/z=448.1 (M+H)$^+$.

Biological Assays

Exemplary compounds of the invention were tested for their ability to induce or inhibit calcium flux in CCRF-CEM cells. Experimental procedures and results are provided below. The exemplified biological assays, which follow, have been carried out with compounds of the invention and/or salts thereof.

CXCR4-CEM Calcium Flux Assays.

Human T lymphoblast cells (CCRF-CEM) expressing endogenous CXCR4 receptors were grown in suspension culture and plated in clear bottom 384-well microplates (Greiner bio-one Cat#789146) in assay buffer [Hank's Buffered Saline Solution (Gibco Cat#14025-092) supplemented with 20 mM HEPES (Gibco Cat#15630-080) and 0.1% fatty-acid free BSA (Sigma Cat# A9205)] at 40,000 cells per well. The cells were loaded with equal volume of calcium indicator dye (AAT Bioquest Inc, Cat#34601) for 30 minutes at 37° C. The cells were then equilibrated to room temperature for 30 minutes before assay. Test compounds solubilized and serially diluted in DMSO were transferred to 384 well plates (Matrix Cat#4307). The serially diluted compounds were diluted to working concentrations with the same assay buffer to 0.5% DMSO. They were added to the cells by FDSS6000 (Hamamatsu) at final concentrations ranging from 25,000 nM to 0.423 nM. Activity of the compounds to induce calcium flux was monitored by FDSS in the "agonist mode" for 90 sec. For "antagonist mode" assessment, the cells are subsequently incubated for 25 min at room temperature. SDF-1α (R&D System Cat#350-NS/CF) was then added at a final concentration of 4 nM to stimulate the cells. Inhibition of SDF-1α-induced calcium flux was monitored by FDSS6000 for 90 sec.

Activation data for the test compound over a range of concentrations was plotted as percentage activation of the test compound (100%=maximum response triggered by a saturating concentration of SDF-1α, i.e., 160 nM). After correcting for background, EC$_{50}$ values were determined. The EC$_{50}$ is defined as the concentration of test compound which produces 50% of the maximal response and was quantified using the 4-parameter logistic equation to fit the data. Inhibition data for the test compound over a range of concentrations was plotted as percentage inhibition of the test compound as compared to an internal control compound. The IC$_{50}$ is defined as the concentration of test compound which inhibits 50% of the maximal response and was quantified using the 4-parameter logistic equation to fit the data.

None of the compounds tested demonstrated agonist activity in the calcium flux assay. All compounds demonstrated EC50's of >30 uM. In contrast, compounds demonstrated a range of potencies in inhibiting SDF-1α-induced calcium flux as shown in the table below.

TABLE

| Example Number | IC$_{50}$ (μM) |
| --- | --- |
| 3 | >30 |
| 4 | 0.0025 |
| 5 | 0.0081 |
| 6 | 0.0038 |
| 7 | 0.0024 |
| 8 | 0.089 |
| 9 | 25.5 |
| 10 | 8.60 |
| 11 | 0.013 |
| 12 | 0.054 |
| 13 | 5.67 |
| 14 | 1.23 |
| 15 | 0.75 |
| 16 | 0.54 |
| 17 | 0.0037 |
| 18 | 0.014 |
| 19 | 0.014 |
| 20 | 0.0096 |
| 21 | 0.017 |
| 22 | 0.042 |
| 23 | 0.77 |
| 24 | 0.011 |
| 25 | 0.012 |
| 26 | 0.014 |
| 27 | 0.075 |
| 28 | 0.011 |
| 29 | 0.077 |
| 30 | 0.19 |
| 31 | 0.17 |
| 32 | 0.31 |
| 33 | 1.0 |
| 34 | 0.12 |
| 35 | 0.51 |
| 36 | 30.7 |
| 37 | 0.023 |
| 38 | 0.42 |
| 39 | 0.063 |
| 40 | 14.4 |
| 41 | 7.50 |
| 42 | 22.7 |
| 43 | 0.13 |
| 44 | 9.36 |
| 45 | 0.066 |
| 46 | 0.0073 |
| 47 | 0.0097 |
| 48 | 0.30 |
| 49 | 0.0028 |
| 50 | 0.092 |
| 51 | 0.006 |
| 52 | 0.0029 |
| 53 | 0.017 |
| 54 | 0.0056 |
| 55 | 0.009 |
| 56 | 0.0046 |
| 57 | 0.028 |
| 58 | 0.060 |
| 59 | 0.025 |
| 60 | 0.0076 |
| 61 | 0.033 |
| 62 | 19.6 |
| 63 | 16.7 |
| 64 | 0.011 |
| 65 | 0.016 |
| 66 | 0.0094 |
| 67 | 0.042 |
| 68 | 0.050 |
| 69 | 0.0038 |
| 70 | 0.0042 |
| 71 | 0.0027 |
| 72 | 0.33 |
| 73 | 0.12 |
| 74 | 0.079 |
| 75 | 0.011 |
| 76 | 0.0064 |
| 77 | 0.25 |
| 78 | 0.011 |
| 79 | 0.056 |
| 80 | 0.023 |
| 81 | 0.032 |
| 82 | 3.78 |
| 83 | 0.15 |
| 84 | >16 |
| 85 | 0.0017 |
| 86 | 0.0017 |
| 87 | 0.20 |
| 88 | 0.22 |
| 89 | 0.28 |
| 90 | 0.0025 |
| 91 | >30 |
| 92 | 0.29 |
| 93 | 0.027 |
| 94 | 0.065 |
| 95 | 0.024 |
| 96 | 0.22 |
| 97 | 0.48 |
| 98 | 0.0019 |
| 99 | 0.027 |
| 100 | 0.21 |
| 101 | 0.22 |
| 102 | 0.21 |
| 103 | 0.26 |
| 104 | 0.19 |
| 105 | 0.10 |
| 106 | 0.37 |
| 107 | 0.029 |
| 108 | 0.0021 |

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

The invention claimed is:
1. A compound of Formula I

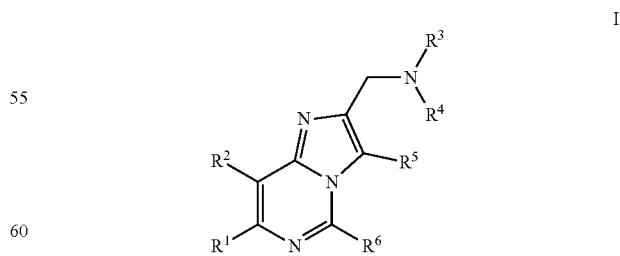

where:
R$^1$ is hydrogen, cyano, halo, alkyl, haloalkyl, hydroxyalkyl, alkoxyalkyl, alkoxy, and haloalkoxy;
R$^2$ is hydrogen, cyano, halo, alkyl, haloalkyl, hydroxyalkyl, alkoxyalkyl, alkoxy, and haloalkoxy;

$R^3$ is tetrahydroquinolinyl, dihydropyranopyridinyl, tetrahydrocinnolinyl, tetrahydroquinazolinyl, or tetrahydroquinoxalinyl, and is substituted with 0-3 substituents selected from halo, alkyl, haloalkyl, alkoxy, and haloalkoxy;

$R^4$ is hydrogen, alkyl, hydroxyalkyl, alkoxyalkyl, ($R^7$)alkyl, (($R^7$)cycloalkyl)alkyl, ((($R^7$)alkyl)cycloalkyl)alkyl, ($R^7$)cycloalkyl, or (($R^7$)alkyl)cycloalkyl;

$R^5$ is hydrogen, halo, alkyl, haloalkyl, hydroxyalkyl, alkoxyalkyl, alkoxy, haloalkoxy, ($R^7$)alkyl, (($R^7$)cycloalkyl)alkyl, ((($R^7$)alkyl)cycloalkyl)alkyl, ($R^7$)cycloalkyl, or (($R^7$)alkyl)cycloalkyl;

$R^6$ is hydrogen, alkyl, hydroxy, alkoxy, alkylthio, ($R^7$)alkyl, (($R^7$)cycloalkyl)alkyl, ((($R^7$)alkyl)cycloalkyl)alkyl, ($R^7$)cycloalkyl, or (($R^7$)alkyl)cycloalkyl;

or $R^6$ is azetidinyl, pyrrolidinyl, piperidinyl, piperazinyl, morpholinyl, homopiperidinyl, homopiperazinyl, diazabicycloheptanyl, octahydropyrrolopyrrolyl, octahydropyrrolopyrazinyl, octahydropyrrolopyridinyl, octahydropyridopyrazinyl, octahydropyrazinooxazinyl, or tetrahydrotriazolopyrazinyl, and is substituted with 0-4 substituents selected from halo, alkyl, (cycloalkyl)alkyl, (tetrahydropyranyl)alkyl, haloalkyl, hydroxyalkyl, alkoxyalkyl, ($R^7$)alkyl, carboxyalkyl, (alkoxycarbonyl)alkyl, ($Ar^1$)alkyl, diphenylalkyl, cycloalkyl, alkylcarbonyl, alkoxycarbonyl, ($R^7$)NCO, ($Ar^2$)aminocarbonyl, alkylsulfonyl, ($Ar^2$)sulfonyl, and $Ar^2$, and is also substituted with 0-3 halo or alkyl substituents;

$R^7$ is ($R^8$)($R^9$)N;

or $R^7$ is azetidinyl, pyrrolidinyl, piperidinyl, piperazinyl, morpholinyl, homopiperidinyl, homopiperazinyl, or octahydropyrrolopyrazinyl, and is substituted with 0-3 halo or alkyl substituents;

$R^8$ is hydrogen or alkyl;

$R^9$ is hydrogen or alkyl;

$Ar^1$ is pyrrolyl, furanyl, thienyl, pyrazolyl, isoxazolyl, isothiazolyl, imidazoyl, oxazolyl, thiazolyl, triazolyl, oxadiazolyl, thiadiazolyl, tetrazolyl, pyridinyl, pyridazinyl, pyrimidinyl, pyrazinyl, phenyl, or biphenyl and is substituted with 0-3 substituents selected from cyano, halo, alkyl, haloalkyl, hydroxy, alkoxy, haloalkoxy, phenoxy, and $R^7$; and $Ar^2$ is phenyl, pyridinyl, or thienyl and is substituted with 0-3 substituents selected from halo, alkyl, haloalkyl, alkoxy, and haloalkoxy;

or a pharmaceutically acceptable salt thereof.

2. A compound of claim 1 where:

$R^1$ is hydrogen, cyano, halo, alkyl, haloalkyl, hydroxyalkyl, alkoxyalkyl, alkoxy, and haloalkoxy;

$R^2$ is hydrogen, cyano, halo, alkyl, haloalkyl, hydroxyalkyl, alkoxyalkyl, alkoxy, and haloalkoxy;

$R^3$ is tetrahydroquinolinyl, dihydropyranopyridinyl, tetrahydrocinnolinyl, tetrahydroquinazolinyl, or tetrahydroquinoxalinyl, and is substituted with 0-3 substituents selected from halo, alkyl, haloalkyl, alkoxy, and haloalkoxy;

$R^4$ is hydrogen, alkyl, hydroxyalkyl, alkoxyalkyl, ($R^7$)alkyl, (($R^7$)cycloalkyl)alkyl, ((($R^7$)alkyl)cycloalkyl)alkyl, ($R^7$)cycloalkyl, or (($R^7$)alkyl)cycloalkyl;

$R^5$ is hydrogen, halo, alkyl, haloalkyl, hydroxyalkyl, alkoxyalkyl, alkoxy, haloalkoxy, ($R^7$)alkyl, (($R^7$)cycloalkyl)alkyl, ((($R^7$)alkyl)cycloalkyl)alkyl, ($R^7$)cycloalkyl, or (($R^7$)alkyl)cycloalkyl;

$R^6$ is hydrogen, alkyl, hydroxy, alkoxy, alkylthio, ($R^7$)alkyl, (($R^7$)cycloalkyl)alkyl, ((($R^7$)alkyl)cycloalkyl)alkyl, ($R^7$)cycloalkyl, or (($R^7$)alkyl)cycloalkyl;

or $R^6$ is azetidinyl, pyrrolidinyl, piperidinyl, piperazinyl, morpholinyl, homopiperidinyl, homopiperazinyl, octahydropyrrolopyrazinyl, or octahydropyridopyrazinyl, and is substituted with 0-4 substituents selected from alkyl, (cycloalkyl)alkyl, (tetrahydropyranyl)alkyl, haloalkyl, hydroxyalkyl, alkoxyalkyl, ($R^7$)alkyl, carboxyalkyl, (alkoxycarbonyl)alkyl, ($Ar^1$)alkyl, diphenylalkyl, cycloalkyl, $R^7$, alkylcarbonyl, alkoxycarbonyl, ($R^7$)NCO, ($Ar^2$)aminocarbonyl, alkylsulfonyl, and ($Ar^2$)sulfonyl, and is also substituted with 0-3 halo or alkyl substituents;

$R^7$ is ($R^8$)($R^9$)N;

or $R^7$ is azetidinyl, pyrrolidinyl, piperidinyl, piperazinyl, morpholinyl, homopiperidinyl, homopiperazinyl, or octahydropyrrolopyrazinyl, and is substituted with 0-3 halo or alkyl substituents;

$R^8$ is hydrogen or alkyl;

$R^9$ is hydrogen or alkyl;

$Ar^1$ is pyrrolyl, furanyl, thienyl, pyrazolyl, isoxazolyl, isothiazolyl, imidazoyl, oxazolyl, thiazolyl, triazolyl, oxadiazolyl, thiadiazolyl, tetrazolyl, pyridinyl, pyridazinyl, pyrimidinyl, pyrazinyl, phenyl, or biphenyl and is substituted with 0-3 substituents selected from cyano, halo, alkyl, haloalkyl, hydroxy, alkoxy, haloalkoxy, phenoxy, and $R^7$; and $Ar^2$ is phenyl, pyridinyl, or thienyl and is substituted with 0-3 substituents selected from halo, alkyl, haloalkyl, alkoxy, and haloalkoxy;

or a pharmaceutically acceptable salt thereof.

3. A compound of claim 1 where:

$R^1$ is hydrogen, halo, alkyl, haloalkyl, alkoxy, or haloalkoxy;

$R^2$ is hydrogen, halo, alkyl, haloalkyl, alkoxy, or haloalkoxy;

$R^3$ is tetrahydroquinolinyl or dihydropyranopyridinyl, and is substituted with 0-3 substituents selected from halo, alkyl, haloalkyl, alkoxy, and haloalkoxy;

$R^4$ is hydrogen, alkyl, hydroxyalkyl, alkoxyalkyl, or ($R^7$)alkyl;

$R^5$ is hydrogen, halo, alkyl, haloalkyl, hydroxyalkyl, alkoxyalkyl, alkoxy, or haloalkoxy;

$R^6$ is hydrogen, alkyl, alkoxy, or alkylthio;

or $R^6$ is azetidinyl, pyrrolidinyl, piperidinyl, piperazinyl, morpholinyl, homopiperidinyl, or homopiperazinyl, and is substituted with 0-1 substituents selected from halo, alkyl, (cycloalkyl)alkyl, (tetrahydropyranyl)alkyl, haloalkyl, hydroxyalkyl, alkoxyalkyl, ($R^7$)alkyl, carboxyalkyl, (alkoxycarbonyl)alkyl, ($Ar^1$)alkyl, diphenylalkyl, cycloalkyl, alkylcarbonyl, alkoxycarbonyl, alkylaminocarbonyl, ($Ar^2$)aminocarbonyl, alkylsulfonyl, ($Ar^2$)sulfonyl, and $Ar^2$, and is also substituted with 0-3 halo or alkyl substituents;

$R^7$ is ($R^8$)($R^9$)N;

or $R^7$ is azetidinyl, pyrrolidinyl, piperidinyl, piperazinyl, morpholinyl, homopiperidinyl, or homopiperazinyl and is substituted with 0-3 halo or alkyl substituents;

$R^8$ is hydrogen or alkyl;

$R^9$ is hydrogen or alkyl;

$Ar^1$ is pyrrolyl, furanyl, thienyl, pyrazolyl, isoxazolyl, isothiazolyl, imidazoyl, oxazolyl, thiazolyl, triazolyl, oxadiazolyl, thiadiazolyl, tetrazolyl, pyridinyl, pyridazinyl, pyrimidinyl, pyrazinyl, phenyl, or biphenyl and is substituted with 0-3 substituents selected from cyano, halo, alkyl, haloalkyl, hydroxy, alkoxy, haloalkoxy, phenoxy, and $R^7$; and Ar² is phenyl, pyridinyl, or thienyl and is substituted with 0-3 substituents selected from halo, alkyl, haloalkyl, alkoxy, and haloalkoxy;

or a pharmaceutically acceptable salt thereof.

4. A compound of claim 2 where R¹ is hydrogen; R¹ is hydrogen; R³ is tetrahydroquinolinyl or dihydropyranopyridinyl; R⁴ is alkyl; R⁵ is hydrogen; R⁶ is azetidinyl, pyrrolidinyl, piperidinyl, piperazinyl, morpholinyl, homopiperidinyl, or homopiperazinyl, and is substituted with 0-1 substituents selected from halo, alkyl, (cycloalkyl)alkyl, (tetrahydropyranyl)alkyl, haloalkyl, hydroxyalkyl, alkoxyalkyl, (R⁷)alkyl, carboxyalkyl, (alkoxycarbonyl)alkyl, (Ar¹)alkyl, diphenylalkyl, cycloalkyl, R⁷, alkylcarbonyl, alkoxycarbonyl, alkylaminocarbonyl, (Ar²)aminocarbonyl, alkylsulfonyl, and (Ar²)sulfonyl, and Ar², and is also substituted with 0-3 halo or alkyl substituents; R⁷ is (R⁸)(R⁹)N or R⁷ is azetidinyl, pyrrolidinyl, piperidinyl, piperazinyl, morpholinyl, homopiperidinyl, or homopiperazinyl and is substituted with 0-3 halo or alkyl substituents; R⁸ is hydrogen or alkyl; R⁹ is hydrogen or alkyl; Ar¹ is pyrrolyl, furanyl, thienyl, pyrazolyl, isoxazolyl, isothiazolyl, imidazoyl, oxazolyl, thiazolyl, triazolyl, oxadiazolyl, thiadiazolyl, tetrazolyl, pyridinyl, pyridazinyl, pyrimidinyl, pyrazinyl, phenyl, or biphenyl and is substituted with 0-3 substituents selected from cyano, halo, alkyl, haloalkyl, hydroxy, alkoxy, haloalkoxy, phenoxy, and (R⁸)(R⁹)N; and Ar² is phenyl, pyridinyl, or thienyl and is substituted with 0-3 substituents selected from halo, alkyl, haloalkyl, alkoxy, and haloalkoxy; or a pharmaceutically acceptable salt thereof.

5. A compound of claim 3 where R¹ is hydrogen; R² is hydrogen; R³ is tetrahydroquinolinyl or dihydropyranopyridinyl; R⁴ is alkyl; R⁵ is hydrogen; R⁶ is piperazinyl substituted with 0-1 substituents selected from halo, alkyl, (cycloalkyl)alkyl, (tetrahydropyranyl)alkyl, haloalkyl, hydroxyalkyl, alkoxyalkyl, (R⁷)alkyl, carboxyalkyl, (alkoxycarbonyl)alkyl, (Ar¹)alkyl, diphenylalkyl, cycloalkyl, R⁷, alkylcarbonyl, alkoxycarbonyl, alkylaminocarbonyl, (Ar²)aminocarbonyl, alkylsulfonyl, and (Ar²)sulfonyl, and Ar², and is also substituted with 0-3 halo or alkyl substituents; R⁷ is (R⁸)(R⁹)N or R⁷ is azetidinyl, pyrrolidinyl, piperidinyl, piperazinyl, morpholinyl, homopiperidinyl, or homopiperazinyl and is substituted with 0-3 halo or alkyl substituents; R⁸ is hydrogen or alkyl; R⁹ is hydrogen or alkyl; Ar¹ is pyrrolyl, furanyl, thienyl, pyrazolyl, isoxazolyl, isothiazolyl, imidazoyl, oxazolyl, thiazolyl, triazolyl, oxadiazolyl, thiadiazolyl, tetrazolyl, pyridinyl, pyridazinyl, pyrimidinyl, pyrazinyl, phenyl, or biphenyl and is substituted with 0-3 substituents selected from cyano, halo, alkyl, haloalkyl, hydroxy, alkoxy, haloalkoxy, phenoxy, and R⁷; and Ar² is phenyl, pyridinyl, or thienyl and is substituted with 0-3 substituents selected from halo, alkyl, haloalkyl, alkoxy, and haloalkoxy; or a pharmaceutically acceptable salt thereof.

6. A compound of claim 1 where R³ is tetrahydroquinolinyl or dihydropyranopyridinyl.

7. A compound of claim 1 where R⁶ is azetidinyl, pyrrolidinyl, piperidinyl, piperazinyl, morpholinyl, homopiperidinyl, or homopiperazinyl, and is substituted with 0-1 substituents selected from halo, alkyl, (cycloalkyl)alkyl, (tetrahydropyranyl)alkyl, haloalkyl, hydroxyalkyl, alkoxyalkyl, (R⁷)alkyl, carboxyalkyl, (alkoxycarbonyl)alkyl, (Ar¹)alkyl, diphenylalkyl, cycloalkyl, R⁷, alkylcarbonyl, alkoxycarbonyl, alkylaminocarbonyl, (Ar²)aminocarbonyl, alkylsulfonyl, and (Ar²)sulfonyl, and Ar², and is also substituted with 0-3 halo or alkyl substituents.

8. A compound of claim 1 where R⁶ is piperazinyl substituted with 0-1 substituents selected from halo, alkyl, (cycloalkyl)alkyl, (tetrahydropyranyl)alkyl, haloalkyl, hydroxyalkyl, alkoxyalkyl, (R⁷)alkyl, carboxyalkyl, (alkoxycarbonyl)alkyl, (Ar¹)alkyl, diphenylalkyl, cycloalkyl, R⁷, alkylcarbonyl, alkoxycarbonyl, alkylaminocarbonyl, (Ar²)aminocarbonyl, alkylsulfonyl, and (Ar²)sulfonyl, and Ar², and is also substituted with 0-3 halo or alkyl substituents.

9. A compound of claim 1 selected from the group consisting of tert-Butyl 4-(2-formylimidazo[1,2-c]pyrimidin-5-yl)piperazine-1-carboxylate;

5-(4-Methylpiperazin-1-yl)imidazo[1,2-c]pyrimidine-2-carbaldehyde;

(S)-tert-Butyl 4-(2-((methyl(5,6,7,8-tetrahydroquinolin-8-yl)amino)methyl)imidazo[1,2-c]pyrimidin-5-yl)piperazine-1-carboxylate;

(S)—N-Methyl-N-((5-(4-methylpiperazin-1-yl)imidazo[1,2-c]pyrimidin-2-yl)methyl)-5,6,7,8-tetrahydroquinolin-8-amine;

(S)—N-Methyl-N-((5-(piperazin-1-yl)imidazo[1,2-c]pyrimidin-2-yl)methyl)-5,6,7,8-tetrahydroquinolin-8-amine;

(S)-(2-((Methyl(5,6,7,8-tetrahydroquinolin-8-yl)amino)methyl)-5-(piperazin-1-yl)imidazo[1,2-c]pyrimidin-3-yl)methanol;

(S)-(2-((Methyl(5,6,7,8-tetrahydroquinolin-8-yl)amino)methyl)-5-(4-methylpiperazin-1-yl)imidazo[1,2-c]pyrimidin-3-yl)methanol;

(S)—N-Methyl-N-((5-(methylthio)imidazo[1,2-c]pyrimidin-2-yl)methyl)-5,6,7,8-tetrahydroquinolin-8-amine;

(S)—N-Methyl-N-((5-morpholinoimidazo[1,2-c]pyrimidin-2-yl)methyl)-5,6,7,8-tetrahydroquinolin-8-amine;

(S)-1-(4-(2-((Methyl(5,6,7,8-tetrahydroquinolin-8-yl)amino)methyl)imidazo[1,2-c]pyrimidin-5-yl)piperazin-1-yl)ethanone;

(S)-2-(4-(2-((Methyl(5,6,7,8-tetrahydroquinolin-8-yl)amino)methyl)imidazo[1,2-c]pyrimidin-5-yl)piperazin-1-yl)ethanol;

(S)—N-((5-(4-(2-Fluoroethyl)piperazin-1-yl)imidazo[1,2-c]pyrimidin-2-yl)methyl)-N-methyl-5,6,7,8-tetrahydroquinolin-8-amine;

(S)-Methyl 4-(2-((methyl(5,6,7,8-tetrahydroquinolin-8-yl)amino)methyl)imidazo[1,2-c]pyrimidin-5-yl)piperazine-1-carboxylate;

(S)—N-ethyl-4-(2-((methyl(5,6,7,8-tetrahydroquinolin-8-yl)amino)methyl)imidazo[1,2-c]pyrimidin-5-yl)piperazine-1-carboxamide;

(S)—N-Methyl-N-((5-(4-(methylsulfonyl)piperazin-1-yl)imidazo[1,2-c]pyrimidin-2-yl)methyl)-5,6,7,8-tetrahydroquinolin-8-amine;

(S)—N-((5-(4-(2-Aminoethyl)piperazin-1-yl)imidazo[1,2-c]pyrimidin-2-yl)methyl)-N-methyl-5,6,7,8-tetrahydroquinolin-8-amine;

(S)—N-Methyl-N-((5-(4-(methyl-d3)piperazin-1-yl)imidazo[1,2-c]pyrimidin-2-yl)methyl)-5,6,7,8-tetrahydroquinolin-8-amine;

(S)—N-methyl-N-({5-[4-(2-phenylethyl)piperazin-1-yl]imidazo[1,2-c]pyrimidin-2-yl}methyl)-5,6,7,8-tetrahydroquinolin-8-amine;

(S)—N-methyl-N-({5-[4-(3-methylbutyl)piperazin-1-yl]imidazo[1,2-c]pyrimidin-2-yl}methyl)-5,6,7,8-tetrahydroquinolin-8-amine;

(S)—N-methyl-N-({5-[4-(propan-2-yl)piperazin-1-yl]imidazo[1,2-c]pyrimidin-2-yl}methyl)-5,6,7,8-tetrahydroquinolin-8-amine;

(8 S)—N-({5-[4-(cyclopropylmethyl)piperazin-1-yl]imidazo[1,2-c]pyrimidin-2-yl}methyl)-N-methyl-5,6,7,8-tetrahydroquinolin-8-amine;

(S)—N-methyl-N-({5-[4-(2-methylpropyl)piperazin-1-yl]imidazo[1,2-c]pyrimidin-2-yl}methyl)-5,6,7,8-tetrahydroquinolin-8-amine;

(S)—N-{[5-(4-cyclohexylpiperazin-1-yl)imidazo[1,2-c]pyrimidin-2-yl]methyl}-N-methyl-5,6,7,8-tetrahydroquinolin-8-amine;

4-({4-[2-({methyl[(S)-5,6,7,8-tetrahydroquinolin-8-yl]amino}methyl)imidazo[1,2-c]pyrimidin-5-yl]piperazin-1-yl}methyl)phenol;

(S)—N-[(5-{4-[(3-chlorophenyl)methyl]piperazin-1-yl}imidazo[1,2-c]pyrimidin-2-yl)methyl]-N-methyl-5,6,7,8-tetrahydroquinolin-8-amine;

(S)—N-methyl-N-({5-[4-(thiophen-2-ylmethyl)piperazin-1-yl]imidazo[1,2-c]pyrimidin-2-yl}methyl)-5,6,7,8-tetrahydroquinolin-8-amine;

(S)—N-methyl-N-[(5-{4-[(1-methyl-1H-imidazol-5-yl)methyl]piperazin-1-yl}imidazo[1,2-c]pyrimidin-2-yl)methyl]-5,6,7,8-tetrahydroquinolin-8-amine;

(S)—N-methyl-N-({5-[4-(pyridin-3-ylmethyl)piperazin-1-yl]imidazo[1,2-c]pyrimidin-2-yl}methyl)-5,6,7,8-tetrahydroquinolin-8-amine;

(S)—N-methyl-N-({5-[4-(pyridin-4-ylmethyl)piperazin-1-yl]imidazo[1,2-c]pyrimidin-2-yl}methyl)-5,6,7,8-tetrahydroquinolin-8-amine;

(S)—N-{[5-(4-cyclobutylpiperazin-1-yl)imidazo[1,2-c]pyrimidin-2-yl]methyl}-N-methyl-5,6,7,8-tetrahydroquinolin-8-amine;

(S)—N-({5-[4-(cyclopentylmethyl)piperazin-1-yl]imidazo[1,2-c]pyrimidin-2-yl}methyl)-N-methyl-5,6,7,8-tetrahydroquinolin-8-amine;

(S)—N-methyl-N-({5-[4-(oxolan-3-ylmethyl)piperazin-1-yl]imidazo[1,2-c]pyrimidin-2-yl}methyl)-5,6,7,8-tetrahydroquinolin-8-amine;

(S)—N-({5-[4-(2,2-dimethylpropyl)piperazin-1-yl]imidazo[1,2-c]pyrimidin-2-yl}methyl)-N-methyl-5,6,7,8-tetrahydroquinolin-8-amine;

(S)—N-methyl-N-({5-[4-(3-phenylpropyl)piperazin-1-yl]imidazo[1,2-c]pyrimidin-2-yl}methyl)-5,6,7,8-tetrahydroquinolin-8-amine;

(S)—N-{[5-(4-ethylpiperazin-1-yl)imidazo[1,2-c]pyrimidin-2-yl]methyl}-N-methyl-5,6,7,8-tetrahydroquinolin-8-amine;

(S)—N-methyl-N-({5-[4-(3,3,3-trifluoropropyl)piperazin-1-yl]imidazo[1,2-c]pyrimidin-2-yl}methyl)-5,6,7,8-tetrahydroquinolin-8-amine;

(S)—N-{[5-(4-benzylpiperazin-1-yl)imidazo[1,2-c]pyrimidin-2-yl]methyl}-N-methyl-5,6,7,8-tetrahydroquinolin-8-amine;

(S)—N-methyl-N-({5-[4-(1-methylpiperidin-4-yl)piperazin-1-yl]imidazo[1,2-c]pyrimidin-2-yl}methyl)-5,6,7,8-tetrahydroquinolin-8-amine;

(S)—N-({5-[4-(2,2-diphenylethyl)piperazin-1-yl]imidazo[1,2-c]pyrimidin-2-yl}methyl)-N-methyl-5,6,7,8-tetrahydroquinolin-8-amine;

(S)—N-methyl-N-({5-[4-(propane-2-sulfonyl)piperazin-1-yl]imidazo[1,2-c]pyrimidin-2-yl}methyl)-5,6,7,8-tetrahydroquinolin-8-amine;

(S)—N-methyl-N-({5-[4-(pyridine-3-sulfonyl)piperazin-1-yl]imidazo[1,2-c]pyrimidin-2-yl}methyl)-5,6,7,8-tetrahydroquinolin-8-amine;

(S)—N-({5-[4-(3-chlorobenzenesulfonyl)piperazin-1-yl]imidazo[1,2-c]pyrimidin-2-yl}methyl)-N-methyl-5,6,7,8-tetrahydroquinolin-8-amine;

4-[2-({methyl[(S)-5,6,7,8-tetrahydroquinohn-8-yl]amino}methyl)imidazo[1,2-c]pyrimidin-5-yl]-N-phenylpiperazine-1-carboxamide;

4-[2-({methyl[(S)-5,6,7,8-tetrahydroquinohn-8-yl]amino}methyl)imidazo[1,2-c]pyrimidin-5-yl]-N-(propan-2-yl)piperazine-1-carboxamide;

4-[2-({methyl[(S)-5,6,7,8-tetrahydroquinohn-8-yl]amino}methyl)imidazo[1,2-c]pyrimidin-5-yl]-N-(pyridin-3-yl)piperazine-1-carboxamide;

(S)—N-methyl-N-({5-[4-(2-phenylpropyl)piperazin-1-yl]imidazo[1,2-c]pyrimidin-2-yl}methyl)-5,6,7,8-tetrahydroquinolin-8-amine;

(S)—N-methyl-N-[(5-{4-[(4-phenylphenyl)methyl]piperazin-1-yl}imidazo[1,2-c]pyrimidin-2-yl)methyl]-5,6,7,8-tetrahydroquinolin-8-amine;

ethyl 2-{4-[2-({methyl[(S)-5,6,7,8-tetrahydroquinolin-8-yl]amino}methyl)imidazo[1,2-c]pyrimidin-5-yl]piperazin-1-yl}acetate;

(S)—N-({5-[4-(1H-imidazol-2-ylmethyl)piperazin-1-yl]imidazo[1,2-c]pyrimidin-2-yl}methyl)-N-methyl-5,6,7,8-tetrahydroquinolin-8-amine;

2-{4-[2-({methyl[(S)-5,6,7,8-tetrahydroquinolin-8-yl]amino}methyl)imidazo[1,2-c]pyrimidin-5-yl]piperazin-1-yl}acetic acid;

(S)—N-methyl-N-[(5-{4-[(1-methyl-1H-imidazol-2-yl)methyl]piperazin-1-yl}imidazo[1,2-c]pyrimidin-2-yl)methyl]-5,6,7,8-tetrahydroquinolin-8-amine;

(S)—N-methyl-N-[(5-{4-[(3-methylphenyl)methyl]piperazin-1-yl}imidazo[1,2-c]pyrimidin-2-yl)methyl]-5,6,7,8-tetrahydroquinolin-8-amine;

(S)—N-methyl-N-[(5-{4-[(4-methylphenyl)methyl]piperazin-1-yl}imidazo[1,2-c]pyrimidin-2-yl)methyl]-5,6,7,8-tetrahydroquinolin-8-amine;

(S)—N-({5-[4-(furan-2-ylmethyl)piperazin-1-yl]imidazo[1,2-c]pyrimidin-2-yl}methyl)-N-methyl-5,6,7,8-tetrahydroquinolin-8-amine;

(S)—N-methyl-N-({5-[4-(pyridin-2-ylmethyl)piperazin-1-yl]imidazo[1,2-c]pyrimidin-2-yl}methyl)-5,6,7,8-tetrahydroquinolin-8-amine;

(S)—N-methyl-N-[(5-{4-[(1-methyl-1H-pyrrol-2-yl)methyl]piperazin-1-yl}imidazo[1,2-c]pyrimidin-2-yl)methyl]-5,6,7,8-tetrahydroquinolin-8-amine;

(8 S)—N-methyl-N-[(5-{4-[(3-phenoxyphenyl)methyl]piperazin-1-yl}imidazo[1,2-c]pyrimidin-2-yl)methyl]-5,6,7,8-tetrahydroquinolin-8-amine;

(S)—N-methyl-N-({5-[4-(oxolan-2-ylmethyl)piperazin-1-yl]imidazo[1,2-c]pyrimidin-2-yl}methyl)-5,6,7,8-tetrahydroquinolin-8-amine;

2-({4-[2-({methyl[(S)-5,6,7,8-tetrahydroquinolin-8-yl]amino}methyl)imidazo[1,2-c]pyrimidin-5-yl]piperazin-1-yl}methyl)phenol;

(8 S)—N-{[5-(4-{[4-(dimethylamino)phenyl]methyl}piperazin-1-yl)imidazo[1,2-c]pyrimidin-2-yl]methyl}-N-methyl-5,6,7,8-tetrahydroquinolin-8-amine;

4-(2-{4-[2-({methyl[(S)-5,6,7,8-tetrahydroquinolin-8-yl]amino}methyl)imidazo[1,2-c]pyrimidin-5-yl]piperazin-1-yl}ethyl)phenol;

(S)—N-methyl-N-({5-[4-(thiophene-2-sulfonyl)piperazin-1-yl]imidazo[1,2-c]pyrimidin-2-yl}methyl)-5,6,7,8-tetrahydroquinolin-8-amine;

(S)—N-({5-[4-(benzenesulfonyl)piperazin-1-yl]imidazo[1,2-c]pyrimidin-2-yl}methyl)-N-methyl-5,6,7,8-tetrahydroquinolin-8-amine;

(S)—N-methyl-N-{[5-(4-{[4-(trifluoromethyl)phenyl]methyl}piperazin-1-yl)imidazo[1,2-c]pyrimidin-2-yl]methyl}-5,6,7,8-tetrahydroquinolin-8-amine;

(S)—N-methyl-N-({5-[4-(3-phenylbutyl)piperazin-1-yl] imidazo[1,2-c]pyrimidin-2-yl}methyl)-5,6,7,8-tetrahydroquinolin-8-amine;

3-({4-[2-({methyl[(S)-5,6,7,8-tetrahydroquinolin-8-yl] amino}methyl)imidazo[1,2-c]pyrimidin-5-yl]piperazin-1-yl}methyl)benzonitrile;

(S)—N-methyl-N-({5-[4-(1,3-thiazol-2-ylmethyl)piperazin-1-yl]imidazo[1,2-c]pyrimidin-2-yl}methyl)-5,6,7,8-tetrahydroquinolin-8-amine;

N-(3-chlorophenyl)-4-[2-({methyl[(S)-5,6,7,8-tetrahydroquinolin-8-yl]amino}methyl)imidazo[1,2-c]pyrimidin-5-yl]piperazine-1-carboxamide;

3-({4-[2-({methyl[(S)-5,6,7,8-tetrahydroquinolin-8-yl] amino}methyl)imidazo[1,2-c]pyrimidin-5-yl]piperazin-1-yl}methyl)phenol;

(S)—N-Methyl-N-((5-(piperazin-1-yl)imidazo[1,2-c]pyrimidin-2-yl)methyl)-3,4-dihydro-2H-pyrano[3,2-b] pyridin-4-amine; and (S)-(2-(((3,4-Dihydro-2H-pyrano[3,2-b]pyridin-4-yl) (methyl)amino)methyl)-5-(piperazin-1-yl)imidazo[1, 2-c]pyrimidin-3-yl)methanol;

or a pharmaceutically acceptable salt thereof.

10. A compound of claim 1 selected from the group consisting of (S)—N-((7-Chloro-5-(piperazin-1-yl)imidazo[1,2-c]pyrimidin-2-yl)methyl)-N-methyl-5,6,7,8-tetrahydroquinolin-8-amine;

(S)—N-((5-((3 S,5R)-3,5-Dimethylpiperazin-1-yl)imidazo[1,2-c]pyrimidin-2-yl)methyl)-N-methyl-5,6,7,8-tetrahydroquinolin-8-amine;

(8S)—N-((5-(3-aminopyrrolidin-1-yl)imidazo[1,2-c]pyrimidin-2-yl)methyl)-N-methyl-5,6,7,8-tetrahydroquinolin-8-amine;

(8S)—N-((5-(3-(dimethylamino)pyrrolidin-1-yl)imidazo [1,2-c]pyrimidin-2-yl)methyl)-N-methyl-5,6,7,8-tetrahydroquinolin-8-amine;

(S)—N-((5-((S)-hexahydropyrrolo[1,2-a]pyrazin-2(1H)-yl)imidazo[1,2-c]pyrimidin-2-yl)methyl)-N-methyl-5, 6,7,8-tetrahydroquinolin-8-amine;

((S)-1-(2-((methyl((S)-5,6,7,8-tetrahydroquinolin-8-yl) amino)methyl)imidazo[1,2-c]pyrimidin-5-yl)piperazin-2-yl)methanol;

(8S)—N-methyl-N-((5-(3-phenylpiperazin-1-yl)imidazo [1,2-c]pyrimidin-2-yl)methyl)-5,6,7,8-tetrahydroquinolin-8-amine;

(8S)—N-methyl-N-((5-(3-phenylpiperazin-1-yl)imidazo [1,2-c]pyrimidin-2-yl)methyl)-5,6,7,8-tetrahydroquinolin-8-amine;

(8S)—N-((5-(hexahydropyrrolo[3,4-c]pyrrol-2(1H)-yl) imidazo[1,2-c]pyrimidin-2-yl)methyl)-N-methyl-5,6,7, 8-tetrahydroquinolin-8-amine;

(8S)—N-methyl-N-((5-(5-methylhexahydropyrrolo[3,4-c]pyrrol-2(1H)-yl)imidazo[1,2-c]pyrimidin-2-yl) methyl)-5,6,7,8-tetrahydroquinolin-8-amine;

(S)—N-((5-(5,6-dihydro-[1,2,4]triazolo[4,3-a]pyrazin-7 (8H)-yl)imidazo[1,2-c]pyrimidin-2-yl)methyl)-N-methyl-5,6,7,8-tetrahydroquinolin-8-amine;

(S)—N-((5-(5,6-dihydroimidazo[1,2-a]pyrazin-7(8H)-yl) imidazo[1,2-c]pyrimidin-2-yl)methyl)-N-methyl-5,6,7, 8-tetrahydroquinolin-8-amine;

(S)—N-methyl-N-((5-(4-(2,2,2-trifluoroethyl)piperazin-1-yl)imidazo[1,2-c]pyrimidin-2-yl)methyl)-5,6,7,8-tetrahydroquinolin-8-amine;

((R)-4-(2-((methyl((S)-5,6,7,8-tetrahydroquinolin-8-yl) amino)methyl)imidazo[1,2-c]pyrimidin-5-yl)piperazin-2-yl)methanol;

((S)-4-(2-((methyl((S)-5,6,7,8-tetrahydroquinolin-8-yl) amino)methyl)imidazo[1,2-c]pyrimidin-5-yl)piperazin-2-yl)methanol;

(S)—N-((5-((7S,8aS)-7-fluorohexahydropyrrolo[1,2-a] pyrazin-2(1H)-yl)imidazo[1,2-c]pyrimidin-2-yl) methyl)-N-methyl-5,6,7,8-tetrahydroquinolin-8-amine;

(8S)—N-((5-(3,6-diazabicyclo[3.2.0]heptan-3-yl)imidazo[1,2-c]pyrimidin-2-yl)methyl)-N-methyl-5,6,7,8-tetrahydroquinolin-8-amine;

(8 S)—N-((5-(3,6-diazabicyclo[3.2.0]heptan-3-yl)imidazo[1,2-c]pyrimidin-2-yl)methyl)-N-methyl-5,6,7,8-tetrahydroquinolin-8-amine;

(8 S)—N-methyl-N-((5-(octahydro-2H-pyrido[1,2-a] pyrazin-2-yl)imidazo[1,2-c]pyrimidin-2-yl)methyl)-5, 6,7,8-tetrahydroquinolin-8-amine;

(8 S)—N-((5-(hexahydropyrazino[2,1-c][1,4]oxazin-8 (1H)-yl)imidazo[1,2-c]pyrimidin-2-yl)methyl)-N-methyl-5,6,7,8-tetrahydroquinolin-8-amine;

(8 S)—N-((5-(hexahydropyrazino[2,1-c][1,4]oxazin-8 (1H)-yl)imidazo[1,2-c]pyrimidin-2-yl)methyl)-N-methyl-5,6,7,8-tetrahydroquinolin-8-amine;

(8 S)—N-((5-(hexahydropyrrolo[3,4-b]pyrrol-5(1H)-yl) imidazo[1,2-c]pyrimidin-2-yl)methyl)-N-methyl-5,6,7, 8-tetrahydroquinolin-8-amine;

(8 S)—N-((5-(hexahydropyrrolo[3,4-b]pyrrol-5(1H)-yl) imidazo[1,2-c]pyrimidin-2-yl)methyl)-N-methyl-5,6,7, 8-tetrahydroquinolin-8-amine;

(8 S)—N-((5-(hexahydro-1H-pyrrolo[3,4-b]pyridin-6 (2H)-yl)imidazo[1,2-c]pyrimidin-2-yl)methyl)-N-methyl-5,6,7,8-tetrahydroquinolin-8-amine;

(8 S)—N-((5-(hexahydro-1H-pyrrolo[3,4-b]pyridin-6 (2H)-yl)imidazo[1,2-c]pyrimidin-2-yl)methyl)-N-methyl-5,6,7,8-tetrahydroquinolin-8-amine;

(S)—N-Methyl-N-((5-((3 S, 5R)-3,4,5-trimethylpiperazin-1-yl)imidazo[1,2-c]pyrimidin-2-yl)methyl)-5,6,7, 8-tetrahydroquinolin-8-amine;

((R)-1-methyl-4-(2-((methyl((S)-5,6,7,8-tetrahydroquinolin-8-yl)amino)methyl)imidazo[1,2-c]pyrimidin-5-yl)piperazin-2-yl)methanol;

((S)-1-methyl-4-(2-((methyl((S)-5,6,7,8-tetrahydroquinolin-8-yl)amino)methyl)imidazo[1,2-c]pyrimidin-5-yl) piperazin-2-yl)methanol;

(8S)—N-methyl-N-((5-(1-methylhexahydropyrrolo[3,4-b]pyrrol-5(1H)-yl)imidazo[1,2-c]pyrimidin-2-yl) methyl)-5,6,7,8-tetrahydroquinolin-8-amine;

(8S)—N-methyl-N-((5-(1-methylhexahydropyrrolo[3,4-b]pyrrol-5(1H)-yl)imidazo[1,2-c]pyrimidin-2-yl) methyl)-5,6,7,8-tetrahydroquinolin-8-amine;

(8S)—N-methyl-N-((5-(1-methyloctahydro-6H-pyrrolo [3,4-b]pyridin-6-yl)imidazo[1,2-c]pyrimidin-2-yl) methyl)-5,6,7,8-tetrahydroquinolin-8-amine;

(8S)—N-methyl-N-((5-(1-methyloctahydro-6H-pyrrolo [3,4-b]pyridin-6-yl)imidazo[1,2-c]pyrimidin-2-yl) methyl)-5,6,7,8-tetrahydroquinolin-8-amine;

(S)—N-((7-methoxy-5-(piperazin-1-yl)imidazo[1,2-c] pyrimidin-2-yl)methyl)-N-methyl-5,6,7,8-tetrahydroquinolin-8-amine;

(S)—N-((7-Methoxy-5-(4-methylpiperazin-1-yl)imidazo [1,2-c]pyrimidin-2-yl)methyl)-N-methyl-5,6,7,8-tetrahydroquinolin-8-amine;

(S)-(7-Methoxy-2-((methyl(5,6,7,8-tetrahydroquinolin-8-yl)amino)methyl)-5-(4-methylpiperazin-1-yl)imidazo [1,2-c]pyrimidin-8-yl)methanol; and (S)-2-(((4-Aminobutyl)(5,6,7,8-tetrahydroquinolin-8-yl) amino)methyl)imidazo[1,2-c]pyrimidin-5-ol;

or a pharmaceutically acceptable salt thereof.

11. A composition comprising a compound of formula I, or a pharmaceutically acceptable salt thereof, and a pharmaceutically acceptable carrier, diluent, or excipient.

\* \* \* \* \*